US012760304B2

(12) United States Patent
Stewart et al.

(10) Patent No.: US 12,760,304 B2
(45) Date of Patent: *Oct. 13, 2026

(54) STABILIZATION OF RNA FOR EXOGENOUS RNAi AGRICULTURAL APPLICATIONS AND FORMULATIONS

(71) Applicant: GREENLIGHT BIOSCIENCES. INC., Lexington, MA (US)

(72) Inventors: William Stewart, Durham, NC (US); Lorenzo Aulisa, Chesterfield, MO (US); David Villiard, Medford, MA (US); Jason Gillian, Durham, NC (US); Kayla Owens, Youngsville, NC (US); Namita Dodwadkar, North Reading, MA (US); Paul Boucher, Medford, MA (US); Justin Eldridge, Wilson, NC (US)

(73) Assignee: GREENLIGHT BIOSCIENCES, INC., Lexington, MA (US)

( * ) Notice: Subject to any disclaimer, the term of this patent is extended or adjusted under 35 U.S.C. 154(b) by 1081 days.

This patent is subject to a terminal disclaimer.

(21) Appl. No.: 17/737,426

(22) Filed: May 5, 2022

(65) Prior Publication Data

US 2022/0372478 A1 Nov. 24, 2022

Related U.S. Application Data

(60) Provisional application No. 63/184,508, filed on May 5, 2021.

(51) Int. Cl.

| | |
|---|---|
| ***C12N 15/113*** | (2010.01) |
| ***A01N 25/02*** | (2006.01) |
| ***A01N 25/22*** | (2006.01) |
| ***A01N 25/30*** | (2006.01) |
| ***C11D 1/94*** | (2006.01) |

(52) U.S. Cl.

CPC ............ *C12N 15/113* (2013.01); *A01N 25/02* (2013.01); *A01N 25/22* (2013.01); *A01N 25/30* (2013.01); *C11D 1/94* (2013.01)

(58) Field of Classification Search

None

See application file for complete search history.

(56) References Cited

U.S. PATENT DOCUMENTS

| | | | |
|---|---|---|---|
| 10,858,385 | B2 | 12/2020 | Cunningham et al. |
| 10,954,541 | B2 | 3/2021 | Blake et al. |
| 11,142,768 | B2 | 10/2021 | Barros Rodrigues et al. |
| 11,185,079 | B2 | 11/2021 | Barros Rodrigues et al. |
| 2011/0033842 | A1 | 2/2011 | Moon et al. |
| 2017/0029213 | A1 | 2/2017 | Johnson et al. |
| 2018/0237790 | A1 | 8/2018 | Maori et al. |
| 2018/0360030 | A1 | 12/2018 | Morgenstern et al. |
| 2019/0014448 | A1 | 1/2019 | Baek et al. |
| 2020/0009313 | A1 | 1/2020 | Diwan |
| 2020/0014904 | A1 | 1/2020 | Wetzstein et al. |

FOREIGN PATENT DOCUMENTS

| | | | |
|---|---|---|---|
| CN | 102424821 | A | 4/2012 |
| CN | 103109800 | | 2/2013 |
| WO | 20100147933 | A1 | 12/2010 |
| WO | 2016018887 | A1 | 2/2016 |
| WO | 2016073732 | A1 | 5/2016 |
| WO | 2020041782 | A1 | 2/2020 |
| WO | 2020102570 | A1 | 5/2020 |
| WO | 2020123419 | A2 | 6/2020 |
| WO | 20210204594 | A1 | 10/2021 |
| WO | 2021231791 | A2 | 11/2021 |
| WO | 20210231797 | A2 | 11/2021 |

OTHER PUBLICATIONS

USDA, Economic Research Service, Pest Management in U.S. Agriculture, AH-717, “Pests and Pest Management”, 3-6 (Year: 2025).*

EESR, EP22799571.9-1102/4333623 PCT/US2022027816, mailed Feb. 25, 2025, 11 pages.

INAPI, Chile No. 2023-03261 , PCT/2023-03261, mailed Jul. 4, 2025, 18 pages.

Bennett, et al. Barriers to efficient foliar uptake of dsRNA and molecular barriers to dsRNA activity in plant cells. Fronteras in Plant Science, 11:816. (2020).

Morozov, et al. Double-Stranded RNAs in plant protection against pathogenic organisms and viruses in agriculture. ActaNaturae, 11:13-21. (2019).

PCT Search Report & Written Opinion, PCT/US2022/027816, mailed Sep. 1, 2022, 9 pages.

Ghildiyal, Megha et al., “Small silencing RNAs: an expanding universe”, Nat Rev Genet., Feb. 2009, vol. 10, No. 1, pp. 94-108.

CL Office Action mailed Apr. 6, 2026 18 pages.

* cited by examiner

*Primary Examiner* — Genevieve S Alley

(74) *Attorney, Agent, or Firm* — Timothy H. Van Dyke; Wolter Van Dyke Davis, PLLC

(57) ABSTRACT

Compositions for providing stability to RNA may include a primary surfactant, and a metal-ion sequestrant. The primary surfactant may be a nonionic surfactant. The composition may be in a soluble liquid concentrate form and may be sufficient to provide shelf stability to RNA for one year at room temperature. Compositions for delivering RNA to a pest via exogenous, foliar application of the composition to a plant may comprise RNA; a primary surfactant; and a metal-ion sequestrant.

22 Claims, 20 Drawing Sheets

10% Atplus PFA

5% Atplus PFA

Time - 0 hours
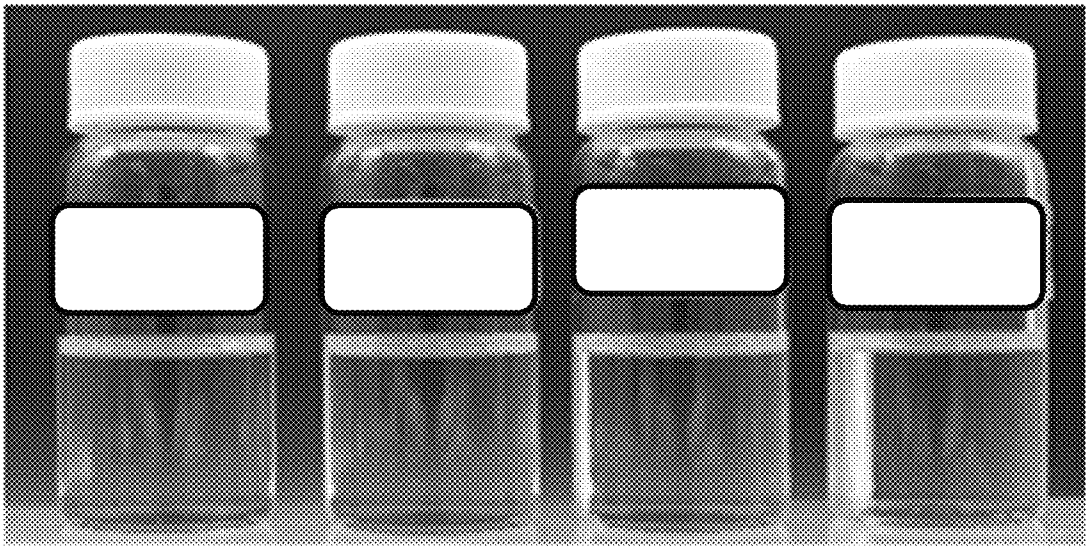
35 ppm | 342 ppm | 500 ppm | 1000 ppm
FIG. 6A FIG. 6B FIG. 6C FIG. 6D
Time - 24 hours
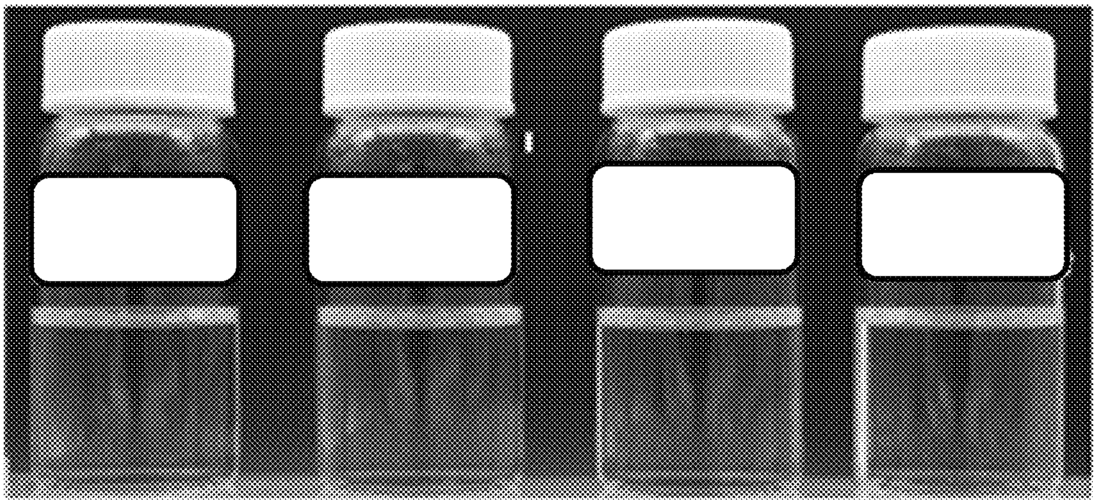
35 ppm | 342 ppm | 500 ppm | 1000 ppm
FIG. 6E FIG. 6F FIG. 6G FIG. 6H

TGAI – 8 g/L dsRNA 35 ppm 342 ppm 500 ppm 1000 ppm

TGAI - 4 g/L dsRNA 35 ppm 342 ppm 500 ppm 1000 ppm

Formulations after storage for 8 weeks at 40 C.

Formulations after storage for 2 weeks at 54 C.

Sample after 1 minute

TF_5 concentration is recommended: 0.05%

TF_12 concentration recommended: 0.75%

Concentration TF_16 recommended: 0.5%

1. 50 bp ladder
2. TForm191118_WS_05: 100J/cm2 [Reax 105M]
3. TForm191118_WS_06: 100J/cm2 [Kraftsperse 8828]
4. TForm191118_WS_07: 100J/cm2 [Reax 1425E]
5. TForm191118_WS_08: 100J/cm2 [Reax 910]
6. TForm191118_WS_09: 100J/cm2 [Reax 260]
7. TForm191118_WS_10: 100J/cm2 [blank]
8. TForm191118_WS_10: not irradiated
9. 50 bp ladder 1. 1 kb ladder
2. TForm200212_KO_01 [Morwet D-425]
3. TForm200212_KO_02 [Morwet IP]
4. TForm200212_KO_03 [Morwet EFW]
5. TForm200212_KO_04 [Triton X-100]
6. TForm200212_KO_05 [Tween L-1505]
7. TForm200212_KO_06 [Calsoft AOS-1245]
8. TForm191118_WS_10 [not exposed]
9. TForm191118_WS_10 [over exposed]
10. 1 kb ladder

STABILIZATION OF RNA FOR EXOGENOUS RNAi AGRICULTURAL APPLICATIONS AND FORMULATIONS

CROSS-REFERENCE TO RELATED APPLICATIONS

This application claims the benefit and priority of U.S. Provisional Application No. 63/184,508 filed on May 5, 2021, the contents of which is incorporated by reference in its entirety.

FIELD

The present disclosure relates generally to stabilization of RNA and more specifically to stabilization of RNA for exogenous RNAi agricultural applications and formulations.

BACKGROUND

RNA interference (RNAi) is a biological process in which a select biological process controlled by RNA is silenced, or modified, so that the process is not completed as intended, usually to the effect of mortality, suppression or stunting of growth, decrease in virulence, decrease in propagating/reproducing capacity, or elimination of a selected phenotype. In biological systems the RNAi pathway is initiated by enzymes such as, for example, Dicer, which cleaves dsRNA into shorter 20-25 base pair nucleotides that function as sequence specific interfering RNA. This interfering RNA promotes genetic silencing through several methods that effect translation of the host genetic material. As these genetic modifications are highly selective and species dependent, target organisms can effectively be managed through RNAi technologies without the off-target and ecological burden of conventional chemical pesticides. The active ingredient in RNAi based technologies, or interfering RNA, can be double stranded RNA (dsRNA) or single stranded RNA in various forms. Various structures of interfering RNA are known in the art, as discussed in, for example, Ghildiyal and Zamore, Small Silencing RNAs: An Expanding Universe, Nature Vol. 10, pp. 94-168 (2009). dsRNA is a naturally derived, water-soluble biopolymer that carries a net negative charge due to the phosphate linkages that form the backbone of dsRNA sequence. Various methods for making RNA are known in the art and the RNA of the current invention may be produced by any suitable method known in the art. Examples of methods of producing RNA include, but are not limited to, in vitro transcription (IVT), chemical synthesis, microbial fermentation, or cell free methods such as those described in U.S. Pat. No. 10,858,385, published May 16, 2019 (Pub. No. US 2019/0144489) and U.S. Pat. No. 10,954,541, published Oct. 12, 2017 (Pub. No. US2017/0292138), each of which is incorporated herein by reference. Examples of RNAi molecules for endogenous delivery, of use with the present invention, include but are not limited to, those described in U.S. Pat. No. 11,142,768 published May 14, 2020 (Pub No. US 2020/0149044), U.S. Pat. No. 11,185,079 published Mar. 26, 2020 (Pub No. US 2020/0093138), PCT/US/2021/032334 published Nov. 18, 2021 (Intl Publication No. WO 2021/231791), all of which are incorporated herein by reference.

RNAi technology has been shown to be a selective biological treatment for a wide variety of pests and ailments through internal biological process interference. A need exists for delivery of RNAi technology via exogenous delivery in formulations that help to maintain and improve RNA stability.

The discussion of shortcomings and needs existing in the field prior to the present invention is in no way an admission that such shortcomings and needs were recognized by those skilled in the art prior to the present disclosure.

A soluble liquid concentrate (SL) formulation must be stable for use in a product application. Stability in the concentrated form must be ensured for against responses to physical, chemical, microbial and enzymatic instability of the formulation. For physical stability, the formulation is evaluated for phase separation by visual or turbidity observations. For chemical stability, the active ingredient concentration on storage at elevated or controlled temperature is evaluated by liquid chromatography or gel electrophoresis. For microbial or enzymatic stability, the active ingredient concentration is evaluated after exposure to a known challenge mixture.

SUMMARY

Various embodiments relate to a composition for delivering RNA to a pest via exogenous, foliar application of the formulation to a plant. The composition may comprise RNA; a primary surfactant; and a metal-ion sequestrant. According to various embodiments, the primary surfactant may be a nonionic surfactant Other embodiments relate to a composition for providing stability to RNA. The composition may comprise a primary surfactant, and a metal-ion sequestrant. The primary surfactant may be a nonionic surfactant. The composition may be in a soluble liquid concentrate form and may be sufficient to provide shelf stability to RNA for one year at room temperature.

These and other features, aspects, and advantages of various embodiments will become better understood with reference to the following description, figures, and claims.

BRIEF DESCRIPTION OF THE FIGURES

Many aspects of this disclosure can be better understood with reference to the following figures.

FIGS. 6A, 6B, 6C, 6D are examples according to various embodiments, illustrating photographs of a formulation diluted into water at 35 ppm, 342 ppm, 500 ppm, and 1000 ppm, respectively, the photographs being taken immediately after the dilution into water.

FIGS. 6E, 6F, 6G, and 6H are examples according to various embodiments, illustrating photographs of a formulation diluted into water at 35 ppm, 342 ppm, 500 ppm, and 1000 ppm, respectively, the photographs being taken 24 hours after the dilution into water.

Figures 1A, 1B, 1C, 1D:
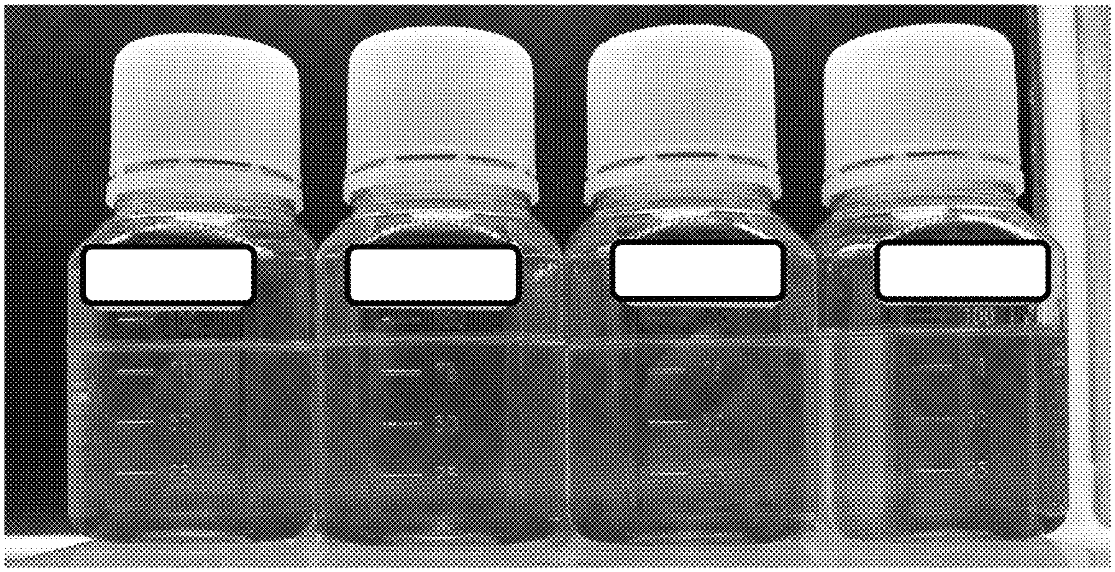
FIGS. 1A, 1B, 1C, and 1D are examples according to various embodiments, illustrating photographs of a compatible formulation after storage for 2 weeks at −10° C., and 2 and 8 weeks at 4° C., 8 weeks at 40° C., 2 weeks at 54° C.

It should be understood that the various embodiments are not limited to the examples illustrated in the figures.

DETAILED DESCRIPTION

Introduction and Definitions

This disclosure is written to describe the invention to a person having ordinary skill in the art, who will understand that this disclosure is not limited to the specific examples or embodiments described. The examples and embodiments are single instances of the invention which will make a much larger scope apparent to the person having ordinary skill in the art. Unless defined otherwise, all technical and scientific terms used herein have the same meaning as commonly understood by the person having ordinary skill in the art. It is also to be understood that the terminology used herein is for the purpose of describing examples and embodiments only, and is not intended to be limiting, since the scope of the present disclosure will be limited only by the appended claims.

All the features disclosed in this specification (including any accompanying claims, abstract, and drawings) may be replaced by alternative features serving the same, equivalent, or similar purpose, unless expressly stated otherwise. Thus, unless expressly stated otherwise, each feature disclosed is one example only of a generic series of equivalent or similar features. The examples and embodiments described herein are for illustrative purposes only and that various modifications or changes in light thereof will be suggested to the person having ordinary skill in the art and are to be included within the spirit and purview of this application. Many variations and modifications may be made to the embodiments of the disclosure without departing substantially from the spirit and principles of the disclosure. All such modifications and variations are intended to be included herein within the scope of this disclosure. For example, unless otherwise indicated, the present disclosure is not limited to particular materials, reagents, reaction materials, manufacturing processes, or the like, as such can vary. It is also to be understood that the terminology used herein is for purposes of describing particular embodiments only and is not intended to be limiting. It is also possible in the present disclosure that steps can be executed in different sequence where this is logically possible.

All numeric values are herein assumed to be modified by the term "about," whether or not explicitly indicated. The term "about" generally refers to a range of numbers that one of skill in the art would consider equivalent to the recited value (for example, having the same function or result). In many instances, the term "about" may include numbers that are rounded to the nearest significant figure.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, the term "standard temperature and pressure" or "room temperature and/or pressure" generally refers to 25° C. and 1 atmosphere. Standard temperature and pressure may also be referred to as "ambient conditions." Unless indicated otherwise, parts are by weight, temperature is in ° C., and pressure is at or near atmospheric. The terms "elevated temperatures" or "high-temperatures" generally refer to temperatures of at least 100° C.

Unless otherwise specified, all percentages indicating the amount of a component in a composition represent a percent by weight of the component based on the total weight of the composition. The term "mol percent" or "mole percent" generally refers to the percentage that the moles of a particular component are of the total moles that are in a mixture. The sum of the mole fractions for each component in a solution is equal to 1.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by prior disclosure. Further, the dates of publication provided could be different from the actual publication dates that may need to be independently confirmed.

For molecules having isomers or exhibiting one or more chiral centers only one of the possible variations may be shown for the sake of brevity. A person having ordinary skill in the art will appreciate that disclosure of all such variations is intended. When a specific variation is preferred, this disclosure will so state.

As used herein, the term “soluble liquid concentrate” (SL) refers to an aqueous formulation that contain a dissolved active ingredient. According to some embodiments, the active ingredient may be a salt.

As used herein, the term “dsRNA” refers to double-stranded RNA, which is RNA with two complementary strands.

As used herein, the terms “stability” or “instability” when used in relation to RNA refers to a degree to which the chemical makeup or physical state of RNA is subject to change over time from any cause. The RNA may be single-stranded RNA or dsRNA. An example of a lack of physical stability may include, but is not limited to, precipitation from a formulation. Examples of a lack of chemical stability may include, but are not limited to, degradation of the molecular structure of interfering RNA due to any or all of a variety of factors such as exposure to ultraviolet (UV) radiation, biocontamination, or chemical contamination. Examples of biocontamination may include, but are not limited to, exposure to bacteria, enzymes, or fungi. Examples of enzymes that may cause biocontamination and thereby impact chemical stability, include nucleases that degrade RNA. Examples of chemical contamination may include, but are not limited to, exposure to inhospitable pH ranges or to chemical agents. Physical and/or chemical stability of RNA may also be affected by thermal variations.

As used herein, the term “half-life of single stranded RNA” or “half-life of dsRNA”, refers to the time required for the stability of single stranded RNA or dsRNA to decrease by half.

As used herein, the term “surfactant” refers to compounds that lower the surface tension (or interfacial tension) between two liquids, between a gas and a liquid, or between a liquid and a solid. Surfactant molecules may have a hydrophobic portion (hydrophobe) and a hydrophilic portion (hydrophile).

As used herein, the terms “primary surfactant” and “secondary surfactant” may be used interchangeably with the terms “first surfactant” and “second surfactant.” The terms are used for convenience to refer to and to distinguish between various surfactants in a formulation or in a method of preparing a formulation.

As used herein, the term “biopesticide” refers to a composition that controls or kills pests.

As used herein, the term “RNAi” refers to RNA interference, a biological process in which RNA molecules inhibit gene expression or translation, by neutralizing targeted mRNA molecules As used herein, the term “exogenous application to a plant” refers to application of an RNAi biopesticide to the exterior of a plant. Exogenous application may avoid genetically modifying the plant.

dsRNA

Various embodiments relate to formulations that may include dsRNA; and various embodiments relate to methods of protecting a plant from a pest or pathogen that may include applying one or more of these formulations comprising dsRNA. Various embodiments relate to compositions for providing stability to dsRNA; and various embodiments relate to methods of stabilizing dsRNA that may include combining dsRNA with one or more of these compositions.

A wide variety of dsRNA may be employed according to the various embodiments. dsRNAs of use with the present disclosure, include, for example, those described in U.S. Pat. Nos. 11,185,079 and 11,142,768 and WIPO Publication Nos. WO 2020/123419 and WO 2021/231791, each of which is incorporated herein by reference. The types of dsRNA may vary based on any number of factors, including but not limited to size and structure.

The size of dsRNA is typically measured in terms of base pairs. According to various embodiments, the dsRNA that may be employed or stabilized according to various embodiments by have a number of base pairs in a range of from 10 to 1700. Each range described herein is intended to include all numerical values encompassed by the range. Furthermore, additional ranges may be formed from any lower limits and/or upper limits described herein. For example, the dsRNA that may be employed or stabilized according to various embodiments by have a number of base pairs in a range within a range having a lower limit and/or an upper limit. The range may include or exclude the lower limit and/or the upper limit. By way of example and not limitation, a lower limit and/or an upper limit may be selected from 10, 20, 30, 40, 50, 60, 70, 80, 90, 100, 200, 300, 400, 500, 600, 700, 800, 900, 1000, 1100, 1200, 1300, 1400, 1500, 1600, and 1700 base pairs. A range formed from a single lower limit includes at least the lower limit and all numerical values greater than the lower limit regardless of whether the values are explicitly recited in this disclosure. A range formed from a single upper limit includes at least the upper limit and all numerical values less than the upper limit regardless of whether the values are explicitly recited in this disclosure. A range formed from a combination of a lower limit and an upper limit includes at least the lower limit, the upper limit, and all numerical values therebetween regardless of whether the values are explicitly recited in this disclosure. For example, based on the set of exemplary upper limits and lower limits explicitly recited above, the dsRNA that may be employed or stabilized according to various embodiments by have a number of base pairs in a range of: about 10 to about 1000 base pairs, less than about 10 base pairs, greater than about 10 base pairs, less than about 1000 base pairs, or greater than about 1000 base pairs, etc. All such ranges are contemplated and are intended to be explicitly disclosed and recited. Each value recited is intended to be modified by the term "about."

Those having ordinary skill in the art will appreciate that dsRNA exists in a wide variety of structural arrangements. Those structures may include, but are not limited to double stranded structure, paperclip structure, hairpin structure, stem-loop structure, pre-microRNA structure, and artificial micro-RNA structure. The dsRNA that may be employed or stabilized according to various embodiments may have any of these structures.

Single Stranded RNA

Various embodiments relate to formulations that may include various single stranded RNAs, such as small interfering RNAs, piRNAs, or antisense RNAs; various embodiments relate to methods of protecting a plant from a pest that may include applying one or more of these formulations comprising single stranded RNA. Various embodiments relate to compositions for providing stability to single stranded RNA and various embodiments relate to methods of stabilizing single stranded RNA that may include combining single stranded RNA with one or more of these compositions.

The size of single stranded RNA is typically measured in terms of nucleotide bases. According to various embodiments, the single stranded RNA that may be employed or stabilized according to various embodiments bases in a range of from 10 to 1000 bases. Each range described herein is intended to include all numerical values encompassed by the range. Furthermore, additional ranges may be formed from any lower limits and/or upper limits described herein. For example, the single stranded RNA that may be employed or stabilized according to various embodiments by have a number of bases in a range within a range having a lower limit and/or an upper limit. The range may include or exclude the lower limit and/or the upper limit. By way of example and not limitation, a lower limit and/or an upper limit may be selected from 10, 20, 30, 40, 50, 60, 70, 80, 90, 100, 200, 300, 400, 500, 600, 700, 800, 900 and 1000 bases. A range formed from a single lower limit includes at least the lower limit and all numerical values greater than the lower limit regardless of whether the values are explicitly recited in this disclosure. A range formed from a single upper limit includes at least the upper limit and all numerical values less than the upper limit regardless of whether the values are explicitly recited in this disclosure. A range formed from a combination of a lower limit and an upper limit includes at least the lower limit, the upper limit, and all numerical values therebetween regardless of whether the values are explicitly recited in this disclosure. For example, based on the set of exemplary upper limits and lower limits explicitly recited above, the RNA that may be employed or stabilized according to various embodiments by have a number of bases in a range of: about 10 to about 1000 bases, less than about 10 bases, greater than about 10 bases, less than about 1000 bases, or greater than about 1000 bases, etc. All such ranges are contemplated and are intended to be explicitly disclosed and recited. Each value recited is intended to be modified by the term "about."

Primary Surfactant: Definition and Examples

According to various embodiments, the primary surfactant may be a nonionic surfactant. As used herein, the term "nonionic surfactant" refers to a class of surfactants comprising a neutrally charged hydrophile and hydrophobe. According to various embodiments, a nonionic surfactant may be selected for use in a formulation based on its compatibility with the concentrated formulation, ability to help stabilize dsRNA or single stranded RNA upon dilution in various water conditions, and application characteristics when sprayed onto the leaf surface.

Some examples of nonionic surfactants may include, but are not limited to, alkoxylates such as alkoxylated alcohols, alkoxylated phenols, alkoxylated fatty acids, alkoxylated monoalkaolamides, alkoxylated sorbitan esters, alkoxylated fatty amines. More specific examples of alkoxylates may include, but are not limited to alcohol ethoxylates, alkyl phenol ethoxylates, fatty acid ethoxylates, monoalkaolamide ethoxylates, sorbitan ester ethoxylates, fatty amine ethoxylates. Nonionic surfactants may also include polymeric surfactants, including but not limited to ethylene oxide-propylene oxide copolymers. Further examples of nonionic surfactants may include, but are not limited to linear alcohol ethoxylates, branched chain alcohol ethoxylates, fatty alcohol ethoxylate, alcohol alkoxylates, polyethylene modified fatty acid sorbitan esters, polyalkylglucosides, ethoxylated alkyl polyethylene glycol ethers, alkoxylated alkyl polyethylene glycol ethers, and fatty acid amides.

Examples of commercially available surfactants, which may be classified as nonionic surfactants for purposes of various embodiments may include, but are not limited to ATPLUS® PFA, BIO-SOFT® N23-6.5, TWEEN 20™, SYNERGEN® GA, LUTENSOL® TDA 8, LUTENSOL® TDA 9, T MAZ 20 K™, T MAZ 80 K™, and AGNIQUE® CSO-36.

Still further examples of nonionic surfactants include but are not limited to multihydroxy products. Examples of multihydroxy products may include, but are not limited to glycol esters, glycerol esters, polyglycerol esters, glucosides, polyglucosides, and sucrose esters. Additional examples of nonionic surfactants may include but are not limited to alkyl polyglycoside, CETOMACROGOL 1000™, cetostearyl alcohol, cetyl alcohol, cocamide dea, cocamide mea, decyl glucoside, decyl polyglucose, glycerol monostearate, IGEPAL® CA-630, ISOCETETH-20™, lauryl glucoside, maltosides, monolaurin, mycosubtilin, narrow-range ethoxylate, NONIDET P-40™ (NP-40), NONOXYNOL-9™ (NP-9), nonoxynols, octaethylene glycol monododecyl ether, n-octyl beta-d-thioglucopyranoside, octyl glucoside, oleyl alcohol, PEG-10 sunflower glycerides, pentaethylene glycol monododecyl ether, polidocanol, poloxamer, poloxamer 407, polyethoxylated tallow amine, polyglycerol polyricinoleate, polysorbate, polysorbate 20, polysorbate 80, sorbitan, sorbitan monolaurate, sorbitan monostearate, sorbitan tristearate, stearyl alcohol, surfactin, TRITON X-100™, and TWEEN 80™.

Nonoxynols also known as nonaethylene glycol or polyethylene glycol nonyl phenyl ether are mixtures of nonionic surfactants used as detergents, emulsifiers, wetting agents or defoaming agents.

Poloxamers are nonionic triblock copolymers composed of a central hydrophobic chain of polyoxypropylene (poly (propylene oxide)) flanked by two hydrophilic chains of polyoxyethylene (poly(ethylene oxide)). Poloxamer 407 is a hydrophilic non-ionic surfactant of the more general class of copolymers known as poloxamers. Poloxamer 407 is a triblock copolymer consisting of a central hydrophobic block of polypropylene glycol flanked by two hydrophilic blocks of polyethylene glycol (PEG).

Polysorbates are oily liquids derived from ethoxylated sorbitan (a derivative of sorbitol) esterified with fatty acids. Polysorbate 20 (common commercial brand names include Scattics, Alkest TW 20 and Tween 20) is a polysorbate-type nonionic surfactant formed by the ethoxylation of sorbitan before the addition of lauric acid. Its official IUPAC name is polyoxyethylene (20) sorbitan monolaurate. Polysorbate 80 is a nonionic surfactant and emulsifier derived from polyethoxylated sorbitan and oleic acid. Its official IUPAC name is polyoxyethylene (20) sorbitan monooleate.

ATPLUS® PFA is a commercially available alkoxylated alcohol, which may be purchased from Croda International Plc. TWEEN 20™ is a commercially available polyoxyethylene sorbitol ester, specifically polysorbate 20. TWEEN 80™ is a commercially available polysorbate surfactant, specifically polysorbate 80. SYNERGEN® GA is a commercially available is a sugar-based surfactant, comprising N-methyl-N-octanoyl/decanoylglucamine. LUTENSOL® TDA 8 and LUTENSOL® TDA 9 are commercially available ethoxylated tridecyl alcohols. T MAZ 20 K™ and T MAZ 80 K™ are commercially available sorbitan monooleates that have been ethoxylated with approximately 20 moles of ethylene oxide to give a water soluble, oil and water emulsifier. AGNIQUE® CSO-36 is a commercially available ethoxylated castor oil. CETOMACROGOL 1000™ is a commercially available polyethylene glycol hexadecyl ether, which is a nonionic surfactant produced by the ethoxylation of cetyl alcohol. IGEPAL® CA-630 is a commercially available nonionic, non-denaturing detergent. Its official IUPAC name is octylphenoxypolyethoxyethanol. ISOCETETH-20™ is a commercially available a polyethylene glycol ether formed by the ethoxylation of isocetyl alcohol. NONIDET P-40™ (NP-40) is a commercially available nonionic, non-denaturing detergent. Its official IUPAC name is octylphenoxypolyethoxyethanol. NONOXYNOL-9™ (NP-9) is a commercially available surfactant from the nonoxynol family. Its official IUPAC name is 2-{2-[2-(2-{2-[2-(2-{2-[2-(4-Nonylphenoxy)ethoxy] ethoxy}ethoxy)ethoxy]ethoxy}ethoxy)ethoxy] ethoxy}ethanol. TRITON X-100™ is a commercially available nonionic surfactant that has a hydrophilic polyethylene oxide chain and an aromatic hydrocarbon lipophilic or hydrophobic group. Its official IUPAC name is 2-[4-(2,4,4-trimethylpentan-2-yl)phenoxy]ethanol.

Secondary Surfactant: Definition and Examples

According to various embodiments, the secondary surfactant may be a cationic surfactant, a zwitterionic surfactant, and/or an amphoteric surfactant. As used herein, the term "cationic surfactant" refers to a class of surfactants comprising a positively charged hydrophile. As used herein, the terms "zwitterionic surfactant" or "amphoteric surfactant" refer to a class of surfactants comprising a hydrophile with both a positively-charged (cationic) center and a negatively-charged (anionic) center. The cationic portion is frequently based on primary, secondary, or tertiary amines or quaternary ammonium cations. The anionic portion can be more variable and include sulfates, sulfonates, phosphates, carbonates, and other proton donating moieties.

According to various embodiments, the secondary surfactant may be an alkyl ammonium halide, such as an alkyl ammonium chloride, that provides anti-microbial protection to dsRNA or single stranded RNA. Examples of cationic surfactants may include, but are not limited to behentrimonium chloride, benzalkonium chloride, benzethonium chloride, benzododecinium bromide, bronidox, carbethopendecinium bromide, cetalkonium chloride, cetrimonium bromide, cetrimonium chloride, cetylpyridinium chloride, didecyldimethylammonium chloride, dimethyldioctadecylammonium bromide, dimethyldioctadecylammonium chloride, dioleoyl-3-trimethylammonium propane, domiphen bromide, lauryl methyl gluceth-10 hydroxypropyl dimonium chloride, octenidine dihydrochloride, olaflur, n-Oleyl-1,3-propanediamine, pahutoxin, stearalkonium chloride, tetramethylammonium hydroxide, and thonzonium bromide.

Examples of zwitterionic surfactants may include but are not limited to CHAPS (3-[(3-cholamidopropyl)dimethylammonio]-1-propanesulfonate) detergent, cocamidopropyl betaine, cocamidopropyl hydroxysultaine, dipalmitoylphosphatidylcholine, egg lecithin, hydroxysultaine, lecithin, miltefosine, peptitergents, and sodium lauroamphoacetate.

Lauryl Betaine is an amphoteric surfactant derived from N-dodecyl-N,N-dialkanol amine with protein denaturing potency. As used herein, "betaine" refers to any neutral chemical compound with a positively charged cationic functional group such as a quaternary ammonium or phosphonium cation (generally: onium ions) that bears no hydrogen atom and with a negatively charged functional group such as a carboxylate group that may not be adjacent to the cationic site. A betaine is a specific type of zwitterion.

Examples of amine oxides include pyridine-N-oxide, a water-soluble crystalline solid with melting point 62-67° C., and N-methylmorpholine N-oxide, which is an oxidant. Various embodiments may employ C6 to C30 amine oxides, such as a C12 amine oxide.

According to various embodiments, AMMONYX® CETAC-30 and/or MAQUAT® LB may be used as secondary surfactants due to their cationic nature, and the role that the ammonium group in each molecule has towards anti-microbial activity. AMMONYX® CETAC-30 is a trade name of cetrimonium chloride, a cationic surfactant with known anti-microbial effect. MAQUAT® LB is a lauryl betaine, which due to the physical structure of betaines, contains an inner ammonium salt that carries a positive charge at all pH's and has an anti-microbial effect.

Other examples of secondary surfactants may include amine oxides, also known as amine-N-oxide and N-oxide. For example, lauryldimethylamine oxide (LDAO), also known as dodecyldimethylamine oxide (DDAO), is an amine oxide based zwitterionic surfactant.

Metal-Ion Sequestrant: Definition and Examples

As used herein, the terms "metal-ion sequestrant", "chelant", "chelator", "chelating agent", or "sequestering agent" refer to a polydentate ligand capable of forming two or more separate coordinate bonds to a single central atom. According to various embodiments a metal-ion chelator may inhibit enzymatic nuclease activity with respect to dsRNA or single stranded RNA. Examples of metal-ion sequestrants may include but are not limited to citrate, ammonium sulfate, acrylic copolymer (for example NOVERITE® K-775), ethylenediaminetetraacetic acid (EDTA), lignosulfonates, sodium lignosulfonates, glutamate diacetate (GLDA), diethylenetriaminepentaacidic acid (DTPA), N-carboxymethyliminobis (ethylenenitrilo)tetra(acetic acid), Ethylenediamine-N, N'-bis(2-hydroxyphenylacetic acid), N-(2-hydroxyethyl)ethylenediamine-N, N', N'-tiacetic acid, Ethylenediamine-N, N'-bis(2-hydroxy-6-methylphenylacetic acid, Ethylenediamine-N, N'-bis(4-carboxy-2-hydroxyphenylacetic acid, ethylenediamine-N,N'bis(2-hydroxy-5-sulfophenylacetic acid.

According to various embodiments, a metal-ion sequestrant may be selected for use in a formulation based on its ability to chelate divalent metal cations which are necessary for enzymatic activity of many common nucleases. For example, EDTA is a metal-ion sequestrant with the ability to chelate divalent metal cations which are necessary for enzymatic activity of many common nucleases. By chelating these metal-ions, any available nucleases are not able to perform their function and dsRNA or single stranded RNAis therefore protected from enzymatic mediated degradation in the concentrated formulation.

UV Protectant: Definition and Examples

As used herein, the term “UV protectant” or “dispersant surfactant” or “dispersing surfactant” refers to a composition that increases the stability of dsRNA or single stranded RNA when exposed to ultra-violet radiation. Examples of UV protectants may include but are not limited to conjugated aromatic type surfactants. For example, UV protectants may include but are not limited to polymeric surfactants containing conjugated aromatic functionalities, exemplified by lignin; naphthalene-based surfactants, such as lignosulfonates; dioctyl sodium sulfosuccinates; and naphthalene sulfonate condensates. Kraft lignin is a kind of industrial lignin obtained from Kraft pulp, which accounts for about 85% of the total lignin production in the world. Further examples of UV protectants may include but are not limited to conjugated aromatic surfactants, such as lignosulfonates and napthalene sulfonates, most specifically REAX® 105M, REAX® 910, KRAFTSPERSE® 8828, REAX® 1425E, REAX® 260, MORWET® D-425, MORWET® EFW, and MORWET® IP.

REAX® 105M is a commercially available, highly sufonated, low molecular weight kraft lignosulfonate dispersant with a low free electrolyte content. REAX® 910 is a commercially available, medium sulfonated kraft lignin dispersant featuring low free electrolyte content, low conductivity and a near neutral pH. REAX® 1425E is a commercially available ethoxylated kraft lignosulfonate with excellent water solubility. REAX® 260 is a commercially available sodium sulfite lignosulfonate product used as a dispersant in dry formulations such as water dispersible granule or wettable powder. KRAFTSPERSE® 8828 is a commercially available, hydrophobic, high molecular weight lignin-based dispersant. MORWET® D-425 is a commercially available sodium salt of naphthalene sulfonate condensate. MORWET® EFW is a commercially available sodium alkyl naphthalene sulfonate blend and MORWET® IP is a commercially available sodium isopropyl naphthalene sulfonate.

Antifreeze Agent: Definition and Examples

As used herein, the term “antifreeze agent” refers to an additive which lowers the freezing point of a water-based liquid. Examples of antifreeze agents may include but are not limited to propylene glycol, methanol, ethanol, propanol, isopropanol, alkylene glycol ethers, alkylene glycol alkyl ethers, and glycerols. According to various embodiments, an antifreeze agent may be selected for use in a formulation based on its performance at low temperature to provide stability for the formulation and the individual components at temperatures below freezing. For example, propylene glycol is a common, alcohol based, solvent used for its superior performance at low temperature, and as such provides stability for the formulation and the individual components at temperatures below freezing.

Buffer: Definition and Examples

As used herein, the term “buffer” refers to a solution able to resist pH change upon the addition of acidic or basic components and functions to neutralize small amounts of added acid or base, to maintain the pH of a solution for relative stability. According to various embodiments a buffer may be selected to mimic a neutral pH and to help prevent the possibility of acid/base hydrolysis and subsequent degradation of dsRNA or single stranded RNA in the formulation.

According to various embodiments, a phosphate-based buffer may be used. For example, according to various embodiments, a potassium phosphate buffer at pH 7 may be used to mimic a neutral pH and to help prevent the possibility of acid/base hydrolysis and subsequent degradation of dsRNA or single stranded RNA in the formulation. Another example of a buffer composition, according to various embodiments, is a combination of phosphate-citrate buffer at pH 7. This composition may be used to mimic neutral pH, to help prevent possibility of acid/base hydrolysis of dsRNA or single stranded RNA within the formulation, and to provide an additional potential chelation effect through the inclusion of citrate. Another example of a buffer composition, according to various embodiments is a citrate buffer at pH 6. Such a composition may be used to increase chelation through use of citrate buffer, and improve protection against microbial contamination through use of pH 6.

Examples of buffers may include but are not limited to potassium phosphate, Bis-Tris (bis-tris methane), ADA (2-[(2-amino-2-oxoethyl)-(carboxymethyl)amino]acetic acid), ACES (2-(carbamoylmethylamino)ethanesulfonic acid), PIPES (1,4-Piperazinediethanesulfonic acid), MOPSO (2-hydroxy-3-morpholin-4-ylpropane-1-sulfonic acid), BES (2-[Bis(2-hydroxyethyl)amino]ethanesulfonic acid), MOPS (3-Morpholinopropane-1-sulfonic acid), TES (2-[[1,3-dihydroxy-2-(hydroxymethyl)propan-2-yl]amino]ethanesulfonic acid), HEPES (2-[4-(2-hydroxyethyl)piperazin-1-yl]ethanesulfonic acid), DIPSO (3-[Bis(2-hydroxyethyl)amino]-2-hydroxy-1-propanesulfonic acid), MOBS (4-(4-Morpholinyl)-1-butanesulfonic acid), TAPSO (3-{[1,3-Dihydroxy-2-(hydroxymethyl)-2-propanyl]amino}-2-hydroxy-1-propanesulfonic acid), TRIS (3-{1,1,1,5,5,5-Hexamethyl-3-[(trimethylsilyl)oxy]-3-trisiloxanyl}propyl methacrylate), and Citrate (2-Oxido-1,2,3-propanetricarboxylate).

Antifoam Agent: Definition and Examples

As used herein, the terms “antifoam agent” or “defoamer” refer to a compound that reduces and hinders formation of foam in industrial process liquids. Examples of antifoam agents may include but are not limited to insoluble oils, polydimethylsiloxanes and other silicones, certain alcohols, stearates and glycols. Examples of specific, commercially available antifoam agents may include but are not limited to SAG 1572™, DREWPLUS® L-768, ANTIFOAM 8830™, AGNIQUE® DFM 111S, SILFOAM® SE 11, SILFOAM® SE 21, ANTIFOAM 100™, ANTIFOAM HL 550™, SAG 1599™, ANTIFOAM 8810™, ANTIFOAM 8820™, and ANTIFOAM GN11P™. According to various embodiments, SAG 1572™ and DREWPLUS® L-768 were selected to reduce persistent foam upon dilution in a spray tank.

SAG 1572™ and SAG 1599™ is a commercially available antifoam emulsion comprising polydimethylsiloxane. DREWPLUS® L-768 is a commercially available antifoam emulsion comprising polydimethylsiloxane. ANTIFOAM 8830™, ANTIFOAM 100™, ANTIFOAM HL 550™, ANTIFOAM 8810™, ANTIFOAM 8820™, and ANTIFOAM GN11P™ are commercially available antifoam emulsions comprising polydimethylsiloxane. AGNIQUE® DFM 111S is a commercially available antifoam emulsion comprising polydimethylsiloxane and propylene glycol. SILFOAM® SE 11 and SILFOAM® SE 21 are commercially available low viscosity silicone-based defoamer emulsions.

Biological Preservative: Definition and Examples

As used herein, the term "biological preservative" refers to a substance used for controlling organisms that are harmful to crops, human or animal health or that cause damage to natural or manufactured products. Examples of biological preservatives may include but are not limited to KATHON® CG/ICP, ROCIMA® BT2S, and PROXEL® GXL.

KATHON® CG/ICP is a broad-spectrum fungicide and biocide that includes the actives 5-chloro-2-methyl-4-isothiazolin-3-one (CMIT) and 2-methyl-4-isothiazolin-3-one (MIT). ROCIMA® BT2S and PROXEL® GXL are broad-spectrum biocides that include of 1,2-benzisothiazolin-3-one (BIT) as an active.

General Discussion

Various embodiments provide a formulation utilizing dsRNA or single stranded RNA as the active ingredient for use as biopesticide in agricultural market. According to various embodiments, the formulation may be a soluble liquid concentrate. The formulation may provide necessary physical and chemical stability to dsRNA or single stranded RNA, so that a foliar or other application of the formulation can aid pest or pathogen control in a pest or pathogen management program through exogenous RNAi. Various embodiments of the formulation show adequate performance in CIPAC/testing methods for SL type formulations for foliar application. Various embodiments of the formulation may improve chemical and physical stability of dsRNA or single stranded RNA to enable shelf-stable dsRNA or single stranded RNA based agricultural formulations and may prevent or limit RNA degradation due to bacterial and fungal contamination, enzymatic nuclease activity, and UV radiation.

By utilizing the high specificity and efficacy of exogenously delivered RNA to achieve RNAi in selected genomic targets, selected pest populations may be targeted and eliminated with a significant decrease with adverse biological effects. *Leptinotarsa decemlineata* have shown increased resistance to current potato pest management programs. Development of SL type formulations for exogenous delivery of dsRNA to *Leptinotarsa decemlineata* have demonstrated a high degree of degradation when exposed to common environmental and storage conditions such as septic or non-sterile environments, microbial contamination, and UV radiation. This invention aims to provide formulations that allows RNA for exogenous delivery to be shelf stable, eliminating or reducing RNA degradation due to contamination or environmental conditions.

Various embodiments relate to a soluble liquid concentrate type formulation for delivery of dsRNA due to both the inherent negative charge, and water solubility of the biopolymer. The formulation type is characterized as an aqueous based concentrate in which the active ingredient is completely solubilized in the formulation media. The inactive ingredients, or co-formulants of an soluble liquid concentrate formulation may include several classes of co-formulants, in addition to formulation-specific ones to help stabilize or protect the active ingredient from degradation as needed. The formulation design, according to various embodiments, may include co-formulants designated as an anti-freeze agent to prevent freezing at low temperatures, one or more broad spectrum preservative components for microbial and fungal protection, a primary surfactant to aid stability and foliar application to plants, an anti-foam agent to prevent persistent foam upon dilution in the spray tank, a pH buffer to prevent acid/base hydrolysis of dsRNA. However, since dsRNA is a biopolymer and faces specific degradation issues not common to other polymers or small molecules, additional co-formulants may be added, according to various embodiments, to include a metal ion chelator to help inhibit nuclease activity through sequestering divalent metal cations, and an anionic dispersant type surfactant consisting of a (polymeric, preferred) conjugated aromatic functionality to prevent dsRNA degradation after foliar application due to UV radiation. Some embodiments further include a cationic or zwitterionic agent (also referred to herein as a "secondary surfactant") as an additional surfactant with an anti-microbial effect.

Various embodiments may provide a shelf-stable soluble liquid concentrate formulation containing dsRNA or single stranded RNA for foliar application. The formulation composition, according to various embodiments, may aid RNA stability in presence of common contaminants and environmental conditions that otherwise result in rapid degradation of RNA.

Various embodiments enable the production of cost-effective dsRNA or single stranded RNA formulations that may provide a low toxicity and high selectivity RNAi treatment for exogenous foliar application. Enablement of RNAi technology as foliar application in agricultural industry is particularly beneficial, because various target species have shown enhanced resistance to current commercial pest management programs.

During the formulation development process each individual component was selected for performance, stability, and compatibility according to the needs of the formulation design. Table 1 provides a list of components for an exemplary formulation as well as a brief, generalized description of each components function in the overall formulation.

TABLE 1

| Function | Exemplary Embodiment | Description |
|---|---|---|
| AI | dsRNA | dsRNA is active ingredient in RNAi |
| Primary Surfactant | ATPLUS ® PFA | Physical Stability and Spray Application Aid |
| Metal-ion Sequestrant | EDTA, Tetrasodium Tetrahydrate Salt | Metal ion sequestrant resulting in inhibition of nuclease activity |
| Anti-Freeze Agent | Propylene Glycol | Provides Stability in Low Temperatures |
| First Buffer | Potassium Phosphate Buffer pH 7 | pH buffer to prevent acid/base hydrolysis of dsRNA in formulation |
| Second Buffer | Phosphate-Citrate Buffer pH 7 | pH Buffer to prevent acid/base hydrolysis of dsRNA in formulation |
| Secondary Surfactant | AMMONYX ® CETAC-30 | Cationic/Zwitterionic surfactant. Antimicrobial effect, Chemical Stabilizer for dsRNA |
| UV Protectant (aka Dispersant Surfactant) | Conjugated Aromatic Surfactant | Provides dsRNA Stability from UV degradation |
| Antifoam agent | SAG1572/ DREWPLUS ® L-768, | Anti-foam component for spray solution |

TABLE 1-continued

| Function | Exemplary Embodiment | Description |
|---|---|---|
| First Biological Preservative | KATHON ® CG/ICP | Mixture of CMIT, and MIT preservatives |
| Second Biological Preservative | ROCIMA ® BT2S | Solution of BIT preservative |

Terminology Notes:
(1) In embodiments where a plurality of buffers are present, such as the first buffer and the second buffer, they may be referred to collectively as "buffer." When each of any plurality of buffers are phosphate-based buffers, they may be referred to collectively as "buffer" or "phosphate buffer."
(2) In embodiments where a plurality of biological preservatives are present, such as the first biological preservative and the second biological preservative, they may be referred to collectively as "biological preservative."

Various embodiments relate to a formulation for delivering dsRNA or single stranded RNA to a pest via exogenous, foliar application of the formulation to a plant. According to various embodiments, the formulation may be a soluble liquid concentrate. According to various embodiments, the formulation may comprise: RNA; a primary surfactant; and a metal-ion sequestrant; optionally a secondary surfactant; optionally a UV protectant; optionally a buffer; optionally a biological preservative; optionally an antifoam agent; and optionally an antifreeze agent. In some embodiments the formulation comprises: RNA, a primary surfactant; a metal-ion sequestrant; and a secondary surfactant; optionally a UV protectant; optionally a buffer; optionally a biological preservative; optionally an antifoam agent; and optionally an antifreeze agent. In some embodiments the formulation comprises: RNA, a primary surfactant; a metal-ion sequestrant; and a UV protectant; optionally a secondary surfactant; optionally a buffer; optionally a biological preservative; optionally an antifoam agent; and optionally an antifreeze agent.

Various embodiments relate to a composition for providing sufficient stability to RNA to facilitate delivery of RNA to a pest via exogenous, foliar application of the composition and RNA to a plant. The composition may comprise a primary surfactant; and a metal-ion sequestrant; optionally a secondary surfactant; a UV protectant; optionally a buffer; optionally a biological preservative; optionally an antifoam agent; and optionally an antifreeze agent. The composition may comprise a primary surfactant; metal-ion sequestrant; and a secondary surfactant; optionally a UV protectant; optionally a buffer; optionally a biological preservative; optionally an antifoam agent; and optionally an antifreeze agent. The composition may comprise a primary surfactant; metal-ion sequestrant; and a UV protectant; optionally a secondary surfactant; optionally a buffer; optionally a biological preservative; optionally an antifoam agent; and optionally an antifreeze agent.

In either the formulation or the composition referenced above, the RNA may be any suitable dsRNA or RNA as described herein. According to various embodiments of the formulation referenced above, RNA may be present in an amount of from about 0.05 to about 10 percent by weight based on the total weight of the formulation or 0.25 to about 2 percent by weight based on total weight of the formulation. According to various embodiments of the formulation referenced above, the dsRNA or single stranded RNA may be present in an amount within a range having a lower limit and/or an upper limit. The range can include or exclude the lower limit and/or the upper limit. The lower limit and/or upper limit can be selected from about 0.05, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.05, 1.1, 1.15, 1.2, 1.25, 1.3, 1.35, 1.4, 1.45, 1.5, 1.55, 1.6, 1.65, 1.7, 1.75, 1.8, 1.85, 1.9, 1.95, 2, 2.05, 2.1, 2.15, 2.2, 2.25, 2.3, 2.35, 2.4, 2.45, 2.5, 2.55, 2.6, 2.65, 2.7, 2.75, 2.8, 2.85, 2.9, 2.95, 3, 3.05, 3.1, 3.15, 3.2, 3.25, 3.3, 3.35, 3.4, 3.45, 3.5, 3.55, 3.6, 3.65, 3.7, 3.75, 3.8, 3.85, 3.9, 3.95, 4, 4.05, 4.1, 4.15, 4.2, 4.25, 4.3, 4.35, 4.4, 4.45, 4.5, 4.55, 4.6, 4.65, 4.7, 4.75, 4.8, 4.85, 4.9, 4.95, 5, 5.05, 5.1, 5.15, 5.2, 5.25, 5.3, 5.35, 5.4, 5.45, 5.5, 5.55, 5.6, 5.65, 5.7, 5.75, 5.8, 5.85, 5.9, 5.95, 6, 6.05, 6.1, 6.15, 6.2, 6.25, 6.3, 6.35, 6.4, 6.45, 6.5, 6.55, 6.6, 6.65, 6.7, 6.75, 6.8, 6.85, 6.9, 6.95, 7, 7.05, 7.1, 7.15, 7.2, 7.25, 7.3, 7.35, 7.4, 7.45, 7.5, 7.55, 7.6, 7.65, 7.7, 7.75, 7.8, 7.85, 7.9, 7.95, 8, 8.05, 8.1, 8.15, 8.2, 8.25, 8.3, 8.35, 8.4, 8.45, 8.5, 8.55, 8.6, 8.65, 8.7, 8.75, 8.8, 8.85, 8.9, 8.95, 9, 9.05, 9.1, 9.15, 9.2, 9.25, 9.3, 9.35, 9.4, 9.45, 9.5, 9.55, 9.6, 9.65, 9.7, 9.75, 9.8, 9.85, 9.9, 9.95, and 10 percent by weight. For example, according to various embodiments of the formulation referenced above, the dsRNA or single stranded RNA may be present in an amount of from about 0.25 to about 2 percent by weight based on the total weight of the formulation, or any combination of lower limits and upper limits described.

In either the formulation or the composition referenced above, the primary surfactant may be any suitable primary surfactant or combination of primary surfactants as described herein. According to various embodiments of the formulation or the composition referenced above, the primary surfactant may be present in an amount of from about 1 to about 10 percent by weight based on the total weight of the formulation or of the composition or in an amount of from about 4 to about 6 percent by weight based on the total weight of the formulation or of the composition. According to various embodiments of the formulation or the composition referenced above, the primary surfactant may be present in an amount within a range having a lower limit and/or an upper limit. The range can include or exclude the lower limit and/or the upper limit. The lower limit and/or upper limit can be selected from about 0.5, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, and 15 percent by weight. For example, according to various embodiments of the formulation or the composition referenced above, the primary surfactant may be present in an amount of from about 1 to about 10 percent or about 4 to about 6 percent by weight based on the total weight of the formulation or of the composition, or any combination of lower limits and upper limits described.

In either the formulation or the composition referenced above, the secondary surfactant may be any suitable secondary surfactant or combination of secondary surfactants as described herein. According to various embodiments of the formulation or the composition referenced above, the secondary surfactant may be present in an amount of from about 0.01 to about 3 percent by weight based on the total weight of the formulation or of the composition. According to various embodiments of the or the composition referenced above, the secondary surfactant may be present in an amount of from about 0.01 to about 1 percent by weight based on the total weight of the formulation or of the composition. According to various embodiments of the formulation or the composition referenced above, the secondary surfactant may be present in an amount within a range having a lower limit and/or an upper limit. The range can include or exclude the lower limit and/or the upper limit. The lower limit and/or upper limit can be selected from about 0.01, 0.05, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, and 5 percent by weight. For example, according to various embodiments of the formulation or the composition referenced above, the secondary surfactant may be present in an amount of from about 0.01 to about 3 percent by weight based on the total weight of the formulation or of the composition, or any combination of lower limits and upper limits described. In additional examples, according to various embodiments of the formulation or the composition referenced above, the secondary surfactant may be present in an amount of from about 0.01 to about 1 percent by weight based on the total weight of the formulation or of the composition, or any combination of lower limits and upper limits described.

In either the formulation or the composition referenced above, the metal-ion sequestrant may be any suitable metal-ion sequestrant or combination of metal-ion sequestrants as described herein. According to various embodiments of the formulation or the composition referenced above, the metal-ion sequestrant may be present in an amount of from about 0.1 to about 5 percent by weight based on the total weight of the formulation or of the composition. According to various embodiments of the formulation or the composition referenced above, the metal-ion sequestrant may be present in an amount of from about 0.1 to about 2 percent by weight based on the total weight of the formulation or of the composition. According to various embodiments of the formulation or the composition referenced above, the metal-ion sequestrant may be present in an amount within a range having a lower limit and/or an upper limit. The range can include or exclude the lower limit and/or the upper limit. The lower limit and/or upper limit can be selected from about 0.05, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, and 5 percent by weight. For example, according to various embodiments of the formulation or the composition referenced above, the metal-ion sequestrant may be present in an amount of from about 0.1 to about 5 percent by weight based on the total weight of the formulation or of the composition, or any combination of lower limits and upper limits described. For example, according to various embodiments of the formulation or the composition referenced above, the metal-ion sequestrant may be present in an amount of from about 0.1 to about 2 percent by weight based on the total weight of the formulation or of the composition, or any combination of lower limits and upper limits described.

In either the formulation or the composition referenced above, the UV protectant (aka dispersant surfactant) may be any suitable UV protectant, dispersant surfactant, or combinations of thereof as described herein or combinations hereof. According to various embodiments of the formulation or the composition referenced above, the UV protectant may be present in an amount of from about 1 to about 4 percent or from about 1 to about 2 percent by weight based on the total weight of the formulation or of the composition. According to various embodiments of the formulation or the composition referenced above, the UV protectant may be present in an amount within a range having a lower limit and/or an upper limit. The range can include or exclude the lower limit and/or the upper limit. The lower limit and/or upper limit can be selected from about 0.05, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, and 5 percent by weight. For example, according to various embodiments of the formulation or the composition referenced above, the UV protectant may be present in an amount of from about 1 to about 4 percent or from about 1 to about 2 percent by weight based on the total weight of the formulation or of the composition, or any combination of lower limits and upper limits described.

In either the formulation or the composition referenced above, the buffer may be any suitable buffer or combination of buffers as described herein. According to various embodiments of the formulation or the composition referenced above, the buffer may be present in an amount of from about 1 to about 3 percent by weight based on the total weight of the formulation or of the composition. According to various embodiments of the formulation or the composition referenced above, the buffer may be present in an amount within a range having a lower limit and/or an upper limit. The range can include or exclude the lower limit and/or the upper limit. The lower limit and/or upper limit can be selected from about 0.05, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, and 5 percent by weight. For example, according to various embodiments of the formulation or the composition referenced above, the buffer may be present in an amount of from about 1 to about 3 percent by weight based on the total weight of the formulation or of the composition, or any combination of lower limits and upper limits described. In some embodiments the buffer is present in a concentration of at least about 200 mM or at least about 242 mM.

In either the formulation or the composition referenced above, the biological preservative may be any suitable biological preservative or combination of biological preservatives as described herein. According to various embodiments of the formulation or the composition referenced above, the biological preservative may be present in an amount of from about 0.05 to about 1 percent by weight based on the total weight of the formulation or of the composition. According to various embodiments of the formulation or the composition referenced above, the biological preservative may be present in an amount within a range having a lower limit and/or an upper limit. The range can include or exclude the lower limit and/or the upper limit. The lower limit and/or upper limit can be selected from about 0.05, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, and 5 percent by weight. For example, according to various embodiments of the formulation or the composition referenced above, the biological preservative may be present in an amount of from about 0.05 to about 1 percent by weight based on the total weight of the formulation or of the composition, or any combination of lower limits and upper limits described.

In either the formulation or the composition referenced above, the antifoam agent may be any suitable antifoam agent or combination of antifoam agents as described herein. According to various embodiments of the formulation or the composition referenced above, the antifoam agent may be present in an amount of from about 0.025 to about 0.2 percent by weight based on the total weight of the formulation or of the composition. According to various embodiments of the formulation or the composition referenced above, the antifoam agent may be present in an amount of from about 0.025 to about 0.1 percent by weight based on the total weight of the formulation or of the composition. According to various embodiments of the formulation or the composition referenced above, the antifoam agent may be present in an amount within a range having a lower limit and/or an upper limit. The range can include or exclude the lower limit and/or the upper limit. The lower limit and/or upper limit can be selected from about 0.025, 0.05, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, and 5 percent by weight. For example, according to various embodiments of the formulation or the composition referenced above, the antifoam agent may be present in an amount of from about 0.025 to about 0.1 percent by weight based on the total weight of the formulation or of the composition, or any combination of lower limits and upper limits described. In additional embodiments, the formulation or the composition referenced above, the antifoam agent may be present in an amount of from about 0.025 to about 0.2 percent by weight based on the formulation or of the composition, or any combination of lower limits and upper limits described.

In either the formulation or the composition referenced above, the antifreeze agent may be any suitable antifreeze agent or combination of antifreeze agents as described herein. According to various embodiments of the formulation or the composition referenced above, the antifreeze agent may be present in an amount of from about 5 to about 15 percent by weight based on the total weight of the formulation or of the composition. According to various embodiments of the formulation or the composition referenced above, the antifreeze agent may be present in an amount within a range having a lower limit and/or an upper limit. The range can include or exclude the lower limit and/or the upper limit. The lower limit and/or upper limit can be selected from about 1, 2, 3, 4, 5, 6, 7, 8, 9, 10, 11, 12, 13, 14, 15, 16, 17, 18, 19, and 20 percent by weight. For example, according to various embodiments of the formulation or the composition referenced above, the antifreeze agent may be present in an amount of from about 5 to about 15 percent by weight based on the total weight of the formulation or of the composition, or any combination of lower limits and upper limits described.

Various embodiments relate to a method of protecting a plant from a pest, the method comprising applying the formulation, according to any of the embodiments described herein exogenously to the plant. The formulation, according to various embodiments, may further comprises water. The water may dilute the exogenous RNAi biopesticide by a factor of from about 15 to about 300. The water may dilute the exogenous RNAi biopesticide by a factor within a range having a lower limit and/or an upper limit. The range can include or exclude the lower limit and/or the upper limit. The lower limit and/or upper limit can be selected from about 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, and 400. For example, according to certain embodiments, the water may dilute the exogenous RNAi biopesticide by a factor of from about 15 to about 300, or any combination of lower limits and upper limits described. The formulation may be applied to foliage of the plant, for example by spraying.

Various embodiments relate to a method of stabilizing dsRNA comprising combining dsRNA with the composition for providing sufficient stability to dsRNA to facilitate delivery of dsRNA to a pest via exogenous, foliar application of the composition and dsRNA to a plant. In some embodiments the dsRNA remains in solution and does not precipitate after 2 weeks at 54° C. In some embodiments the dsRNA evidences no detectable degradation (i.e., within the range of known variation for HPLC) or minimal degradation (less than 5%) as measured by HPLC comparing an initial dsRNA concentration and comparing it to dsRNA concentration after 2 weeks at 54° C. In some embodiments the pH of the composition varies by no more than +/−2 units after 2 weeks at 54° C. In some embodiments the time and temperature conditions for these stability evaluations are 1 year at room temperature, 2 years at room temperature, 4 weeks 54° C., 8 weeks 54° C., at 2 weeks at −10° C., 2 weeks at 4° C., 2 weeks at 40° C., 4 weeks at 4° C., 4 weeks at 40° C., 8 weeks at 4° C., or 8 weeks at 40° C., Table 2 provides details of a formulation, according to various embodiments. It should be understood that the specific formulation detailed in Table 2 (or any specific formulation detailed herein) does not limit the scope of the formulations possible according to various embodiments; the specific formulation is only an example.

TABLE 2

| | Each Component in Formulation | |
|---|---|---|
| Components in Formulation | a. Amount | b. % by weight |
| GLB TGAI (contains 14 g/L dsRNA) | 57.14 (8.00 g/L dsRNA) | 57.14 (0.8% dsRNA) |
| ATPLUS ® PFA | 5.0 (50 g/L) | 5.0 (5%) |
| EDTA, Tetrasodium Tetrahydrate Salt | 1.583 (1.583 g/L) | 1.583 (1.583%) |
| Propylene glycol | 10.0 (100 g/L) | 10.0 (10%) |
| Dibasic Potassium Phosphate | 0.386 (3.86 g/L) | 0.386 (0.386%) |
| Monobasic Potassium Phosphate | 0.261 (2.61 g/L) | 0.261 (0.261%) |
| Cetrimonium Chloride | 0.25 (2.5 g/L) | 0.25 (0.25%) |
| Antifoam SAG1572 | 0.05 (0.5 g/L) | 0.05 (0.05%) |
| KATHON ® CG/ICP | 0.05 (0.5 g/L) | 0.05 (0.05%) |
| ROCIMA ® BT2S | 0.1 (1.0 g/L) | 0.1 (0.1%) |
| Water | 25.18 (251.8 g/L) | 25.18 (25.18%) |

In addition to the formulation composition listed in Table 2, there are additional formulation compositions that contain alternate components that still provide the same benefit and perform the intended function of each specific co-formulant. Non-limiting, alternate compositions, according to various embodiments, are shown in Tables 3 and 4.

Table 3 provides details of an exemplary formulation, according to various embodiments.

TABLE 3

| | Each Component in Formulation | |
|---|---|---|
| Components in Formulation | a. Amount | b. % by weight |
| GLB TGAI (contains 14 g/L dsRNA) | 57.14 (8.00 g/L dsRNA) | 57.14 (0.8% dsRNA) |
| ATPLUS ® PFA | 5.0 (50 g/L) | 5.0 (5%) |
| EDTA, Tetrasodium Tetrahydrate Salt | 0.950 (9.50 g/L) | 0.950 (0.950%) |
| Propylene glycol | 10.0 (100 g/L) | 10.0 (10%) |
| Dibasic Potassium Phosphate | 0.232 (2.32 g/L) | 0.232 (0.232%) |
| Monobasic Potassium Phosphate | 0.157 (1.57 g/L) | 0.157 (0.157%) |
| Cetrimonium Chloride | 0.25 (2.5 g/L) | 0.25 (0.25%) |
| Antifoam SAG1572 | 0.05 (0.5 g/L) | 0.05 (0.05%) |
| KATHON ® CG/ICP | 0.05 (0.5 g/L) | 0.05 (0.05%) |
| ROCIMA ® BT2S | 0.1 (1.0 g/L) | 0.1 (0.1%) |
| Water | 25.18 (251.8 g/L) | 25.18 (25.18%) |

Table 4 provides details of an exemplary formulation, according to various embodiments.

TABLE 4

| | Each Component in Formulation | |
|---|---|---|
| Components in Formulation | a. Amount | b. % by weight |
| GLB TGAI (contains 14 g/L dsRNA) | 57.14 (8.00 g/L dsRNA) | 57.14 (0.8% dsRNA) |
| ATPLUS ® PFA | 5.0 (50 g/L) | 5.0 (5%) |
| EDTA, Tetrasodium Tetrahydrate Salt | 0.950 (9.50 g/L) | 0.950 (0.950%) |
| Propylene glycol | 10.0 (100 g/L) | 10.0 (10%) |
| Citric Acid Monohydrate | 0.253 (2.53 g/L) | 0.253 (0.253%) |
| Monobasic Sodium Phosphate | 1.744 (17.44 g/L) | 1.744 (1.744%) |
| Cetrimonium Chloride | 0.25 (2.5 g/L) | 0.25 (0.25%) |
| Antifoam SAG1572 ™ | 0.05 (0.5 g/L) | 0.05 (0.05%) |
| KATHON ® CG/ICP | 0.05 (0.5 g/L) | 0.05 (0.05%) |
| ROCIMA ® BT2S | 0.1 (1.0 g/L) | 0.1 (0.1%) |
| Water | 25.18 (251.8 g/L) | 25.18 (25.18%) |

Table 5 provides details of an exemplary formulation, according to various embodiments.

TABLE 5

| Component | Target (wt. %) |
|---|---|
| dsRNA | 0.8 |
| Primary Surfactant* | 5 |
| Ethylenediaminetetraacetic acid (EDTA), Tetrasodium Tetrahydrate Salt | 1.583 |
| Propylene Glycol | 10 |
| Dibasic Potassium Phosphate | 1.869 |
| Monobasic Potassium Phosphate | 1.262 |
| Cetrimonium chloride | 0.25 |
| Dispersant Surfactant* | 1.5 |
| Antifoam* | 0.05 |
| KATHON ® CG/ICP | 0.05 |
| ROCIMA ® BT2S | 0.1 |
| Water | q.s. |

According to various embodiments a formulation exhibiting excellent chemical and physical stability of dsRNA or single stranded RNA may include a combination of broad-spectrum biological preservatives, such as, a combination of BIT, MIT, and CMIT, which may ensure RNA stability in solution over time, under different environmental conditions, and after exposure to common bacterial and fungal contaminants. The formulation exhibiting excellent chemical and physical stability of dsRNA or single stranded RNA may further include a cationic/zwitterionic secondary surfactant, which has been identified in the bacterial challenger studies provided in the examples herein as having the positive impact and anti-microbial activity a cationic surfactant has in formulation, and the prevention of dsRNA or single stranded RNA degradation. The formulation exhibiting excellent chemical and physical stability of dsRNA or single stranded RNA may further include a metal-ion chelator, such as EDTA inhibit nuclease activity. Nuclease activity is a significant challenge to RNA stability over time, under various environmental conditions, and after bacterial or fungal contamination. The inclusion of a metal-ion chelator, exemplified by EDTA, is helpful to inhibit nuclease activity by sequestering divalent cations necessary for enzymatic nuclease activity. A minimum concentration of EDTA, in relation to the current TGAI concentration was determined for dsRNA stability for practical application as detailed in the examples provided herein. The formulation exhibiting excellent chemical and physical stability of dsRNA or single stranded RNA may further include a lignosulfonate, or polymeric conjugated aromatic surfactant to prevent RNA degradation due to UV radiation. This protection from RNA degradation due to UV radiation translates into increased bio-efficacy after application and post exposure. The formulation exhibiting excellent chemical and physical stability of dsRNA may further include a primary surfactant to stabilize a formulation containing dsRNA and a cationic surfactant. The primary surfactant may help to prevent complexation of dsRNA with the cationic surfactant and to provide stability to the formulated product. The formulation exhibiting excellent chemical and physical stability of RNA may further include a buffer to prevent acid/base hydrolysis of dsRNA over various storage conditions. It has also been shown in the examples provided herein that an optimized concentration of the buffer may help to maintain stability of dsRNA in the concentrated product, and upon dilution, specifically in high ionic strength conditions.

The formulation compositions detailed according to various embodiments have shown superior chemical and physical stability attributes to stabilize dsRNA or single stranded RNA as a shelf-stable formulation, as detailed and tested in the examples provided herein. The formulation matrix has shown very good compatibility with dsRNA producing a repeatable SL type formulation with complete solubilization of all individual components. The formulation composition contains several co-formulants and excipients that work together to impart excellent physical and chemical stability to dsRNA, both in the concentrated product, and upon dilution for the intended application. Upon dilution at 100× these formulations are shown to be stable across a variety of water types and hardness from DI water to 1000 ppm calcium/magnesium water. For most of the water varieties these formulations are shown to be clear solutions and demonstrate what is described as micellar solubilization, whereas the samples in 1000 ppm water demonstrate a stable nanoparticle precipitate that is within the 300-600 nm range. These formulations have also been stored at various temperature conditions including −10° C., 4° C., room temperature, 40° C., 54° C., and retain their physical and chemical stability across the varied environmental conditions. After storage at the various conditions they have been analyzed via HPLC for dsRNA stability and to determine a degradation profile if possible. This HPLC analysis is known to have a variability of about +/−10% and the samples after storage compared to the initial concentration within this known variability indicating dsRNA stability in these formulations. The pH of each formulation before and after storage was also measured and demonstrates no considerable change indicating chemical and physical stability after the various storage conditions. The exemplified formulation contains ATPLUS® PFA as a nonionic surfactant to aid stability and solubilization of the dsRNA and co-formulants in the existing formulation matrix both in the concentrated solution and upon dilution in water. The exemplified formulation also contains a comprehensive preservative package that demonstrates protection of dsRNA from bacterial and fungal biocontamination. The results of this study show that the selected formulation matrix can degrade and destroy several common bacteria and fungi once exposed to this contamination and provide extended stability after bacterial and fungal contamination. Many bacteria and fungi can feed off biopolymers like dsRNA, which promote bacterial and fungal growth and dsRNA degradation. In order to prevent this two-fold degradation the preservative components of the formulation must be able withstand biocontamination and protect dsRNA from degradation, and the present study demonstrates that this is achieved for the selected formulations. The formulations according to various embodiments demonstrate acceptable levels of physical and chemical stability, pass certain regulatory testing designated for soluble liquid concentrate type formulations with agricultural applications, and have a robust design capable of protecting the active ingredient dsRNA for over 2 years in shelf storage. Without the ability to provide a dsRNA formulation that demonstrates physical and chemical stability as a practical application, there is no formulation to exogenously deliver dsRNA as part of a pest or pathogen management program. The formulation composition described within this disclosure addresses multiple challenges to dsRNA stability in solution as a practical application and enables the use of dsRNA for commercial application in agricultural pest programs.

Various embodiments provide compositions and formulations that may provide chemical and physical stability to RNA to enable practical application of dsRNA or single stranded RNA in agricultural pest management programs. The individual formulation components were selected to provide a benefit to stability of a dsRNA formulation, to include chemical stability, and physical stability both in the concentrated product and upon dilution during application. Many of these components interact with each other and have optimized ratios for stability. Other specified components have alternate components that offer similar performance, while other components have concentration ranges or alternate components have not been explored.

The development of a soluble liquid concentrate type formulation containing dsRNA or single stranded RNA for practical application as a foliar applied agricultural product, that is stable in solution and upon dilution for application, and resistant to chemical degradation due to time, storage conditions, or contamination.

EXAMPLES

Introduction

The following examples are put forth to provide those of ordinary skill in the art with a complete disclosure and description of how to perform the methods, how to make, and how to use the compositions and compounds disclosed and claimed herein. Efforts have been made to ensure accuracy with respect to numbers (e.g., amounts, temperature, etc.), but some errors and deviations should be accounted for. The purpose of the following examples is not to limit the scope of the various embodiments, but merely to provide examples illustrating specific embodiments.

Formulation Methods

Each probe formulation is produced via low-shear and simple mixing according to the protocol exemplified in the following example. Although the example provides specific details for amounts and types of components and procedures, those having ordinary skill in the art will readily appreciate a wide range of variations suggested by the specific formulation method demonstrated.

Example 1

The formulations according to various embodiments were prepared via low-shear and simple mixing according to the following protocol:

Pre-tare the reactor vessel so that appropriate weights/volumes can be added and checked during production.

To the vessel add an appropriate weight of dsRNA material to reach a final concentration of 8 g/kg dsRNA, or 0.8% dsRNA.

Lower 3-propellar blade equipped in overhead mixer unit into the vessel containing dsRNA and stir at low shear, using minimum speed required to generate a gentle vortex in solution, approximately 450 RPM. Maintain stirring with a gentle vortex throughout the rest of additions to the vessel increasing RPM as necessary, but at a minimum to avoid shearing dsRNA.

To the vessel add biological preservatives, for example, 0.1% of ROCIMA® BT2S, and 0.05% of KATHON® CG/ICP. Stir until fully mixed at 450 RPM, approximately 1 minutes.

To the vessel add an antifreeze agent, for example, 10% of propylene glycol. Stir this mixture at 500 RPM until a resultant solution is a clear, yellow solution, approximately 2 minutes.

To the vessel add a metal-ion sequestrant, for example, 1.583% EDTA while stirring at 500 RPM.

To the vessel add a buffer, for example, 12.10% of the 2 M Potassium Phosphate Buffer pH 7 solution. Upon addition of Buffer and EDTA solution the formulation should turn slightly cloudy but will return to a clear solution after several minutes of stirring. Approximately 5 minutes at 600 RPM.

To the vessel add 0.05% of an antifoam agent. As detailed in later examples a variety of antifoam agents were tested. Stir until fully mixed at 600 RPM to result in a slightly turbid, yellowish solution, approximately 2 minutes.

To the vessel add 5% of a primary surfactant and increase RPM slowly to 900 RPM. As detailed in later examples, a variety of primary surfactants were tested.

To the vessel add a secondary surfactant, for example, up to 0.25% of cetrimonium chloride, or up to 1% lauryl betaine. Upon immediate addition of cetrimonium chloride or lauryl betaine, slight, localized concentrations of precipitation can be observed but should rapidly be solubilized into solution. Continue stirring solution until all material is fully solubilized and the resultant solution is slightly turbid and slightly yellow, approximately 2 minutes at 900 RPM. If a quaternary ammonium compound (for example, ATPLUS® PFA) is added as the primary surfactant without the presence of a secondary surfactant, the quaternary ammonium compound may interact with RNA resulting in immediate instability of the dsRNA in the formulation.

To the vessel add up to 1.5% of a UV protectant (also known as a dispersant surfactant) and let stir at 900 RPM for 2 minutes.

To the vessel add the appropriate weight percent water to reach the target formulation weight. Stir until fully mixed into solution at 500 RPM, approximately 1 minute.

This sample is then mixed via low shear until each component is fully incorporated and the resultant liquid should be a translucent, slightly turbid, slightly yellowish liquid, with low viscosity. If a naphthalene sulfonate condensate, or lignosulfonate is used as an optional UV protectant (also known as a dispersant surfactant), the resultant liquid will be a dark brown liquid with low viscosity.

The method described herein or any others known in the art can be used for making compositions of the present disclosure using various components at various concentrations.

Examples 2-6: Formulation Compatibility

These examples demonstrate the importance of the primary surfactant, and according to various embodiments, the buffer as well. Formulation compatibility is characterized by a physical observation. As a soluble liquid concentrate type formulation, all components should be freely solubilized in water, and any precipitation, agglomerations, phase separation, or miscibility issues are an indication that the formulation components are not compatible. In general, the formulations according to various embodiments have been identified to have no compatibility issues and to produce fine solubilized formulations with low viscosity. The formulations are primarily translucent although in some instances are slightly turbid, clear to yellowish solutions.

For purposes of these examples, ATPLUS® PFA was used as the primary surfactant and was determined to be stable between concentration ranges of 4-6% weight. Adjusting the concentration of the primary surfactant above or below these specified ranges was demonstrated to result in significant amounts of precipitation in the concentrated product, in the compositions with the components at the listed concentrations in these examples.

The formulation compositions according to various embodiments may include a buffer, such as a phosphate buffer at or about pH 7, or in another embodiment a citrate buffer at or about pH 6. For purposes of these examples, and elsewhere in the specification, the term "phosphate buffer" refers to a buffer comprising a specific ratio of monobasic potassium phosphate and dibasic potassium phosphate. More specifically, a 0.1 to 1.1 mass ratio of monobasic potassium phosphate to dibasic potassium phosphate covers a pH range from 6.5 to 7.5. According to various embodiments, when stored above refrigerated temperatures or where storage temperatures will fluctuate significantly, addition of a buffer is important to the formulation to maintain a pH stable system in prevention of acid/base hydrolysis over time, as well as during storage under different temperature conditions. In addition to this stability benefit for the prevention of acid/base hydrolysis, the buffer system provides a specific stability benefit in maintaining solubility of an electrolyte-based system. Absence of, or reduction of the Molar amount of phosphate buffer may result in precipitation of the concentrated formulation.

Example 2

FIGS. 1A, 1B, 1C, and 1D are examples according to various embodiments, illustrating photographs of a compatible formulation after storage for 2 weeks at −10° C., and 2 and 8 weeks at 4° C., 8 weeks at 40° C., 2 weeks at 54° C.

The formulation shown in FIGS. 1A, 1B, 1C, and 1D was prepared according to the method described in Example 1 and had the composition according to Table 6.

TABLE 6

| Component | Target (wt. %) |
|---|---|
| dsRNA | 0.8 |
| ATPLUS ® PFA | 5 |
| Ethylenediaminetetraacetic acid (EDTA), Tetrasodium Tetrahydrate Salt | 1.583 |
| Propylene Glycol | 10 |
| Dibasic Potassium Phosphate | 1.869 |
| Monobasic Potassium Phosphate | 1.262 |
| Cetrimonium chloride | 0.25 |
| SAG1572* | 0.05 |
| KATHON ® CG/ICP | 0.05 |
| ROCIMA ® BT2S | 0.1 |
| Water | q.s. |

As stated above, the primary surfactant in the formulation samples shown in FIGS. 1A, 1B, 1C, and 1D was ATPLUS® PFA, an EO:PO modified alcohol ethoxylate type surfactant, at a use rate of 5% by weight in the formulation. The stability and compatibility of formulations containing dsRNA is sensitive to changes in surfactant chemistry, and concentration range within the formulation. Testing was performed using various concentrations of ATPLUS® PFA, and these particular formulations were found to be stable at 5%, by weight

Example 3

This example demonstrates a formulation with a failure in compatibility and stability with a varied concentration of primary surfactant, specifically ATPLUS® PFA.

Figure 2A:
FIGS. 2A and 2B are examples according to various embodiments, illustrating photographs of formulations with ATPLUS® PFA concentration at 10% and 5% by weight respectively.
Figure 2B:
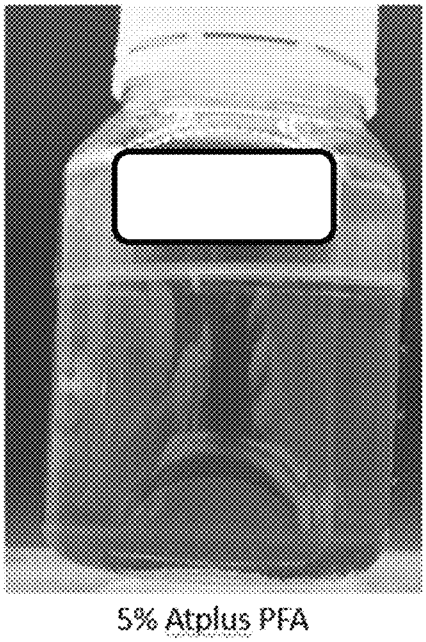
Figures 3A, 3B, 3C, 3D:
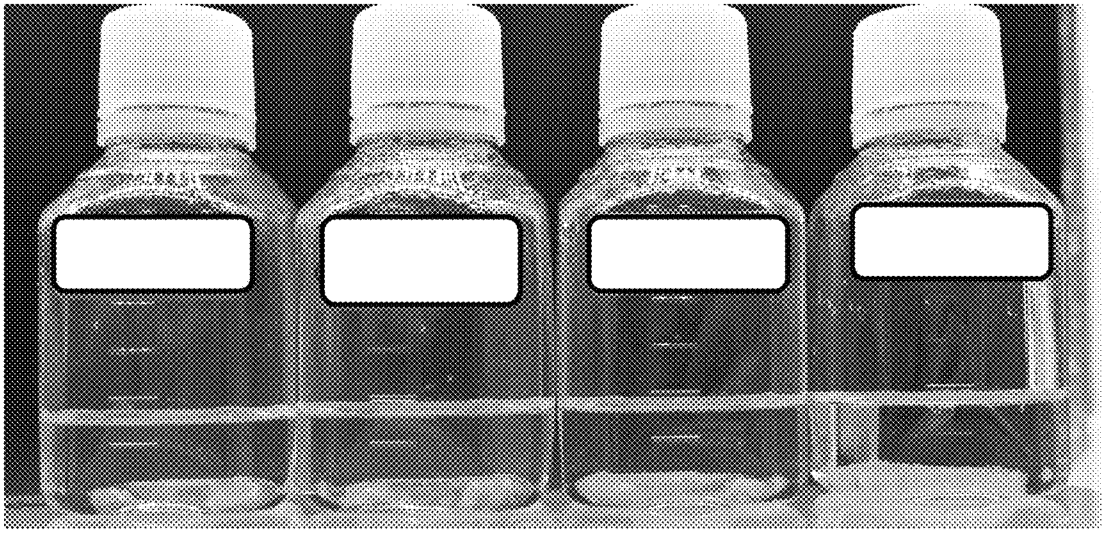
FIGS. 3A, 3B, 3C, and 3D are examples according to various embodiments, illustrating photographs of formulations with ATPLUS® PFA concentration at 5% 4.5%, 4.0%, and 3.5% by weight respectively.

FIGS. 2A and 2B are examples according to various embodiments, illustrating photographs of formulations with ATPLUS® PFA concentration at 10% and 5% by weight, respectively, after storage at 54° C. At a concentration of 10% ATPLUS® PFA, a clearly visible precipitate forms in formulations containing dsRNA. Formulations containing 5% ATPLUS® PFA have been found to be stable, without signs of significant precipitation. Similar results were demonstrated in storage conditions ranging from −10° C. to 54° C.

The formulations shown were prepared according to the method described in Example 1 and had the compositions according to Table 7.

TABLE 7

| Component | TFORM190903_ WS_05 Target (wt. %) | TFORM190903_ WS_07 Target (wt. %) |
|---|---|---|
| dsRNA | 0.8 | 0.8 |
| ATPLUS ® PFA | 10 | 5 |
| Ethylenediaminetetraacetic acid (EDTA), Tetrasodium Tetrahydrate Salt | 0.313 | 0.313 |
| Propylene Glycol | 10 | 10 |
| Dibasic Potassium Phosphate | 0.772 | 0.772 |
| Monobasic Potassium Phosphate | 0.521 | 0.521 |
| Cetrimonium chloride | 0.25 | 0.25 |
| SAG1572* | 0.05 | 0.05 |
| KATHON ® CG/ICP | 0.05 | 0.05 |
| ROCIMA ® BT2S | 0.1 | 0.1 |
| Water | q.s. | q.s. |

Example 4

This example further demonstrates a formulation with a failure in compatibility and stability with a varied concentration of primary surfactant, specifically ATPLUS® PFA.

FIGS. 3A, 3B, 3C, and 3D are an examples according to various embodiments, illustrating photographs of formulations with ATPLUS® PFA concentration at 5% 4.5%, 4.0%, and 3.5% by weight respectively. No precipitate was observed at 5% concentration of ATPLUS® PFA and a small amount of visible precipitate, within acceptable limits, was observed in formulations with concentrations of ATPLUS® PFA below 5% in these tested compositions.

The formulations shown were prepared according to the method described in Example 1 and had the compositions according to Table 8.

TABLE 8

| Component | TFORM190909_BG_1 Target (wt. %) | TFORM190909_BG_2 Target (wt. %) | TFORM190909_BG_3 Target (wt. %) | TFORM190909_BG_4 Target (wt. %) |
|---|---|---|---|---|
| dsRNA | 0.8 | 0.8 | 0.8 | 0.8 |
| ATPLUS ® PFA | 5 | 4.5 | 4 | 3.5 |
| Ethylene-diaminetetra-acetic acid (EDTA), Tetrasodium Tetrahydrate Salt | 0.156 | 0.156 | 0.156 | 0.156 |
| Propylene Glycol | 10 | 10 | 10 | 10 |
| Dibasic Potassium Phosphate | 0.386 | 0.386 | 0.386 | 0.386 |
| Monobasic Potassium Phosphate | 0.261 | 0.261 | 0.261 | 0.261 |
| Cetrimonium chloride | 0.25 | 0.25 | 0.25 | 0.25 |
| SAG1572* | 0.05 | 0.05 | 0.05 | 0.05 |
| KATHON ® CG/ICP | 0.05 | 0.05 | 0.05 | 0.05 |
| ROCIMA ® BT2S | 0.1 | 0.1 | 0.1 | 0.1 |
| Water | q.s. | q.s. | q.s. | q.s. |

Example 5

Figure 4:
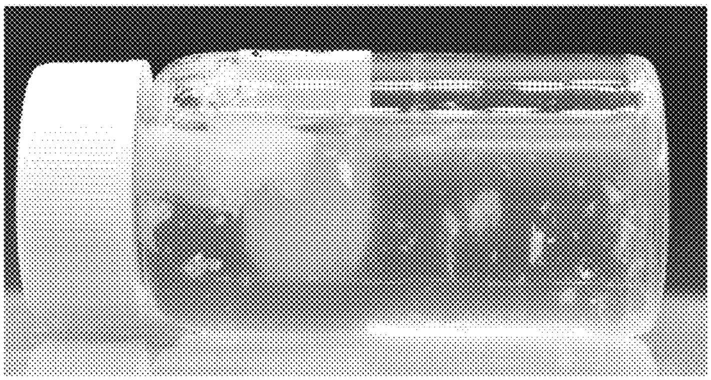
FIG. 4 is an example according to various embodiments, illustrating a photograph of a formulation without a phosphate buffer, showing significant precipitation of dsRNA.

This example demonstrates a failure in stability contributed to by the lack of a metal ion sequenstrant and lack of buffer in the formulation composition of Table 9. FIG. 4 illustrates a photograph of this formulation without a metal ion sequestrant and showing showing significant precipitation of dsRNA. The formulation shown was prepared according to the method described in Example 1 and had the composition according to Table 9.

TABLE 9

| Component | TFORM190926_BG_01 Target (wt. %) |
|---|---|
| dsRNA | 0.8 |
| ATPLUS ® PFA | 5 |
| Ethylenediaminetetraacetic acid (EDTA), Tetrasodium Tetrahydrate Salt | 0 |
| Propylene Glycol | 10 |
| Dibasic Potassium Phosphate | 0 |
| Monobasic Potassium Phosphate | 0 |
| Cetrimonium chloride | 0.25 |
| SAG1572* | 0.05 |
| KATHON ® CG/ICP | 0.05 |
| ROCIMA ® BT2S | 0.1 |
| Water | q.s. |

Example 6

This example demonstrates lower stability due to the concentration of buffer in the formulation compositions and concentrations of EDTA.

Figures 5A, 5B, 5C, 5D, 5E:
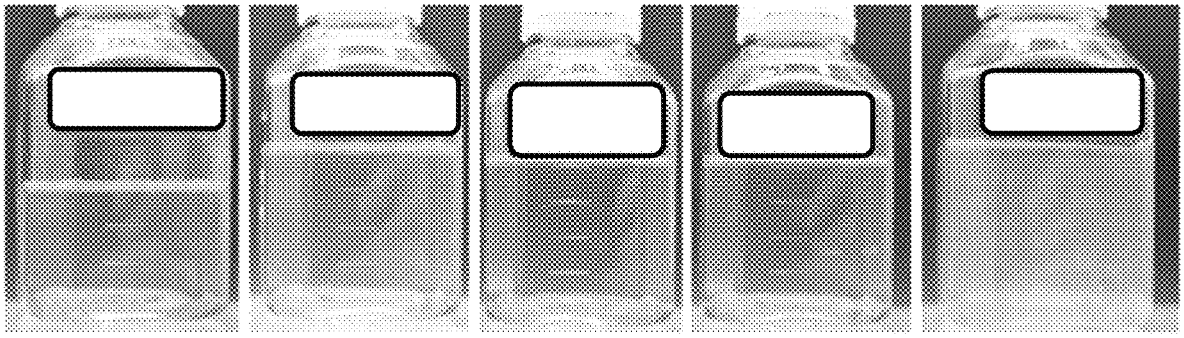
FIGS. 5A, 5B, 5C, 5D, and 5E are examples according to various embodiments, illustrating photographs of formulations with 242 mM, 200 mM, 150 mM, 100 mM, and 50 mM concentrations of phosphate buffer, respectively, showing visible precipitation in FIGS. 5C, 5D, and 5E.
Figures 7A, 7B, 7C, 7D:
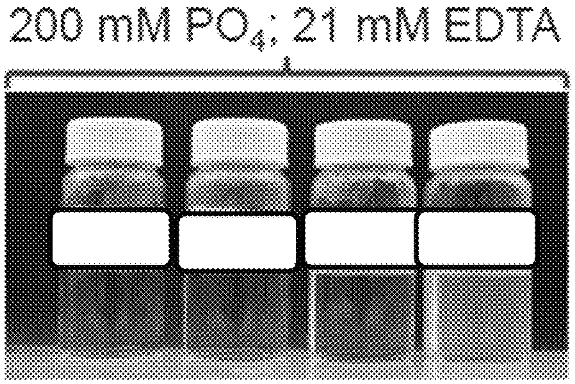
FIGS. 7A, 7B, 7C, and 7D are examples according to various embodiments, illustrating photographs of a formulation comprising 200 mM of phosphate buffer and 21 mM EDTA, diluted into water at 35 ppm, 342 ppm, 500 ppm, and 1000 ppm, respectively, the photographs being taken 24 hours after the dilution into water.
Figures 7E, 7F, 7G, 7H:
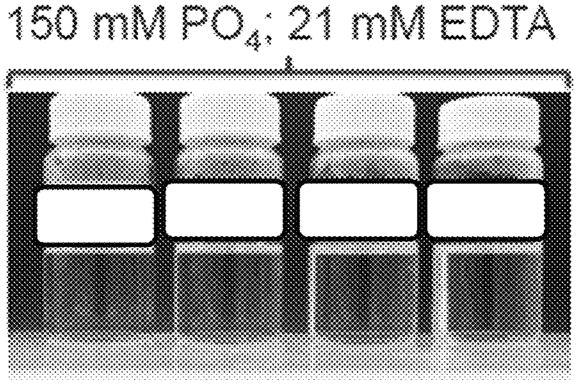
FIGS. 7E, 7F, 7G, and 7H are examples according to various embodiments, illustrating photographs of a formulation comprising 150 mM of phosphate buffer and 21 mM EDTA, diluted into water at 35 ppm, 342 ppm, 500 ppm, and 1000 ppm, respectively, the photographs being taken 24 hours after the dilution into water.
Figures 7I, 7J, 7K, 7L:
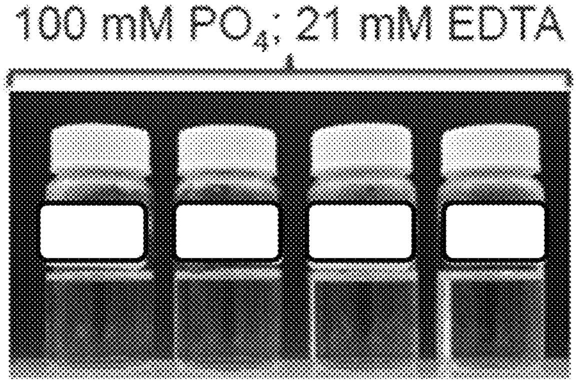
FIGS. 7I, 7J, 7K, and 7L are examples according to various embodiments, illustrating photographs of a formulation comprising 100 mM of phosphate buffer and 21 mM EDTA, diluted into water at 35 ppm, 342 ppm, 500 ppm, and 1000 ppm, respectively, the photographs being taken 24 hours after the dilution into water.
Figures 7M, 7N, 7O, 7P:
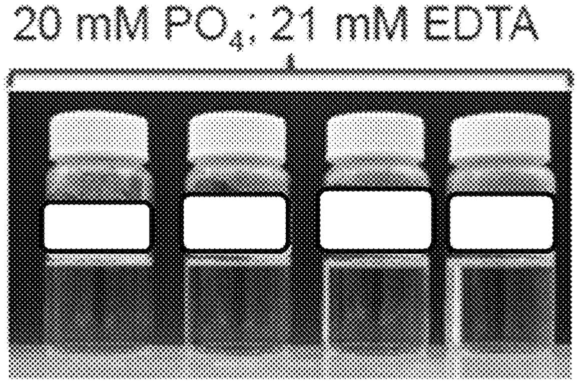
FIGS. 7M, 7N, 7O, and 7P are examples according to various embodiments, illustrating photographs of a formulation comprising 20 mM of phosphate buffer and 21 mM EDTA, diluted into water at 35 ppm, 342 ppm, 500 ppm, and 1000 ppm, respectively, the photographs being taken 24 hours after the dilution into water.
Figures 8A, 8B, 8C, 8D:
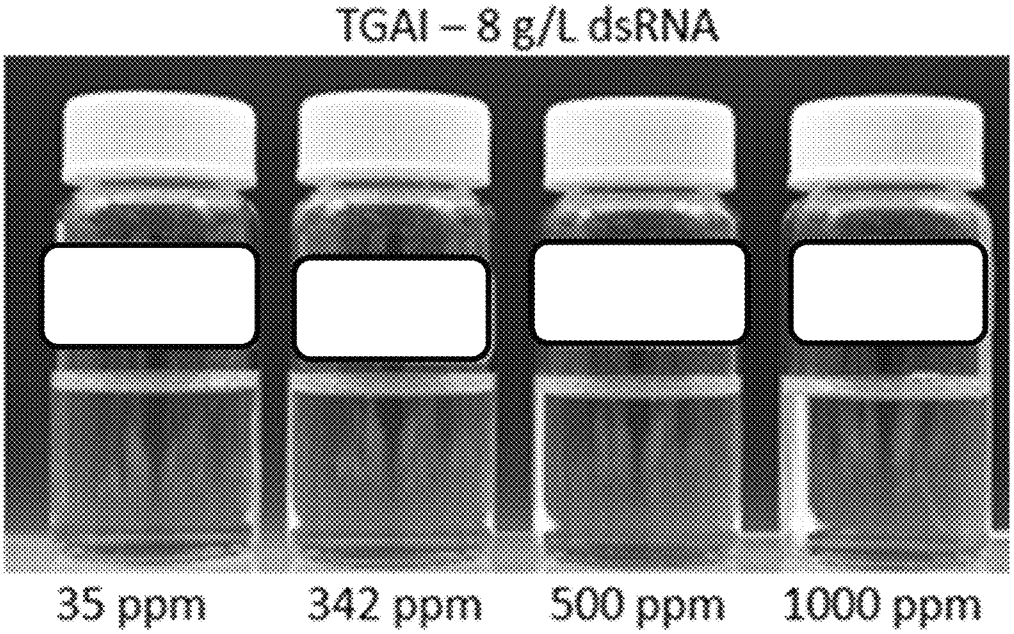
FIGS. 8A, 8B, 8C, and 8D are examples according to various embodiments, illustrating photographs of a formulation comprising 8 g/L of dsRNA, diluted into water at 35 ppm, 342 ppm, 500 ppm, and 1000 ppm, respectively, the photographs being taken 24 hours after the dilution into water.
Figures 8E, 8F, 8G, 8H:
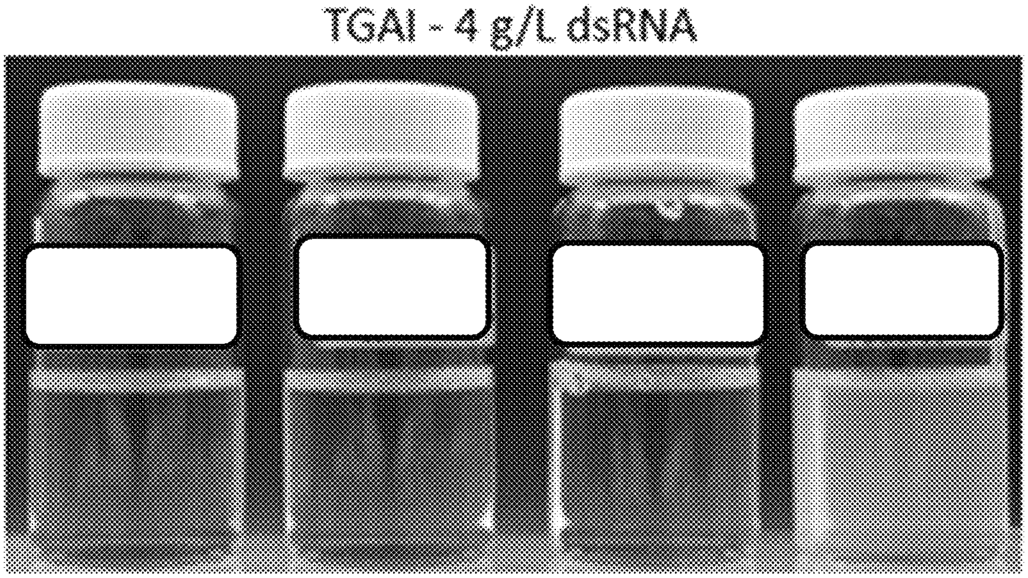
FIGS. 8E, 8F, 8G, and 8H are examples according to various embodiments, illustrating photographs of a formulation comprising 4 g/L of dsRNA, diluted into water at 35 ppm, 342 ppm, 500 ppm, and 1000 ppm, respectively, the photographs being taken 24 hours after the dilution into water.

FIGS. 5A, 5B, 5C, 5D, and 5E are examples according to various embodiments, illustrating photographs of formulations with 242 mM, 200 mM, 150 mM, 100 mM, and 50 mM concentrations of phosphate buffer, respectively, showing a limited amount of visible precipitation, though within acceptable limits, in FIGS. 5C, 5D, and 5E, where the phosphate buffer concentration and EDTA concentration has been significantly reduced.

The formulations shown were prepared according to the method described in Example 1 and had the compositions according to Table 10.

TABLE 10

| Component | TFORM190919_BG_01 Target (wt. %) | TFORM190919_BG_02 Target (wt. %) | TFORM190919_BG_03 Target (wt. %) | TFORM190919_BG_04 Target (wt. %) | TFORM190919_BG_06 Target (wt. %) |
|---|---|---|---|---|---|
| dsRNA | 0.8 | 0.8 | 0.8 | 0.8 | 0.8 |
| ATPLUS ® PFA | 5 | 5 | 5 | 5 | 5 |
| Ethylene-diamine-tetraacetic acid (EDTA), Tetrasodium Tetrahydrate Salt | 0.625 | 0.568 | 0.517 | 0.439 | 0.258 |
| Propylene Glycol | 10 | 10 | 10 | 10 | 10 |
| Dibasic Potassium Phosphate | 1.869 | 1.699 | 1.545 | 1.313 | 0.772 |
| Monobasic Potassium Phosphate | 1.262 | 1.147 | 1.043 | 0.887 | 0.521 |
| Cetrimonium chloride | 0.25 | 0.25 | 0.25 | 0.25 | 0.25 |
| SAG1572* | 0.05 | 0.05 | 0.05 | 0.05 | 0.05 |
| KATHON ® CG/ICP | 0.05 | 0.05 | 0.05 | 0.05 | 0.05 |
| ROCIMA ® BT2S | 0.1 | 0.1 | 0.1 | 0.1 | 0.1 |
| Water | q.s. | q.s. | q.s. | q.s. | q.s. |

Examples 7-9: Particle Size and Water Hardness Stability

Particle size measurements are an important physical parameter and are used to determine whether the formulation containing dsRNA is stable upon dilution. To determine whether a formulation is stable the sample is diluted at the spray application rate in CIPAC standard waters identified by CIPAC MT 18 as 35 ppm water, 342 ppm water, 500 ppm, and 1000 ppm water, and is roughly composed of a 4:1 $Mg^{2+}$:$Ca^{2+}$ ionic solution. Upon dilution the sample is left to sit for 24 hours to observe any physical instabilities, and the particle size is then collected via DLS measurement using a Malvern Zetasizer NanoDS, or other suitable DLS instrument. Physical stability testing has determined an optimum ratio between dsRNA supplied as technical grade active ingredient (TGAI) and the buffer systems, specifically when diluted in water with high ionic content.

Example 7

The selected formulation probe was diluted into water at a concentration equivalent to the maximum field use rate using a 20 gallon per acre application volume. Each water condition tested were prepared according to the CIPAC MT 18 standard method. Particle size measurements and physical observations were taken for samples immediately after dilution, and after 24 hours. The results for a successful formulation is shown in this Example, demonstrating the visual appearance and the median particle size via DLS.

TABLE 11

| Sample ID | Time (hrs) | Z-Ave (d.nm) | PdI | Count Rate (kcps) |
|---|---|---|---|---|
| TForm191024_BG_3 | 0 | 310.7 | 0.456 | 27.3 |
| TForm191024_BG_3 | 24 | 330.2 | 0.21 | 179.5 |

Table 11 shows particle size, polydispersity and count rate as measured by Dynamic Light Scattering for selected formulation dilutions in various water conditions. Low count rate and Z-Average particle size of 310-330 nm indicates that the formulation after dilution has very low concentration of particles and is stable in solution at room temperature.

FIGS. 6A, 6B, 6C, 6D are examples according to various embodiments, illustrating photographs of a formulation diluted into water at 35 ppm, 342 ppm, 500 ppm, and 1000 ppm, respectively, the photographs being taken immediately after the dilution into water. FIGS. 6E, 6F, 6G, and 6H are examples according to various embodiments, illustrating photographs of a formulation diluted into water at 35 ppm, 342 ppm, 500 ppm, and 1000 ppm, respectively, the photographs being taken 24 hours after the dilution into water.

The formulation shown were prepared according to the method described in Example 1 and had the composition according to Table 12.

TABLE 12

| Component | TFORM191024_BG_3 Target (wt. %) |
|---|---|
| dsRNA | 0.8 |
| ATPLUS ® PFA | 5 |
| Ethylenediaminetetraacetic acid (EDTA), Tetrasodium Tetrahydrate Salt | 1.583 |
| Propylene Glycol | 10 |
| Dibasic Potassium Phosphate | 1.869 |
| Monobasic Potassium Phosphate | 1.262 |
| Cetrimonium chloride | 0.25 |
| SAG 1572* | 0.05 |
| KATHON ® CG/ICP | 0.05 |
| ROCIMA ® BT2S | 0.1 |
| Water | q.s. |

Example 8

An additional aspect to formulation stability upon dilution is the ratio of phosphate buffer to the TGAI concentration. Evidence has shown that maximizing the ratio between buffer concentration and the TGAI input source results in greater stability to the formulation upon dilution in high ionic strength (hard) waters. This impact in stability upon dilution in high ionic strength water is counter to the stability of the concentrated formulation, which is demonstrates greater stability as the ratio of buffer to TGAI is minimized. The optimized ratio (Greater than 0.2 mass ratio TGAI to buffer composition) between buffer and TGAI has been selected for the exemplified composition, providing stability in the concentrated formulation, and upon dilution in various ionic strength waters.

FIGS. 7A, 7B, 7C, and 7D are examples according to various embodiments, illustrating photographs of a formulation comprising 200 mM of phosphate buffer and 21 mM EDTA, diluted into water at 35 ppm, 342 ppm, 500 ppm, and 1000 ppm, respectively, the photographs being taken 24 hours after the dilution into water. FIGS. 7E, 7F, 7G, and 7H are examples according to various embodiments, illustrating photographs of a formulation comprising 150 mM of phosphate buffer and 21 mM EDTA, diluted into water at 35 ppm, 342 ppm, 500 ppm, and 1000 ppm, respectively, the photographs being taken 24 hours after the dilution into water. FIGS. 7I, 7J, 7K, and 7L are examples according to various embodiments, illustrating photographs of a formulation comprising 100 mM of phosphate buffer and 21 mM EDTA, diluted into water at 35 ppm, 342 ppm, 500 ppm, and 1000 ppm, respectively, the photographs being taken 24 hours after the dilution into water. FIGS. 7M, 7N, 7O, and 7P are examples according to various embodiments, illustrating photographs of a formulation comprising 20 mM of phosphate buffer and 21 mM EDTA, diluted into water at 35 ppm, 342 ppm, 500 ppm, and 1000 ppm, respectively, the photographs being taken 24 hours after the dilution into water.

As can be seen, decreasing concentration of phosphate buffer, and increasing ratio between TGAI and buffer results in better solution stability in high ionic strength waters. This is indicated by the disappearance of the precipitation in 1000 ppm waters after 24 hours when viewing the samples from left to right.

The formulations shown were prepared according to the method described in Example 1 and had the compositions according to Table 13.

TABLE 13

| Component | TFORM190829_ BG_01 Target (wt. %) | TFORM190829_ BG_02 Target (wt. %) | TFORM190829_ BG_03 Target (wt. %) | TFORM190829_ BG_04 Target (wt. %) |
|---|---|---|---|---|
| dsRNA | 0.4 | 0.4 | 0.4 | 0.4 |
| ATPLUS ® PFA | 10 | 10 | 10 | 10 |
| Ethylene-diamine-tetraacetic acid (EDTA), Tetrasodium Tetrahydrate Salt | 0.625 | 0.625 | 0.400 | 0.125 |
| Propylene Glycol | 10 | 10 | 10 | 10 |
| Dibasic Potassium Phosphate | 1.544 | 1.158 | 0.772 | 0.154 |

TABLE 13-continued

| Component | TFORM190829_ BG_01 Target (wt. %) | TFORM190829_ BG_02 Target (wt. %) | TFORM190829_ BG_03 Target (wt. %) | TFORM190829_ BG_04 Target (wt. %) |
|---|---|---|---|---|
| Monobasic Potassium Phosphate | 1.043 | 0.782 | 0.521 | 0.104 |
| Cetrimonium chloride | 0.25 | 0.25 | 0.25 | 0.25 |
| SAG 1572* | 0.05 | 0.05 | 0.05 | 0.05 |
| KATHON ® CG/ICP | 0.05 | 0.05 | 0.05 | 0.05 |
| ROCIMA ® BT2S | 0.1 | 0.1 | 0.1 | 0.1 |
| Water | q.s. | q.s. | q.s. | q.s. |

Example 9

This example provides observations on impacts to stability of the formulation upon dilution in high ionic strength water, with respect to the ratio of TGAI to buffer at a dsRNA concentration of 4 g/L. As the dsRNA concentration is doubled in the current composition to 8 g/L, the TGAI input concentration is also doubled, roughly. As a result of this increase in the input TGAI, the ratio between buffer and TGAI is also increased as a result, with an improvement between otherwise equivalent formulation compositions. This example between corresponding TGAI inputs at 4 g/L dsRNA and 8 g/L dsRNA with the same concentration of phosphate buffer is shown in the figure below.

FIGS. 8A, 8B, 8C, and 8D are examples according to various embodiments, illustrating photographs of a formulation comprising 8 g/L of dsRNA, diluted into water at 35 ppm, 342 ppm, 500 ppm, and 1000 ppm, respectively, the photographs being taken 24 hours after the dilution into water. FIGS. 8E, 8F, 8G, and 8H are examples according to various embodiments, illustrating photographs of a formulation comprising 4 g/L of dsRNA, diluted into water at 35 ppm, 342 ppm, 500 ppm, and 1000 ppm, respectively, the photographs being taken 24 hours after the dilution into water. These figures demonstrate differences in solution stability in high ionic strength waters as a result of TGAI to phosphate buffer ratio. Samples having a roughly 2× increase in TGAI to phosphate buffer ratio do not exhibit the same precipitation after 24 hours after dilution in 1000 ppm water.

The formulations shown were prepared according to the method described in Example 1 and had the compositions shown in Table 14.

TABLE 14

| Component | TFORM191024_ BG_3 Target (wt. %) | TFORM191024_ BG_4 Target (wt. %) |
|---|---|---|
| dsRNA | 0.8 | 0.4 |
| ATPLUS ® PFA | 5 | 5 |
| Ethylenediaminetetraacetic acid (EDTA), Tetrasodium Tetrahydrate Salt | 1.583 | 1.583 |
| Propylene Glycol | 10 | 10 |
| Dibasic Potassium Phosphate | 1.869 | 1.869 |
| Monobasic Potassium Phosphate | 1.262 | 1.262 |
| Cetrimonium chloride | 0.25 | 0.25 |
| SAG 1572* | 0.05 | 0.05 |
| KATHON ® CG/ICP | 0.05 | 0.05 |
| ROCIMA ® BT2S | 0.1 | 0.1 |
| Water | q.s. | q.s. |

The importance of the buffer concentration on solution stability upon dilution can be summarized as follows. A general trend was observed to show that increasing the ratio of TGAI to phosphate concentration results in improvement in stability of the product upon dilution if using high ionic strength water. Reduction of phosphate buffer concentration will result in the condition that is a maximized ratio between TGAI and buffer, which is helpful for solution stability upon dilution in high ionic strength water. It is important to note that this impact of the phosphate buffer concentration on stability in solution upon dilution runs counter to the effect of the phosphate buffer concentration on stability in the concentrated product. With these effects in mind, a concentration of 242 mM is "maximized" for stability in the concentrated solution, but also "minimized" for stability in the solution upon dilution in high ionic strength water. Reduction of the phosphate buffer concentration would positively impact stability in solution upon dilution in high ionic strength water, but negatively impact stability in the concentrated solution. Increase of the phosphate buffer concentration would negatively impact stability in solution upon dilution in high ionic strength water, but positively impact stability in the concentrated solution, thus an optimized balance for high ionic strength water, at 242 mM phosphate buffer was selected for stability at both conditions. This impact, and the observations for this general trend are shown in Table 15.

TABLE 15

| Sample Condition | Impact on Stability | |
|---|---|---|
| Phosphate Buffer Concentration | Upon Dilution | Concentrated Solution |
| Minimized | (+) | (−) |
| Maximized | (−) | (+) |

Table 15 demonstrates clarifying effects of phosphate buffer concentration on formulation stability in the concentrated product, and upon dilution in high ionic strength water.

Examples 10-12: Shelf-Life Stability: Physical and Chemical Stability after Storage Shelf-life stability and accelerated storage studies are performed by placing aliquots (50 mL minimum) of each potential formulation into the following environmental conditions: −10° C., 4° C., room temperature, 40° C., 54° C., and freeze/thaw temperature cycling between −10° C. and 40° C. every 24 hours. The samples are stored in these conditions for a minimum of 2 weeks, 8 week for 40° C., prior to analysis, and analysis is determined by physical and chemical stability compared to the initial samples, or an aliquot from the sample stored at 4° C. Chemical stability is determined by quantification by HPLC utilizing a solid phase extraction based HPLC method. Chemical stability is also verified using Ribogreen reagent, a nucleic acid binding reagent, and fluorescence spectroscopy according to the manufacturers protocol. Physical stability is determined by noticing any color changes, precipitation, agglomeration, phase separation, bacterial or fungal growth, changes in pH, changes in turbidity, syneresis or top clearing, and changes in particle size upon dilution.

Formulated dsRNA is shown to be exceptionally stable after accelerated storage conditions, and across temperature ranges of −10° C. to 54° C. Non-formulated dsRNA does not exhibit this same stability to high temperatures and rapidly degrades within 2 week storage at 54° C. Such accelerated storage conditions are frequently used to test for stability at less extreme temperatures over a longer time. For example, 2 weeks at 54° C. is commonly used to represent storage for one year at room temperature. (See United States Environmental Protection Agency Nov. 16, 2012 Memorandum regarding Accelerated Storage Stability and Corrosion Characteristics Study Protocol).

Example 10 (Comparative)

This comparative example demonstrates that non-formulated dsRNA does not exhibit this same stability to high temperatures and rapidly degrades within 2 week storage at 54° C. Table 16 shows chemical degradation of non-formulated dsRNA when stored at elevated temperatures. Notable is the significant degradation profiles seen for unformulated dsRNA stored for 2 weeks at 54° C.

TABLE 16

TGAI Thermal Degradation Analysis

| TGAI Lot | 4° C.-54° C. % Diff | 4° C.-40° C. % Diff |
|---|---|---|
| TGAI190401-01 | 66.5 | 5.0 |
| TGAI190430-01 | 39.1 | 7.2 |
| TGAI190430-02 | 40.0 | 4.1 |
| TGAI190405-02 | 48.0 | 12.1 |
| TGAI190501-01 | 59.7 | 5.1 |
| TGAI190501-02 | 66.2 | 6.7 |

Example 11

Chemical stability of the probe formulations is demonstrated by HPLC analysis prior to and after storage under the listed environmental conditions. The results of this LC analysis are shown in FIG. 9 and in Table 17.

Figure 9:
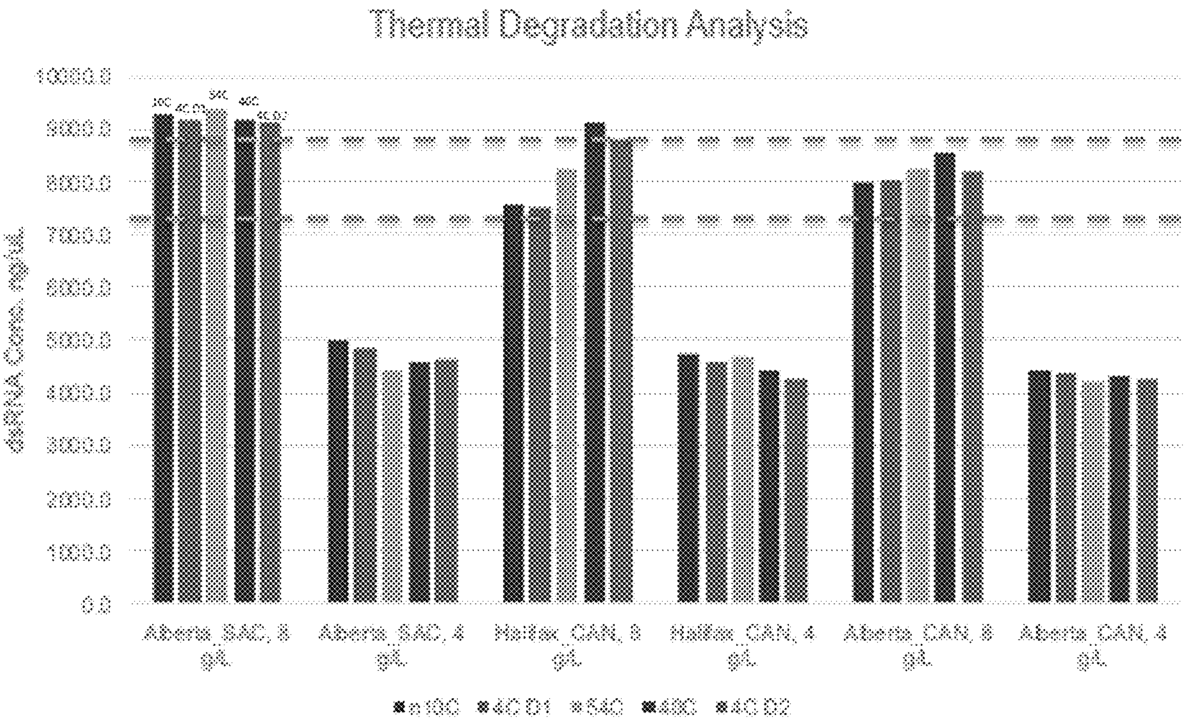
FIG. 9 is an example according to various embodiments, illustrating High Performance Liquid Chromatography (HPLC) results for chemical stability for various formulations after storage at −10° C., 4° C., 40° C., and 54° C.
Figures 10A, 10B, 11A, 11B:
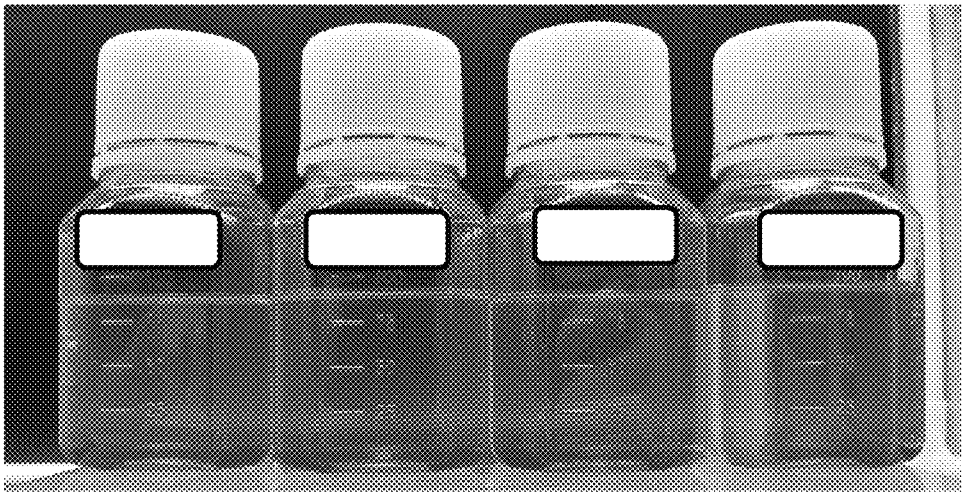
FIGS. 10A, 10B, 11A, and 11B are examples according to various embodiments, illustrating photographs of a compatible formulation comprising SAG 1572™ anti-foam after storage for 2 weeks at −10° C., and 2 and 8 weeks at 4° C., 8 weeks at 40° C., 2 weeks at 54° C., demonstrating excellent dsRNA stability.

FIG. 9 is an example according to various embodiments, illustrating High Performance Liquid Chromatography (HPLC) results for chemical stability for various formulations after storage at −10° C., 4° C., 40° C., and 54° C. Samples collected for formulations containing 8 g/L and 4 g/L dsRNA. No formulations show degradation of dsRNA over the time course tested, 8 weeks at 40° C., 2 weeks at 54° C., 2 weeks at −10° C., and 2 and 8 weeks at 4° C., for accelerated storage conditions. Thus the results show that all formulations tested remain stable at room temperature for at least one year.

The formulations shown were prepared according to the method described in Example 1 and had the composition according to Table 22.

Table 17 shows data demonstrating the chemical stability of dsRNA via HPLC after the above-mentioned storage conditions. As set forth in this Table, HPLC measurements of dsRNA indicated less than 10% dsRNA degradation in the formulated samples, compared to unformulated dsRNA in table 16 which showed much higher rates of degradation. These measurements for the formulated compositions are within the expected 10% variation in HPLC measurements indicating no to minimal dsRNA degradation.

TABLE 17

Thermal Degradation Analysis

| Sample ID | 4 C.-40 C. % Diff | 4 C.-54 C. % Diff | 4 C.-(−10) C. % Diff |
|---|---|---|---|
| TForm191024_BG_1 | 0.7 | 2.6 | 1.5 |
| TForm191024_BG_2 | 1.1 | 7.7 | 3.5 |
| TForm191024_BG_3 | 3.4 | 9.3 | 0.3 |
| TForm191024_BG_4 | 2.9 | 2.4 | 3.5 |
| TForm191024_BG_5 | 0 | 2.6 | 0.3 |
| TForm191024_BG_6 | 1.7 | 4 | 1.3 |

Example 12

Formulated samples were also evaluated for any changes in pH after storage and these results are shown in Table 18. Changes in pH are indicative of physical or chemical instability and are not exhibited by the exemplified formulation composition.

TABLE 18

| Sample ID | Conc. | Initial pH | 2 Week 54 C. pH | 8 Week 40 C. pH |
|---|---|---|---|---|
| TForm191024_BG_1 | 8 g/L | 7.11 | 7.11 | 7.12 |
| Tform191024_BG_3 | 8 g/L | 7.11 | 7.12 | 7.13 |
| Tform191024_BG_5 | 8 g/L | 7.11 | 7.11 | 7.13 |

Table 18 shows data for pH stability of formulated dsRNA after accelerated storage conditions. No significant change in pH after various storage conditions is observed from the initial sampling condition. Indication of physical and chemical stability, and prevention of possible acid/base hydrolysis of dsRNA during storage in a formulation.

The formulations described above were prepared according to the method described in Example 1 and had the compositions according to Table 19.

TABLE 19

| Component | TFORM191024_ BG_1, _3, _5 Target (wt. %) |
|---|---|
| dsRNA | 0.8 |
| ATPLUS ® PFA | 5 |
| Ethylenediaminetetraacetic acid (EDTA), Tetrasodium Tetrahydrate Salt | 1.583 |
| Propylene Glycol | 10 |
| Dibasic Potassium Phosphate | 1.869 |
| Monobasic Potassium Phosphate | 1.262 |
| Cetrimonium chloride | 0.25 |
| SAG 1572* | 0.05 |
| KATHON ® CG/ICP | 0.05 |

TABLE 19-continued

| Component | TFORM191024_ BG_1, _3, _5 Target (wt. %) |
|---|---|
| ROCIMA ® BT2S | 0.1 |
| Water | q.s. |

Examples 13-18: Persistent Foaming Test

Persistent foam of each formulation at the maximum label rate as a diluted system is measured according to CIPAC MT 47. The graduated cylinder used in this experiment is a 250 mL cylinder that fits the requirements specified in the method of testing. This is reported as a maximum volume after 1 minute upon standing.

Example 13

Formulations containing dsRNA for foliar application have been developed that stabilize dsRNA for storage stability, and for use as a diluted spray solution. The use of surfactants and other stabilizers in the formulation to prevent dsRNA degradation, as well as enable a shelf-stable formulation containing dsRNA results in significant persistent foam when diluted into a spray solution for foliar application. The addition of an anti-foam type compound in the formulation composition is required reduce or eliminate this persistent foam upon dilution for practical application. Typical anti-foams have been found to exhibit significant stability challenges when formulated with dsRNA and the other co-formulants, which can be categorized as an aqueous based formulation with a high electrolyte content. The exemplified formulation composition contains an anti-foam type component that exhibits excellent stability with dsRNA formulations over various storage conditions, while also providing excellent foam reduction upon dilution in a spray solution. This compatibility in the formulation, and results of persistent foaming tests are shown in this example.

FIGS. 10A, 10B, 11A, and 11B are examples according to various embodiments, illustrating photographs of a compatible formulation comprising SAG 1572™ anti-foam after storage for 2 weeks at −10° C., and 2 and 8 weeks at 4° C., 8 weeks at 40° C., 2 weeks at 54° C., demonstrating excellent dsRNA stability.

The formulations described above were prepared according to the method described in Example 1 and had the compositions according to Table 20.

TABLE 20

| Component | TFORM191024_ BG_3 Target (wt. %) |
|---|---|
| dsRNA | 0.8 |
| ATPLUS ® PFA | 5 |
| Ethylenediaminetetra acetic acid (EDTA), Tetrasodium Tetrahydrate Salt | 1.583 |
| Propylene Glycol | 10 |
| Dibasic Potassium Phosphate | 1.869 |
| Monobasic Potassium Phosphate | 1.262 |
| Cetrimonium chloride | 0.25 |
| SAG 1572* | 0.05 |
| KATHON ® CG/ICP | 0.05 |
| ROCIMA ® BT2S | 0.1 |
| Water | q.s. |

Example 14

Figures 12A, 12B:
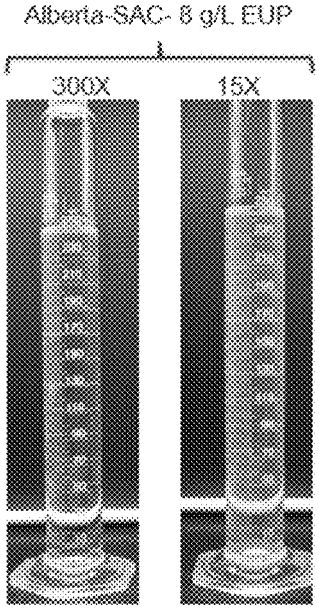
FIGS. 12A and 12B are examples according to various embodiments, illustrating persistent foaming test results for a formulation comprising SAG 1572™ anti-foam and 8 g/L of dsRNA obtained from a TGAI source, diluted at 300× and 15× rates in 342 ppm water, respectively, as specified by CIPAC MT 18, showing absence of persistent foam, and exceptional foam reduction, upon standing for 1 minute.
Figures 12C, 12D:
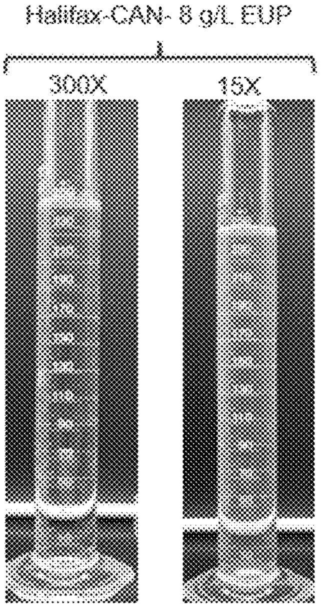
FIGS. 12C and 12D are examples according to various embodiments, illustrating persistent foaming test results for a formulation comprising SAG 1572™ anti-foam and 8 g/L of dsRNA obtained from a TGAI source, diluted at 300× and 15× rates in 342 ppm water, respectively, as specified by CIPAC MT 18, showing absence of persistent foam, and exceptional foam reduction, upon standing for 1 minute.
Figures 12E, 12F:
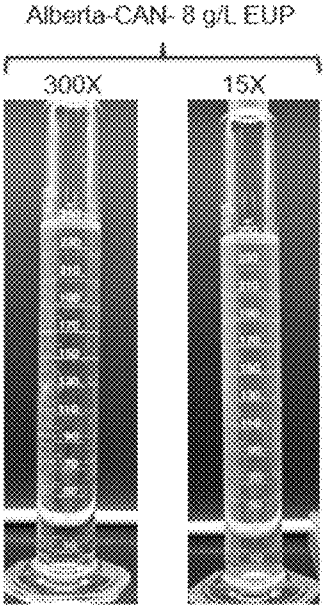
FIGS. 12E and 12F are examples according to various embodiments, illustrating photographs of persistent foaming test results for a formulation comprising SAG 1572™ anti-foam and 8 g/L of dsRNA obtained from a TGAI source, diluted at 300× and 15× rates in 342 ppm water, respectively, as specified by CIPAC MT 18, showing absence of persistent foam, and exceptional foam reduction, upon standing for 1 minute.
Figures 13A, 13B, 13C, 13D, 13E, 13F:
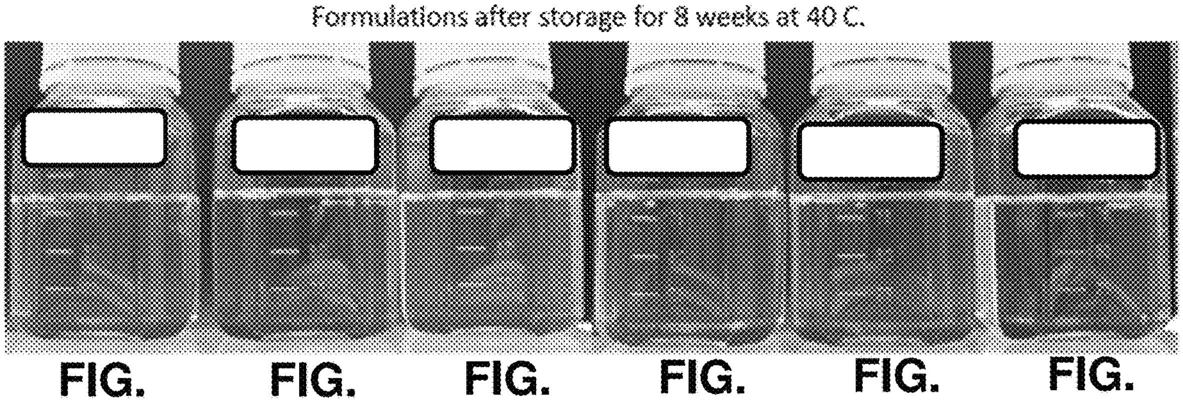
FIGS. 13A, 13B, 13C, 13D, 13E, 13F are examples according to various embodiments, illustrating photographs of formulations comprising SAG 1572™ anti-foam after storage for 8 weeks at 40° C., exhibiting excellent dsRNA stability.
Figures 13G, 13H, 13I, 13J, 13K, 13L:
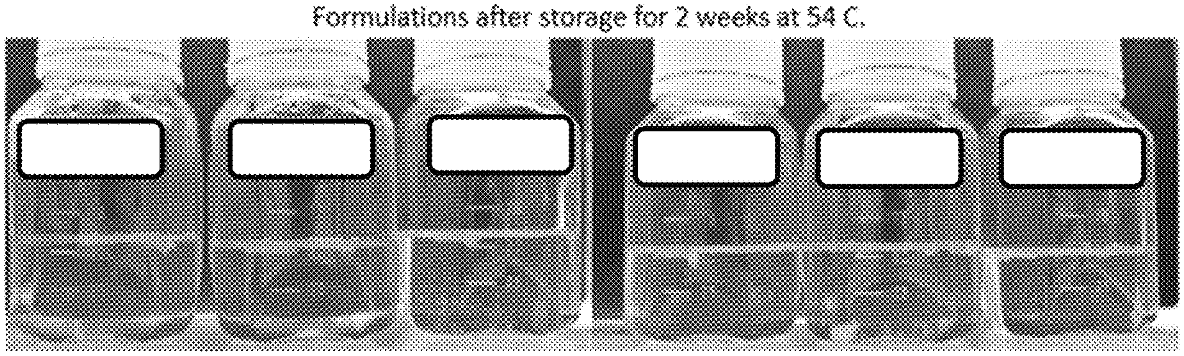
FIGS. 13G, 13H, 13I, 13J, 13K, 13L are examples according to various embodiments, illustrating photographs of formulations comprising SAG 1572™ anti-foam after storage for 2 weeks at 54° C., exhibiting excellent dsRNA stability.

This example demonstrates compatibility in various formulations and further results of persistent foaming tests. FIGS. 12A and 12B are examples according to various embodiments, illustrating persistent foaming test results for a formulation comprising SAG 1572™ anti-foam and 8 g/L of dsRNA obtained from a TGAI source, diluted at 300× and 15× rates in 342 ppm water, respectively, as specified by CIPAC MT 18, showing absence of persistent foam, and exceptional foam reduction, upon standing for 1 minute. FIGS. 12C and 12D are examples according to various embodiments, illustrating persistent foaming test results for a formulation comprising SAG 1572™ anti-foam and 8 g/L of dsRNA obtained from an Halifax-CAN TGAI source, diluted at 300× and 15× rates in 342 ppm water, respectively, as specified by CIPAC MT 18, showing absence of persistent foam, and exceptional foam reduction, upon standing for 1 minute. FIGS. 12E and 12F are examples according to various embodiments, illustrating photographs of persistent foaming test results for a formulation comprising SAG 1572™ anti-foam and 8 g/L of dsRNA obtained from a TGAI source, diluted at 300× and 15× rates in 342 ppm water, respectively, as specified by CIPAC MT 18, showing absence of persistent foam, and exceptional foam reduction, upon standing for 1 minute.

The formulations described above were prepared according to the method described in Example 1 and had the compositions according to Table 21.

TABLE 21

| Component | Probe 1.0-I-1 Target (wt. %) |
|---|---|
| dsRNA | 0.4 |
| ATPLUS ® PFA | 10 |
| Ethylenediaminetetra acetic acid (EDTA), Tetrasodium Tetrahydrate Salt | 0.625 |
| Propylene Glycol | 10 |
| Dibasic Potassium Phosphate | 1.544 |
| Monobasic Potassium Phosphate | 1.043 |
| Cetrimonium chloride | 0.25 |
| SAG 1572* | 0.05 |
| KATHON ® CG/ICP | 0.05 |
| ROCIMA ® BT2S | 0.1 |
| Water | q.s. |

Example 15

This example demonstrates results obtained for formulations containing SAG 1572™ anti-foam have also been stored at 54° C. for 2 weeks, and 40° C. for 8 weeks to complete accelerated storage conditions. These formulations exhibit excellent stability of dsRNA, and remain physically stable over the time courses tested. Any slight precipitation events, which consist primarily of the emulsified silicon-based oils for use as anti-foams have been drastically minimized in the formulation, and if present are able to pass through a 150-um sieve.

FIGS. 13A, 13B, 13C, 13D, 13E, 13F are examples according to various embodiments, illustrating photographs of formulations comprising SAG 1572™ anti-foam after storage for 8 weeks at 40° C., exhibiting excellent dsRNA stability. FIGS. 13G, 13H, 13I, 13J, 13K, 13L are examples according to various embodiments, illustrating photographs of formulations comprising SAG 1572™ anti-foam after storage for 2 weeks at 54° C., exhibiting excellent dsRNA stability.

The formulations described above were prepared according to the method described in Example 1 and had the compositions according to Table 22.

TABLE 22

| Component | TFORM191024_ BG_1, _3, _5 Target (wt. %) | TFORM191024_BG_ 2, _4, _6 Target (wt. %) |
|---|---|---|
| dsRNA | 0.8 | 0.4 |
| ATPLUS ® PFA | 5 | 5 |
| Ethylenediamine-tetraacetic acid (EDTA), Tetrasodium Tetrahydrate Salt | 1.583 | 1.583 |
| Propylene Glycol | 10 | 10 |
| Dibasic Potassium Phosphate | 1.869 | 1.869 |
| Monobasic Potassium Phosphate | 1.262 | 1.262 |
| Cetrimonium chloride | 0.25 | 0.25 |
| SAG 1572* | 0.05 | 0.05 |
| KATHON ® CG/ICP | 0.05 | 0.05 |
| ROCIMA ® BT2S | 0.1 | 0.1 |
| Water | q.s. | q.s. |

Example 16

This example demonstrates results for a formulation composition comprising SAG 1572™ with a specified use rate of 0.05% in the formulation. This concentration was identified following a titration study aimed at reducing the total concentration of antifoam in the formulation. This minimum use rate was identified by evaluating the efficacy of foam reduction in the solution upon dilution, and the results can be seen in the figure below.

Figures 14A, 14B, 14C, 14D:
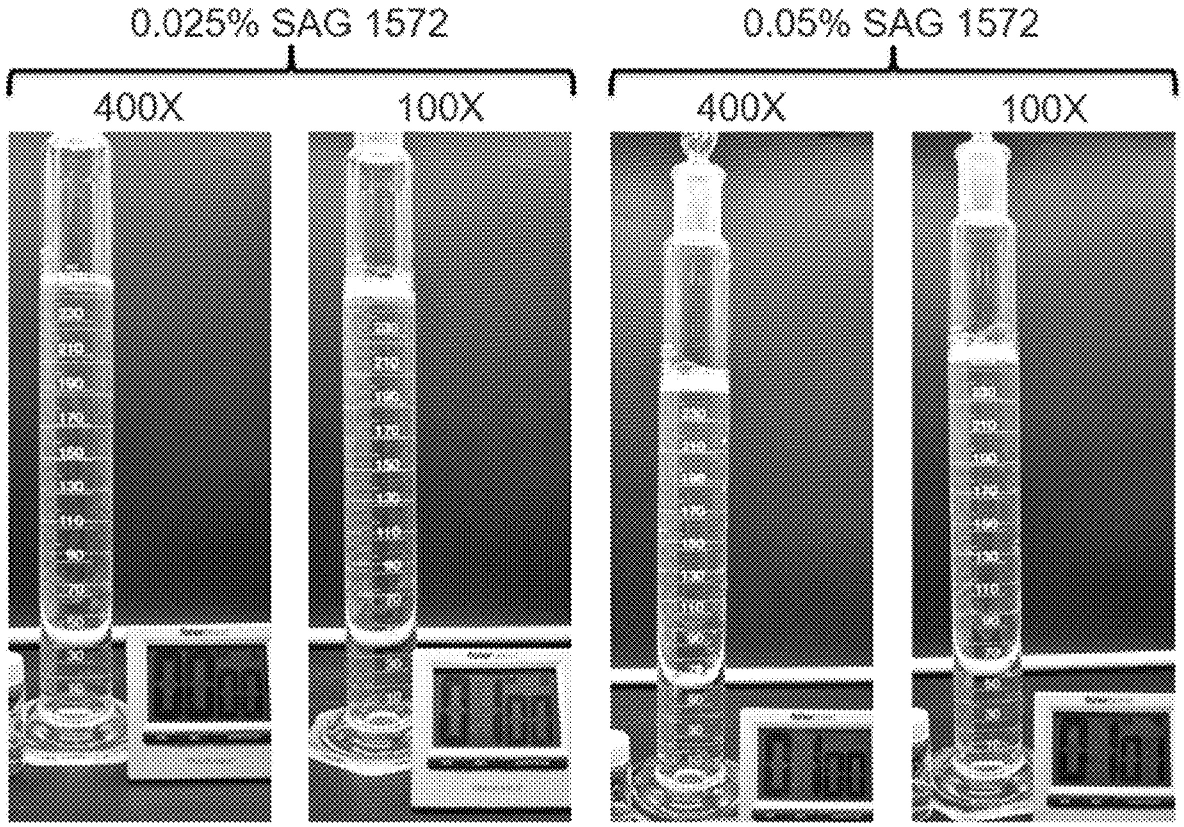
FIGS. 14A and 14B are examples according to various embodiments, illustrating photographs of titration assays for formulations comprising 0.025% SAG 1572™ antifoam and dsRNA at 400× and 100× dilution in 342 ppm water, respectively.
FIGS. 14C and 14D are examples according to various embodiments, illustrating photographs of titration assays for formulations comprising 0.05% SAG 1572™ antifoam and dsRNA at 400× and 100× dilution in 342 ppm water, respectively.

FIGS. 14A and 14B are examples according to various embodiments, illustrating photographs of titration assays for formulations comprising 0.025% SAG 1572™ antifoam and dsRNA at 400× and 100× dilution in 342 ppm water, respectively. FIGS. 14C and 14D are examples according to various embodiments, illustrating photographs of titration assays for formulations comprising 0.05% SAG 1572™ antifoam and dsRNA at 400× and 100× dilution in 342 ppm water, respectively.

The formulations described above were prepared according to the method described in Example 1 and had the compositions according to Table 23.

TABLE 23

| Component | Probe 1.0_I-1A Target (wt. %) | Probe 1.0_I-1B Target (wt. %) |
|---|---|---|
| dsRNA | 0.4 | 0.4 |
| TWEEN 20 ™ | 10 | 10 |
| Ethylenediaminetetraacetic acid (EDTA), Tetrasodium Tetrahydrate Salt | 0.625 | 0.625 |
| Propylene Glycol | 10 | 10 |
| Dibasic Potassium Phosphate | 1.545 | 1.545 |
| Monobasic Potassium Phosphate | 1.043 | 1.043 |
| Cetrimonium chloride | 0.25 | 0.25 |
| SAG 1572* | 0.025 | 0.05 |
| KATHON ® CG/ICP | 0.05 | 0.05 |
| ROCIMA ® BT2S | 0.1 | 0.1 |
| Water | q.s. | q.s. |

Example 17

While SAG 1572™, as illustrated in Examples 14-16, showed the best stability and efficacy results as the antifoam agent in formulations according to various embodiments, several other antifoam components were tested for compatibility and foam reduction. This example demonstrates that SAG 1599™ provides more stability to the tested composition than does SAG 1572™.

Figure 15:
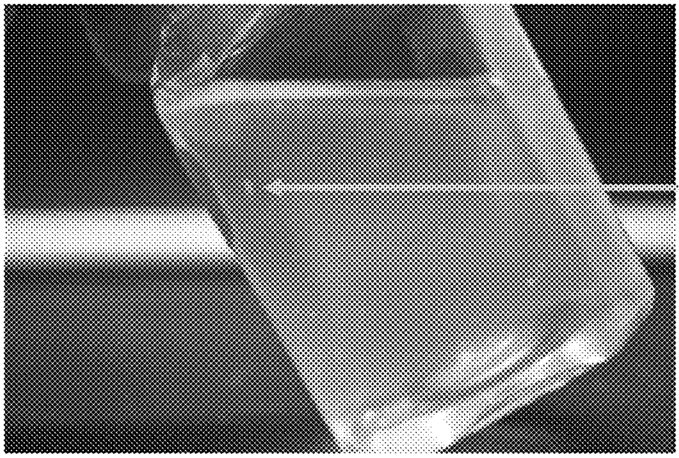
FIG. 15 is an example according to various embodiments, illustrating a photograph showing the physical incompatibility and physical stability of SAG 1599™ in a concentrated formulation.

FIG. 15 is an example according to various embodiments, illustrating a photograph showing the incompatibility and physical stability of SAG 1599™ in a concentrated formulation. Agglomeration of silicone and oil particles in the formulation during storage, highlights the stability challenges of formulating an oil-based antifoam component into a high salt aqueous formulation.

The formulation described above was prepared according to the method described in Example 1 and had the composition according to Table 24.

TABLE 24

| Component | Target (wt. %) |
|---|---|
| dsRNA | 0.4 |
| TWEEN 20 ™ | 10 |
| Ethylenediaminetetraacetic acid (EDTA), Tetrasodium Tetrahydrate Salt | 0.625 |
| Propylene Glycol | 10 |
| Dibasic Potassium Phosphate | 1.545 |
| Monobasic Potassium Phosphate | 1.043 |
| Cetrimonium chloride | 0.25 |
| SAG 1599 ™ | 0.05 |
| KATHON ® CG/ICP | 0.05 |
| ROCIMA ® BT2S | 0.1 |
| Water | q.s. |

Example 18

This example demonstrates that ANTIFOAM GN11P™ results in a reduction in efficacy of foam reduction compared to SAG 1572™.

Figure 16:
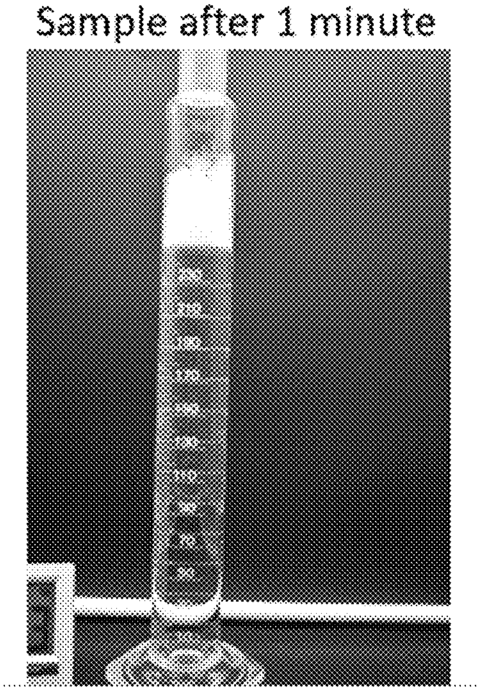
FIG. 16 is an example according to various embodiments, illustrating a photograph of a formulation comprising 0.2% ANTIFOAM GN11P™ after 1 minute upon standing.

FIG. 16 is an example according to various embodiments, illustrating a photograph of a formulation comprising 0.2% ANTIFOAM GN11P™ after 1 minute upon standing. No significant foam reduction properties were observed for this formulation as prepared, and the antifoam component was determined to not be as effective as other options in solution.

The formulation described above was prepared according to the method described in Example 1 and had the composition according to Table 25.

TABLE 25

| Component | Target (wt. %) |
|---|---|
| dsRNA | 0.4 |
| TWEEN 20 ™ | 10 |
| Ethylenediaminetetraacetic acid (EDTA), Tetrasodium Tetrahydrate Salt | 0.625 |
| Propylene Glycol | 10 |
| Dibasic Potassium Phosphate | 1.545 |
| Monobasic Potassium Phosphate | 1.043 |
| Cetrimonium chloride | 0.25 |
| Antifoam GN11P | 1.0 |
| KATHON ® CG/ICP | 0.05 |
| ROCIMA ® BT2S | 0.1 |
| Water | q.s. |

Examples 19-22: Bacterial and Fungal Biocontamination Challenger Studies

Bacterial and Fungal biocontamination studies were performed using these formulations to evaluate their inherent ability to withstand bacterial and fungal contamination, which could occur if a container were unsealed and contaminated before use. These assays were performed using a modified version of United States Pharmacopeia Chapter 51: Antimicrobial Effectiveness Testing. Within this method of testing each formulation, with and without the selected biocidal and fungicidal preservatives KATHON® CG/ICP and ROCIMA® BT2S, are subjected to a bacterial or fungal cocktail challenge where selected organisms are introduced to the material to evaluate proliferation or decrease in the organism counts. The following fungi cultures have been selected for the fungal cocktail and include *Aspergillus niger* (filamentous morph), *Candida albicans* (yeast morph), *Penicilium commune* (common contaminant, filamentous), and *Aurebasidium pullulans* (common contaminant, dimorphic). The following bacteria cultures have been selected for the bacterial cocktail and include *Escherichia coli* (common contaminant), *Pseudomonas fluorescens, Bacillus licheniformis* (a spore forming, thermo-tolerant bacteria that excretes protease and RNAse), and *Serratia marcescens*. To perform this testing 40 mL of each formulation, with and without preservatives, is aliquoted into a sterile conical and samples are spiked with either the bacterial or fungal cocktail. Both the bacterial cocktail and fungal cocktails are spiked into the formulations at 1% (v/v) with a target concentration of greater than $1\times10^6$ CFU/mL and $1\times10^5$ CFU/mL for bacteria and fungi, respectively. Each sample is stored at 30° C. for 4 weeks to promote bacterial and fungal growth. Aliquots are taken for testing on days 0, 1, 7, 14, 21, and 28 continually to evaluate bacterial and fungal concentration in the sample. Bacterial counts are performed by spreading the aliquot to be tested onto a Tryptic Soy plate, incubating at 30° C. for 1-3 days, and checked daily for bacterial growth prior to obtaining total cell count. Fungal counts are performed by spreading the aliquot to be tested onto a Sabouraud Dextrose Agar plate, incubating at 25° C. for 3-5 days, and checking daily for fungal growth prior to obtaining total cell count. Biocontamination is recorded in CFU/mL which is determined by the total number of colonies measured multiplied by any dilution factor, if necessary, and divided by the total volume of the sample in milliliters.

Formulations containing dsRNA are particularly susceptible to degradation of dsRNA from bacterial and fungal contamination over extended time in storage. The developed formulations contain a preservative and surfactant package that inhibits bacterial and fungal degradation of dsRNA during shelf storage. Non-formulated dsRNA exhibits significant degradation of dsRNA within 21 days of storage when exposed to a $10^4$ CFU level of fungal contamination. Non-formulated dsRNA exhibits complete degradation of dsRNA within 21 days of storage when exposed to a $10^7$ CFU level of bacterial contamination. dsRNA that has been treated with the preservative package, but not the additional cationic surfactant package that has been developed for this formulation, does not exhibit significant degradation of dsRNA after 42 days of storage when exposed to a $10^4$ CFU level of fungal contamination. Non-formulated dsRNA or TGAI that has been treated with the preservative package, but not the additional cationic surfactant package that has been developed for this formulation, exhibits significant degradation of dsRNA after 14 days of storage when exposed to a $10^7$ CFU level of bacterial contamination. All formulated dsRNA that has been treated with the preservative and surfactant package specific to the exemplified formulation composition demonstrate excellent stability of dsRNA when contaminated with $10^4$ CFU of fungal contamination and $10^7$ CFU of bacterial contamination. The degradation profile of non-formulated dsRNA, or TGAI, that has been treated with the preservative package, but not the additional cationic surfactant package, demonstrates the need and utility the cationic surfactant package as a necessary component to ensure complete protection of dsRNA from degradation due to bacterial contamination. This dataset in particular highlights the advantages of an additional preservative component even when using the traditional broad-spectrum preservative package consisting of BIT, CMIT, and MIT. HPLC quantification, and bioburden spore count measurements have demonstrated that formulations containing dsRNA are able to withstand considerable bacterial and fungal contamination, both in eliminating the bioburden level within 1-7 days, and preventing any dsRNA degradation over 42 days storage at 37° C. This is different than the non-formulated dsRNA that is treated with the preservatives alone, which demonstrate bacterial and fungal spore take down between 1-7 days but exhibit dsRNA degradation due to bacterial contamination after 14 days. This demonstrates the specific stability benefits to dsRNA the formulation provides in both knockdown of spore counts for biocontamination, and protection of dsRNA from degradation due to biocontamination over the same period. The examples below demonstrate bioburden levels after bacterial, and fungal challenge, and dsRNA degradation profiles after bacterial and fungal challenge, for non-formulated and formulated dsRNA.

Example 19

Figure 17:
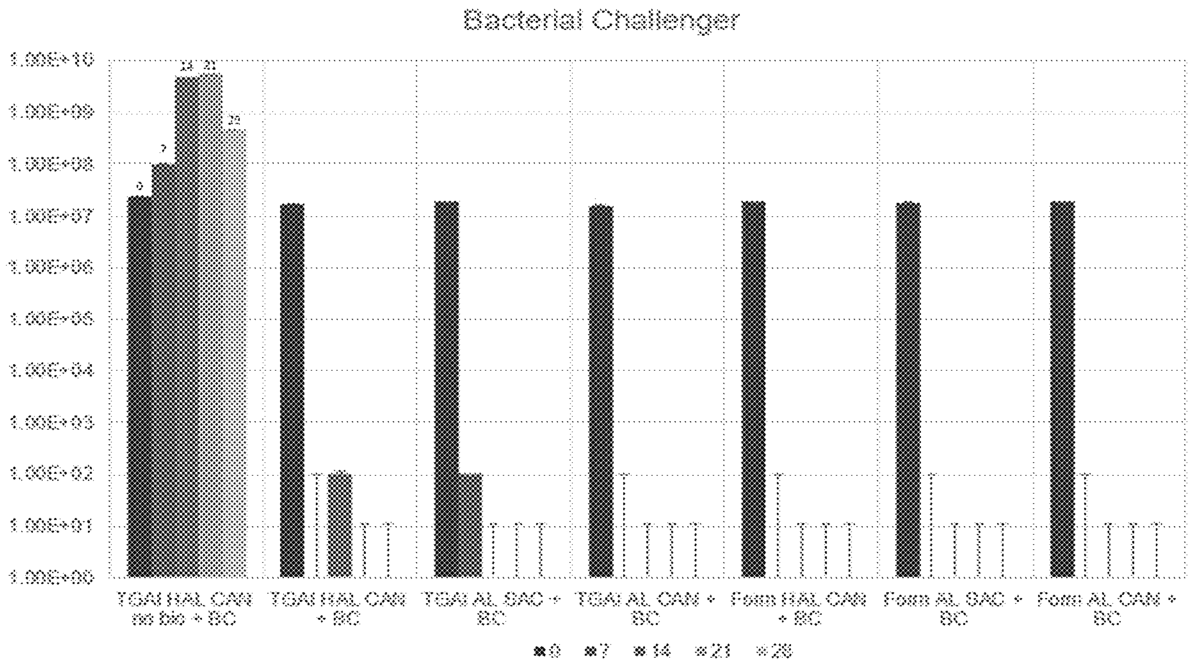
FIG. 17 is an example according to various embodiments, illustrating results for non-formulated TGAI and formulated TGAI containing dsRNA bioburden levels after contamination with 107 CFU of the bacterial cocktail, in which the designations HAL CAN, AL SAC, AL CAN represent three different yeast sources for production of TGAI.

FIG. 17 is an example according to various embodiments, illustrating results for unformulated dsRNA (first column) dsRNA formulated with KATHON® CG/ICP and ROCIMA® BT2S (columns 2-4), and dsRNA formulated as set forth in Table 26 (columns 5-7). The figure demonstrates that use of various packages help with reduction of bioburden levels after contamination with $10^7$ CFU of the bacterial cocktail.

TABLE 26

| Component | Target (wt. %) |
|---|---|
| dsRNA | 0.4 |
| ATPLUS ® PFA | 10 |

TABLE 26-continued

| Component | Target (wt. %) |
|---|---|
| Ethylenediaminetetraacetic acid (EDTA), Tetrasodium Tetrahydrate Salt | 0.625 |
| Propylene Glycol | 10 |
| Dibasic Potassium Phosphate | 1.545 |
| Monobasic Potassium Phosphate | 1.043 |
| Cetrimonium chloride | 0.25 |
| SAG1572 | 0.05 |
| KATHON ® CG/ICP | 0.05 |
| ROCIMA ® BT2S | 0.1 |
| Water | q.s. |

Example 20

Figure 18:
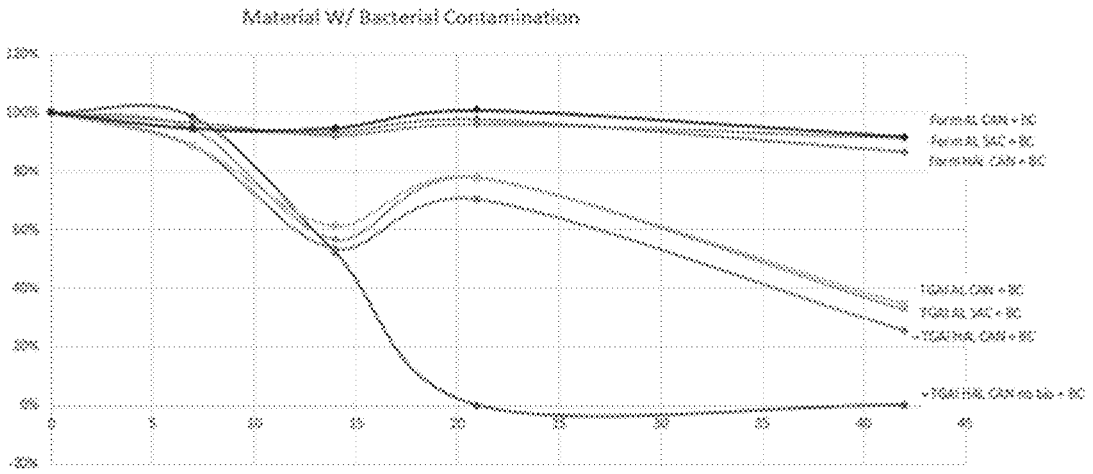
FIG. 18 is an example according to various embodiments, illustrating dsRNA degradation profiles for non-formulated dsRNA and formulated dsRNA after contamination with 107 CFU of the bacterial cocktail, in which HAL CAN, AL SAC, AL CAN represent three different yeast sources for production of TGAI.

FIG. 18 is an example according to various embodiments, illustrating dsRNA degradation profiles for non-formulated dsRNA (labeled "TGAI HAL CAN no bio+BC"), dsRNA formulated with ROCIMA® BT2S and KATHON® CG/ICP (labeled "TGAI . . . BC") and formulated dsRNA as set forth in Table 26 (labeled "FORM . . . ") after contamination with $10^7$ CFU of the bacterial cocktail. HAL CAN, AL SAC, AL CAN represent three different yeast sources for production of TGAI. These results demonstrate that although ROCIMA® BT2S and KATHON® CG/ICP alone had some effectiveness in eliminating bacterial infection over time, they were not effective on their own in providing stability to the dsRNA, due to remaining bacterial nuclease activity that remained even after the bacteria had been eliminated. The Table further demonstrates that the samples formulated with the metal ion sequestrant inhibited nuclease activity and in combination with the secondary surfactant provided strong stability after the bacterial challenge after 42 days of storage at 37° C. post contamination.

Example 21

Figure 19:
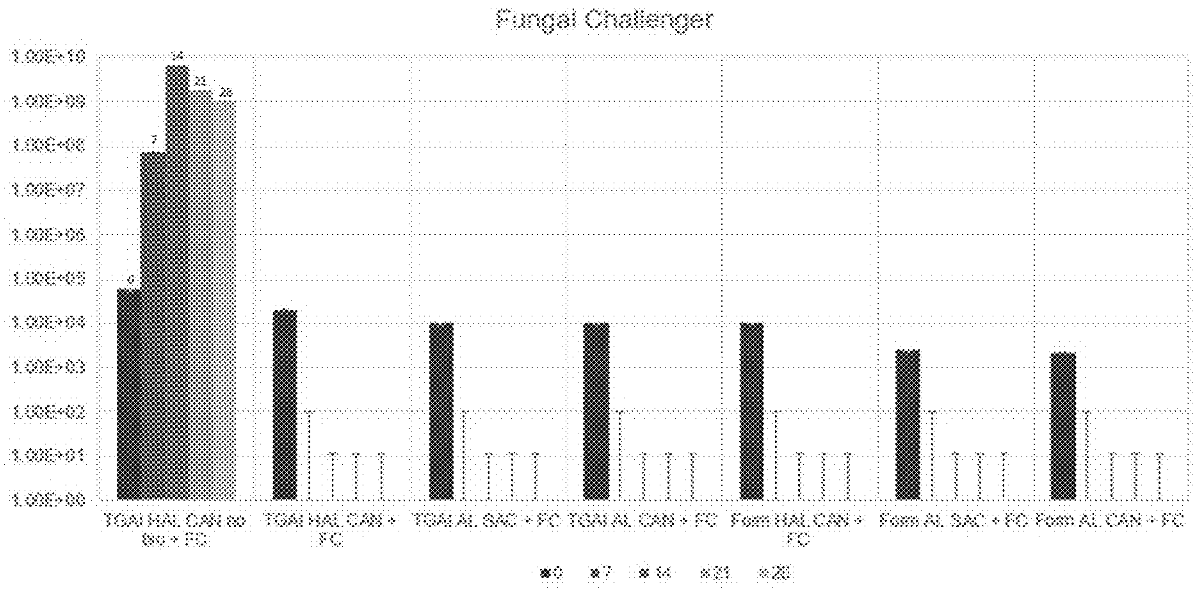
FIG. 19 is an example according to various embodiments, illustrating results for non-formulated dsRNA and formulated dsRNA containing dsRNA bioburden levels after contamination with 104 CFU of the fungal cocktail, in which HAL CAN, AL SAC, AL CAN represent three different yeast sources for production of TGAI.

FIG. 19 is an example according to various embodiments, illustrating results for unformulated dsRNA (first column) dsRNA formulated with KATHON® CG/ICP and ROCIMA® BT2S (columns 2-4), and dsRNA formulated as set forth in Table 26 (columns 5-7). The figure demonstrates that use of various packages help with reduction of bioburden levels after contamination with $10^4$ CFU of the fungal cocktail, in which HAL CAN, AL SAC, AL CAN represent three different yeast sources for production of TGAI.

Example 22

Figure 20:
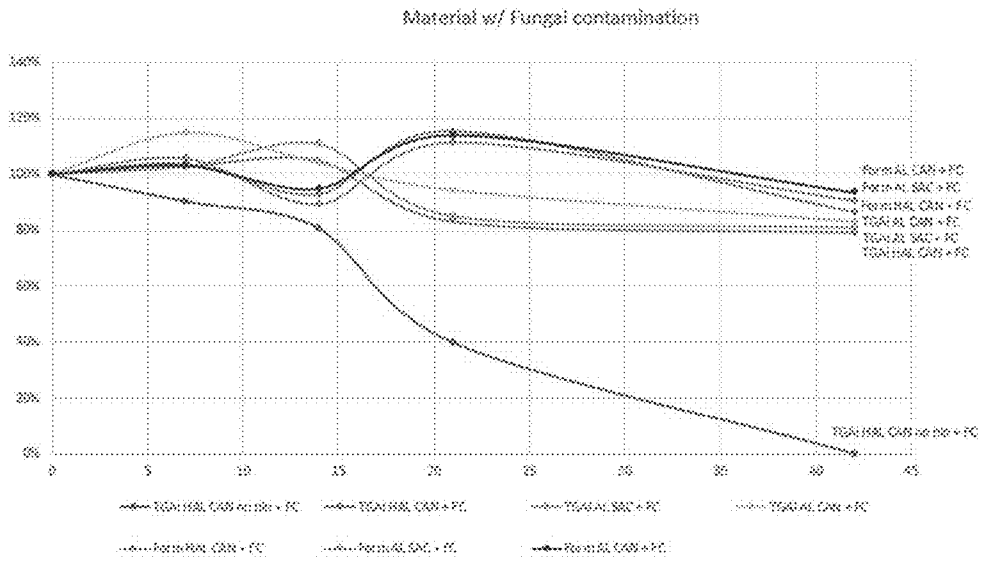
FIG. 20 is an example according to various embodiments, illustrating dsRNA degradation profiles non-formulated dsRNA and formulated dsRNA after contamination with 104 CFU of the fungal cocktail, in which HAL CAN, AL SAC, AL CAN represent three different yeast sources for production of TGAI.

FIG. 20 is an example according to various embodiments, illustrating dsRNA degradation profiles non-formulated dsRNA (labeled "TGAI HAL CAN no bio+BC"), dsRNA formulated with ROCIMA® BT2S and KATHON® CG/ICP (labeled "TGAI . . . BC") and formulated dsRNA as set forth in Table 26 (labeled "FORM . . . "). after contamination with 10^4 CFU of the fungal cocktail.HAL CAN, AL SAC, AL CAN represent three different yeast sources for production of TGAI. These results demonstrate that although ROCIMA® BT2S and KATHON® CG/ICP alone had effectiveness in eliminating the fungal contamination, they were provided acceptable protection from nuclease activity, though not as effective as the more formulations of Table 26, which include a metal ion sequestrant and a secondary surfactant.

Examples 23-25: Bacterial Challenge Plating Assay and Water Activity Determination The addition of a cationic type surfactant is utilized as a key component of the overall preservative package due to the desired antimicrobial effect of alkyl ammonium chlorides in aqueous solution. Bacterial and fungal degradation of dsRNA is a critical barrier to delivery of dsRNA containing solutions for practical application, and the inclusion of these type of co-formulants is critical for dsRNA stability. To effectively screen formulations for the inclusion of cationic surfactant components, and to determine the minimum inhibitory concentration of those components in the formulation a plate-based assay was developed. The plate based assay was performed on microtiter plates with Tryptic soy broth, using *Escherichia Coli* at $1\times10^8$ CFU/mL and *Bacillus Licheniformis* at $1\times10^6$ CFU/mL count rates as the bacterial organisms. Ammonium containing formulation components were screened different concentrations using a step-wise reduction to determine the minimum inhibitory concentration of each component for both organisms. Each formulation was serially diluted in a microtiter plate, and a 10 uL spike of each culture was added prior to using a plate replicator tool to spot the sample on a 150 mm tryptic soy agar plate. After completing the concentration spotting for each formulation component the tryptic soy plates were incubated overnight at 30 C, and imaged after 18 hours incubation. Biocontrol properties and minimum inhibitory concentrations for each component was determined when the spots resulted in individual colonies as opposed to a full micro lawn of bacterial growth.

To further characterize the formulation for inherent biocontrol properties, the water activity level was measured. The water activity level was measured using a Novasine Lab Master Neo. Water activity is a critical measurement and is used to determine the amount of free water in the formulation in order to compare against known minimum water activity levels for propagation of contaminating organisms.

Results from the bacterial contamination challenger study demonstrate the advantages for an additional preservative component, which has been included as the addition of a cationic surfactant. In order to demonstrate the biocontrol effects, and identify a minimum use rate in the formulation a plating-based assay was develop to screen components, and concentrations. Three different components were selected to test, covering three distinct classes of chemistry. Cetrimonium chloride was selected to represent an alkyl ammonium chloride, a traditional cationic surfactant approved for food use. Lauryl betaine was selected to represent betaines, a type of zwitterionic compound that exhibits an ammonium functionality across all pH's due to the location of the inner salt in the structure. MACAT® AO-12 was selected as an amine oxide, a type of surfactant that contain an amine functionality but does not exist as a charged species like the cationic or zwitterionic components. Results from the plate-based assay indicate that the cationic surfactant provides the greatest benefit against the organisms tested, and has a minimum use rate of 0.05% in the formulation. Lauryl betaine was shown to provide protection against the organisms to a lesser degree than the cetrimonium chloride, and had a minimum suggested use rate of 0.75% in the formulation. The amine oxide surfactant was not shown to demonstrate any biocontrol against *E. coli*, and demonstrates the specific need for a zwitterionic, or more preferably a cationic surfactant for improved biocontrol properties against contamination. The results for these assays are shown in the Examples below.

Example 23

Figure 21A:
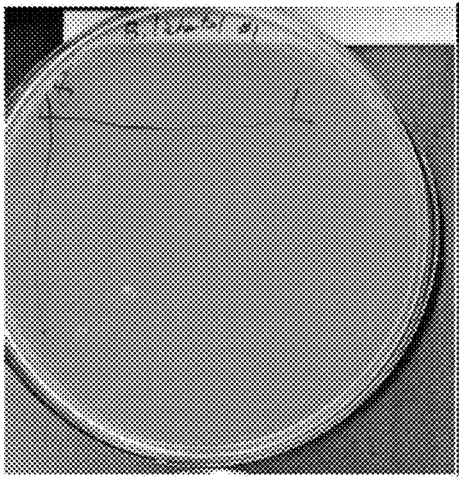
FIGS. 21A and B are examples according to various embodiments, illustrating photographs of plating-based assays for cetrimonium chloride challenged with B. *Licheniformis* and *E. Coli*, respectively.
Figure 21B:
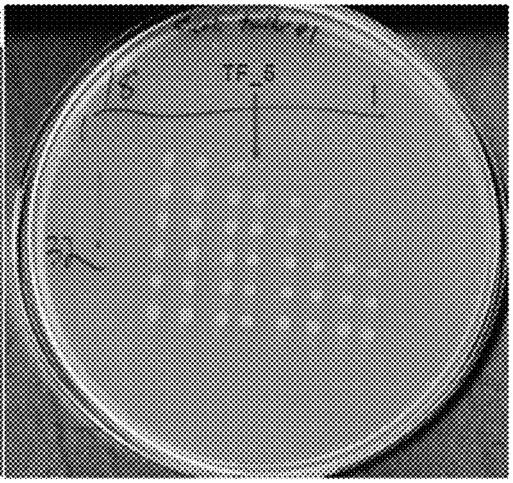

FIGS. 21A and B are examples according to various embodiments, illustrating photographs of plating-based assays for cetrimonium chloride challenged with B. *Licheniformis* and *E. Coli*, respectively. The minimum inhibitory concentration for cetrimonium chloride was determined to be 0.05% in the formulation. Absence of a micro-lawn of growth in the spotted plate indicates inhibitory control of the organism.

The formulations described above were prepared according to the method described in Example 1 and had the compositions according to Table 27.

TABLE 27

| Component | Example 21 Target (wt. %) |
|---|---|
| dsRNA | 0.4 |
| ATPLUS ® PFA | 10 |
| Ethylenediaminetetraacetic acid (EDTA), Tetrasodium Tetrahydrate Salt | 1.583 |
| Propylene Glycol | 10 |
| Dibasic Potassium Phosphate | 1.545 |
| Monobasic Potassium Phosphate | 1.043 |
| Cetrimonium chloride | variable |
| SAG1572 ™ | 0.05 |
| KATHON ® CG/ICP | 0.05 |
| ROCIMA ® BT2S | 0.1 |
| Water | q.s. |

Example 24

Figure 22A:
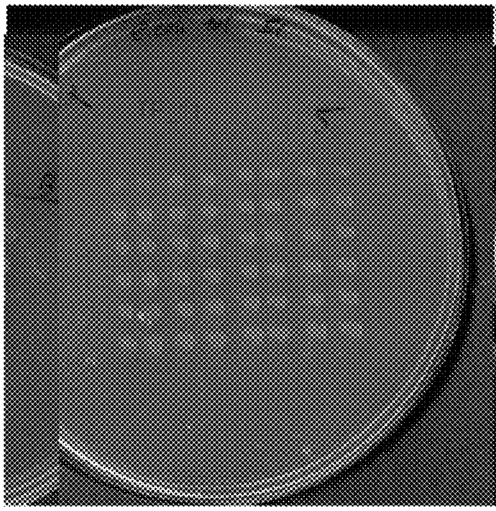
FIGS. 22A and 22B are examples according to various embodiments, illustrating photographs of plating-based assays for lauryl betaine challenged with B. *Licheniformis* and *E. Coli*, respectively.
Figure 22B:
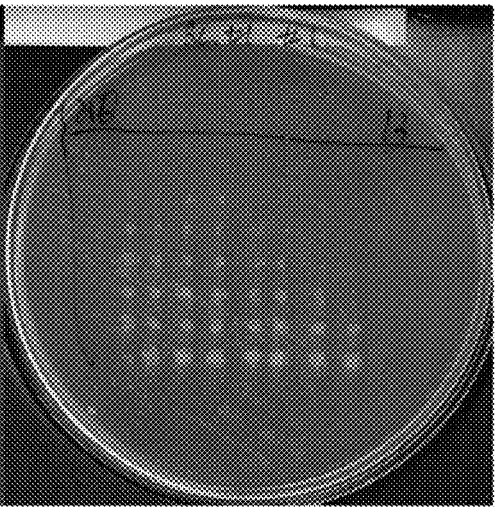

FIGS. 22A and 22B are examples according to various embodiments, illustrating photographs of plating-based assays for lauryl betaine challenged with *B. Licheniformis* and *E. Coli*, respectively. The minimum inhibitory concentration for lauryl betaine was determined to be 0.75% in the formulation. Absence of a micro-lawn of growth in the spotted plate indicates inhibitory control of the organism.

The formulations described above were prepared according to the method described in Example 1 and had the compositions according to Table 28.

TABLE 28

| Component | Example 21 Target (wt. %) |
|---|---|
| dsRNA | 0.4 |
| ATPLUS ® PFA | 10 |
| Ethylenediaminetetraacetic acid (EDTA), Tetrasodium Tetrahydrate Salt | 1.583 |
| Propylene Glycol | 10 |
| Dibasic Potassium Phosphate | 1.545 |
| Monobasic Potassium Phosphate | 1.043 |
| Lauryl betaine | variable |
| SAG1572 ™ | 0.05 |
| KATHON ® CG/ICP | 0.05 |
| ROCIMA ® BT2S | 0.1 |
| Water | q.s. |

Example 25

Figure 23A:
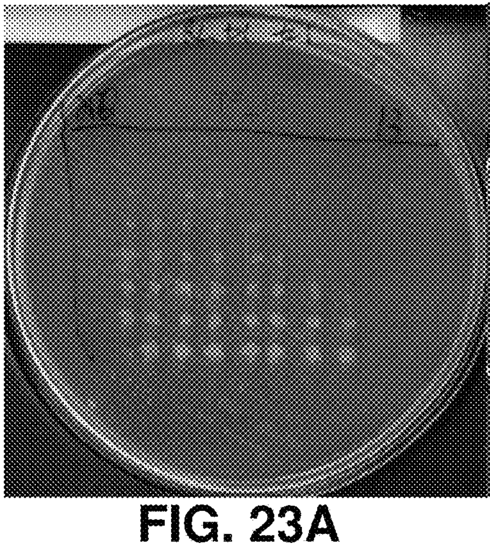
FIGS. 23A and 23B are examples according to various embodiments, illustrating photographs of plating-based assays for C12 amine oxide challenged with B. *Licheniformis* and *E. Coli*, respectively.
Figure 23B:
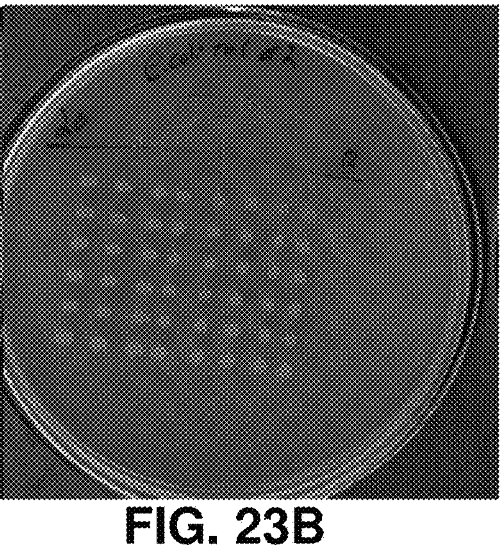

FIGS. 23A and 23B are examples according to various embodiments, illustrating photographs of plating-based assays for C12 amine oxide challenged with *B. Licheniformis* and *E. Coli*, respectively. The minimum inhibitory concentration for C12 amine oxide was determined to be 0.5% in the formulation. Absence of a micro-lawn of growth in the spotted plate indicates inhibitory control of the organism.

The formulations described above were prepared according to the method described in Example 1 and had the compositions according to Table 29.

TABLE 29

| Component | Example 21 Target (wt. %) |
|---|---|
| dsRNA | 0.4 |
| ATPLUS ® PFA | 10 |
| Ethylenediaminetetraacetic acid (EDTA), Tetrasodium Tetrahydrate Salt | 1.583 |
| Propylene Glycol | 10 |
| Dibasic Potassium Phosphate | 1.545 |
| Monobasic Potassium Phosphate | 1.043 |
| MACAT ® AO | variable |
| SAG1572 | 0.05 |
| KATHON ® CG/ICP | 0.05 |
| ROCIMA ® BT2S | 0.1 |
| Water | q.s. |

Example 26

In addition to the biocontrol properties due to the specific nature of the cationic surfactant, and broad-spectrum preservative package, a formulation was analyzed for water activity levels. Individual organisms require a certain concentration of free water to promote and encourage bacterial or fungal growth. Due to the high level of salts, and other surfactants in the formulation, the water level of the formulation was measured to determine the inherent biocontrol properties of the formulation as is and demonstrate the advantages for a preservative package to prevent dsRNA degradation due to microbial contamination, potentially occurring if a container were to be unsealed and contaminated prior to use. A listing of the water activity levels necessary for propagation a variety of organisms, and the water activity of several formulations are shown in Table 30.

TABLE 30

| Formulation | ATPLUS ® PFA (wt %) | TGAI (wt %) | A_w |
|---|---|---|---|
| TForm190828_BG_15 | 10 | 0.4 | 0.9475 |
| TForm190828_BG_16 | 5 | 0.4 | 0.9510 |
| TForm190828_BG_17 | 10 | 0.8 | 0.9441 |
| TForm190828_BG_18 | 5 | 0.8 | 0.9485 |

Table 30 shows water activity levels of several tested formulations. Surfactant concentration was tested at 5% and 10%, and dsRNA concentration was tested at 4 g/L and 8 g/L. Results of this assay demonstrate that the formulation has a very low water activity level between 0.944-0.951 and contains some inherent biocontrol properties against several organisms. However, since several additional common organisms have lower water activity levels, the need for additional preservative components is highlighted. Additionally, no significant difference is seen between increasing surfactant of dsRNA concentration.

The formulations described above were prepared according to the method described in Example 1 and had the compositions according to Table 31.

TABLE 31

| Component | TForm190828_BG_15 Target (wt. %) | TForm190828_BG_16 Target (wt. %) | TForm190828_BG_17 Target (wt. %) | TForm190828_BG_18 Target (wt. %) |
|---|---|---|---|---|
| dsRNA | 0.4 | 0.4 | 0.8 | 0.8 |
| ATPLUS ® PFA | 10 | 5 | 10 | 5 |
| Ethylenediaminetetraacetic acid (EDTA), Tetrasodium Tetrahydrate Salt | 1.583 | 1.583 | 1.583 | 1.583 |
| Propylene Glycol | 10 | 10 | 10 | 10 |
| Dibasic Potassium Phosphate | 1.869 | 1.869 | 1.869 | 1.869 |
| Monobasic Potassium Phosphate | 1.262 | 1.262 | 1.262 | 1.262 |
| Cetrimonium chloride | 0.25 | 0.25 | 0.25 | 0.25 |
| SAG1572 ™ | 0.05 | 0.05 | 0.05 | 0.05 |
| KATHON ® CG/ICP | 0.05 | 0.05 | 0.05 | 0.05 |
| ROCIMA ® BT2S | 0.1 | 0.1 | 0.1 | 0.1 |
| Water | q.s. | q.s. | q.s. | q.s. |

For reference, Table 32 provides Water activity levels for several common organisms. Minimum water activity levels necessary for growth are listed.

TABLE 32

| Water Activity | Bacteria | Microorganism Molds | Yeast |
|---|---|---|---|
| 0.97 | *Clostridium botulinum* E<br>*Pseudomonas fluorescens* | — | — |
| 0.95 | *Escherichia coli*<br>*Clostridium perfringens*<br>*Salmonella spp.*<br>*Vibrio cholerae* | — | — |
| 0.94 | *Clostridium borulinum* A, B<br>*Vibrio parahaemolyticus* | *Stachybotrys atra* | — |
| 0.93 | *Bacillus cereus* | *Rhizopus nigricans* | |
| 0.92 | *Listeria monoeytogenes* | | |
| 0.91 | *Bacillus subtilis* | | |
| 0.90 | *Staphylococcus aureus* (anaerobic) | *Trichothecium roseum* | *Saccharomyces cerevisiae* |
| 0.88 | | | *Candida* |
| 0.86 | *Staphylococcus aureus* (aerobic) | | |
| 0.85 | | *Aspergillus clavatus* | |
| 0.84 | | *Byssochlamys nivea* | |
| 0.83 | | *Penicillium expansum*<br>*Penicillum islandicum*<br>*Penicillum viridicatum* | *Debarymoces hansenii* |
| 0.82 | | *Aspergillus fumigatus*<br>*Aspergillus parasiticus* | |
| 0.81 | | *Penicillum cyclopium*<br>*Penicillum patulum* | |
| 0.80 | | *Penicillium citrinum* | *Saccharomyces bailii* |
| 0.79 | | *Penicillum martensii* | |
| 0.78 | | *Aspergillus flavus* | |
| 0.77 | | *Aspergillus niger*<br>*Aspergillus ochraceous* | |
| 0.75 | | *Aspergillus restrictus*<br>*Aspergillus candidus* | |
| 0.71 | | *Eurotium chevalieri* | |
| 0.70 | | *Eurotium amstelodami* | |
| 0.62 | | | *Saccharomyces rouxii* |
| 0.61 | | *Monascus bisporus* | |
| <0.60 | No microbial proliferation | | |

Examples 27-29: EDTA Concentration and Enzymatic Nuclease Degradation Studies Two separate nuclease challenge testing assays were developed using benzonase to determine dsRNA stability in formulations containing various concentrations of EDTA. EDTA is used in formulations containing dsRNA to stabilize dsRNA against nuclease activity and prevent degradation over various storage conditions, as well as contamination. The standard nuclease activity testing utilized 0.3 U/uL of benzoase, and a 3 hour incubation period at 37 C with formulations containing dsRNA. EDTA was used to quench nuclease activity after the 3 hour time period, and then samples were run as untreated and treated samples on a 1.2% agarose gel using electrophoresis. Quantitative determination of dsRNA in samples treated with 0.3 U/uL of benzonase was also performed via HPLC. dsRNA degradation was evaluated qualitatively by the disappearance of the corresponding molecular weight band in the gel, and quantitatively by the HPLC analysis. An Ultra nuclease challenge assay was developed to rapidly test dsRNA formulation in 1 hour against a significant excess of benzonase. This testing protocol was used to screen EDTA concentrations to determine the minimum concentration of EDTA necessary to inhibit nuclease activity in formulated samples. The ultra-nuclease activity testing utilized 30 U/uL of benzoase, and a 1 hour incubation period at 37 C with formulations containing dsRNA. EDTA was used to quench nuclease activity after the 1 hour time period, and then samples were run as untreated and treated samples on a 1.2% agarose gel using electrophoresis. Quantitative determination of dsRNA in samples treated with 30 U/uL of benzonase was also performed via HPLC. dsRNA degradation was evaluated qualitatively by the disappearance of the corresponding molecular weight band in the gel, and quantitatively by the HPLC analysis.

Enzymatic nuclease activity has been determined to be a significant cause of dsRNA degradation and instability of solutions containing dsRNA over various storage conditions. Many nucleases require divalent metal ions to catalyze their enzymatic processes, therefore shelf-stable formulations containing dsRNA require a metal-ion chelator present to sequester divalent metal-ions from the system and inhibit nuclease activity. Since dsRNA is a polyanion and exists as a double stranded nucleic acid helices with a phosphate backbone, there is significant potential for dsRNA itself to be contain free divalent metal-ions, such as $Mg^{2+}$, as a counter ion species associated with the phosphate backbone in aqueous solution. Additionally, the cell-free reaction utilized to produce dsRNA, requires specific concentrations of divalent metal-ions such as $Mg^{2+}$ to construct the dsRNA molecules. The presence of divalent metal-ions during the production of dsRNA creates an inherent susceptibility towards nuclease activity in the TGAI. Practical production of dsRNA utilizing this cell-free reaction is prohibitive to substantial dialysis, and counter ion replacement methods commonly used to remove divalent ions at the lab-scale. Therefore, it is critical to the stability of dsRNA within formulations to contain the appropriate concentration of chelators, such as EDTA.

Example 27

Figure 24:
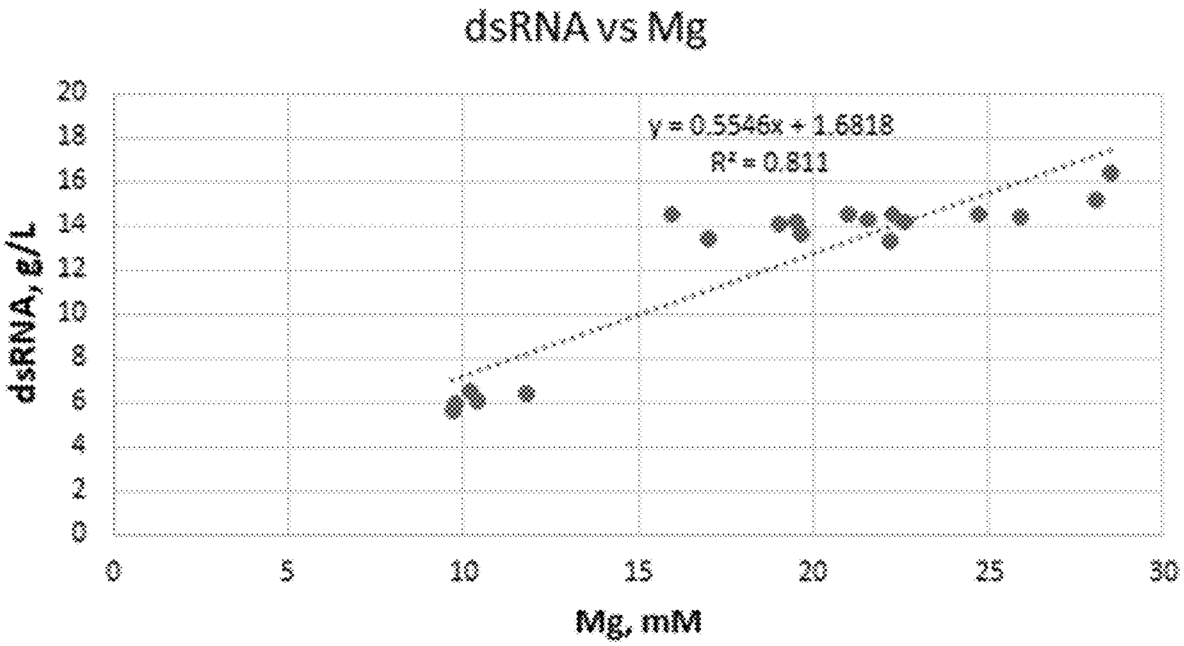
FIG. 24 is an example according to various embodiments, illustrating $Mg^{2+}$ analysis of multiple production lots of TGAI, including TGAI produced at 7 g/L dsRNA which contained between 9-13 mM $Mg^{2+}$, with an average content of 10 mM; and TGAI produced at 14 g/L dsRNA, which contained between 15.5-28 mM $Mg^{2+}$, with an average content of 22.5 mM.

Multiple production lots of TGAI were analyzed for $Mg^{2+}$ content to understand the concentration range of these divalent ions in the TGAI at certain target dsRNA concentrations and can be seen in FIG. 24. More specifically, FIG. 24 is an example according to various embodiments, illustrating $Mg^{2+}$ analysis of multiple production lots of TGAI, including TGAI produced at 7 g/L dsRNA which contained between 9-13 mM $Mg^{2+}$, with an average content of 10 mM; and TGAI produced at 14 g/L dsRNA, which contained between 15.5-28 mM $Mg^{2+}$, with an average content of 22.5 mM.

Example 28

Figure 25:
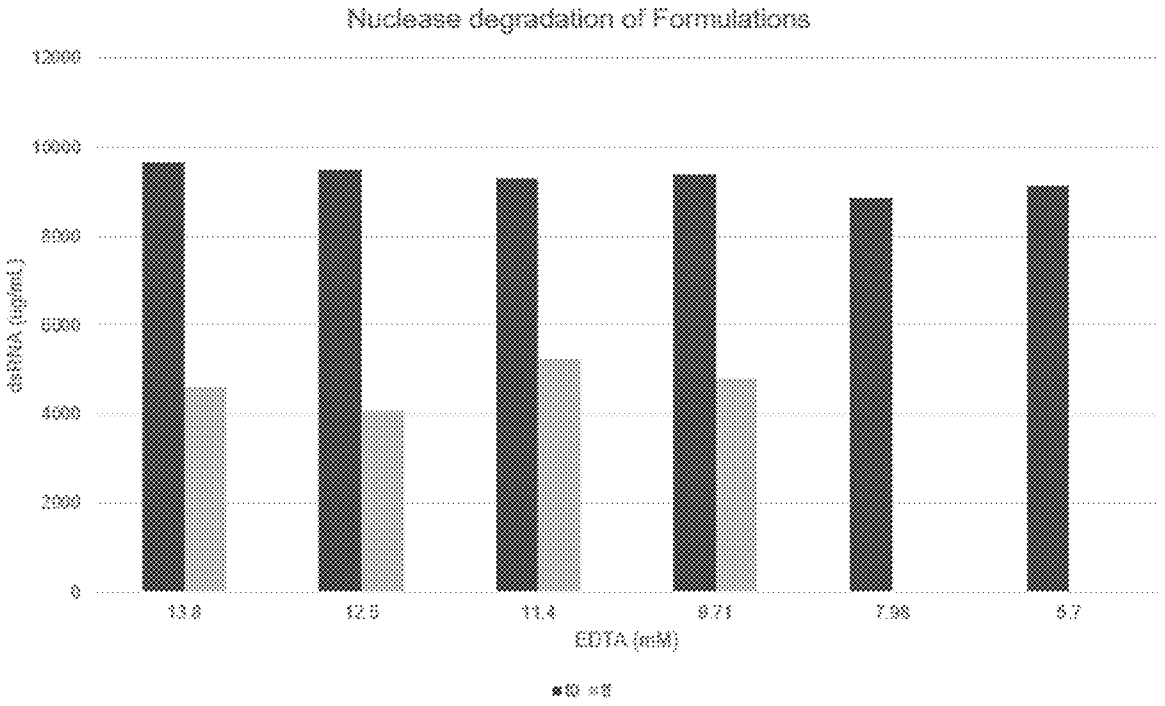
FIG. 25 is an example illustrating dsRNA degradation due to nuclease activity.

Initial concentrations of EDTA, at 13.8 mM, that demonstrated adequate protection of dsRNA in a 4 g/L end use product, where determined to be inadequate in protecting dsRNA at higher concentrations when formulated. Further reduction of EDTA concentration in the formulated dsRNA product only resulted in even more complete degradation of dsRNA via nuclease activity. This trend, and the results of dsRNA degradation due to uninhibited nuclease activity are shown in FIG. 25. More specifically, FIG. 25 is an example according to various embodiments, illustrating dsRNA degradation due to nuclease activity. Formulations with decreasing concentrations of the metal ion chelator were shown to provide inadequate inhibition of benzonase, a non-specific nuclease. Further reduction of EDTA below 8 mM for the compositions tested resulted in complete degradation, whereas higher concentrations of EDTA were not adequate to provide complete protection for the compositions tested in this Example, but did change the reaction kinetics, results in only partial degradation over the time course.

The formulations described above were prepared according to the method described in Example 1 and had the compositions according to Table 33.

TABLE 33

| | TForm190829 _BG_3 | TForm190829 _BG_7 | TForm190829 _BG_4 | TForm190829 _BG_8 |
|---|---|---|---|---|
| Component | Target (wt. %) | Target (wt. %) | Target (wt. %) | Target (wt. %) |
| dsRNA | 0.4 | 0.4 | 0.4 | 0.4 |
| ATPLUS ® PFA | 10 | 10 | 10 | 10 |
| Ethylenediaminetetra acetic acid (EDTA), Tetrasodium Tetrahydrate Salt | 0.4 | 0.25 | 0.125 | 0.0625 |
| Propylene Glycol | 10 | 10 | 10 | 10 |
| Dibasic Potassium Phosphate | 0.1545 | 0.1545 | 0.1545 | 0.1545 |
| Monobasic Potassium Phosphate | 0.1043 | 0.1043 | 0.1043 | 0.1043 |
| Cetrimonium chloride | 0.25 | 0.25 | 0.25 | 0.25 |
| SAG1572 ™ | 0.05 | 0.05 | 0.05 | 0.05 |

TABLE 33-continued

| | TForm190829_BG_3 | TForm190829_BG_7 | TForm190829_BG_4 | TForm190829_BG_8 |
|---|---|---|---|---|
| KATHON ® CG/ICP | 0.05 | 0.05 | 0.05 | 0.05 |
| ROCIMA ® BT2S | 0.1 | 0.1 | 0.1 | 0.1 |
| Water | q.s. | q.s. | q.s. | q.s. |

From this data it was determined that, according to various embodiments, it may be beneficial to increase the EDTA concentration in the formulation above 13.8 mM (>0.4 wt %) and also demonstrated the general advantage of including a metal ion chelator in the compositions of the present disclosure.

Example 29

A separate nuclease challenge assay was developed using an extreme excess of benzonase to determine a minimum level of EDTA necessary to provide dsRNA stability from nuclease mediated degradation, for a representative TGAI lot containing 22.6 mM $Mg^{2+}$. The results from this assay indicated that an increase of roughly 2 mM from a 1:1 molar equivalence of EDTA to $Mg^{2+}$ ions was needed to definitively inhibit nuclease mediated degradation of dsRNA. Results from this ultra nuclease challenge assay are shown in FIGS. 26 and 27.

Figure 26:
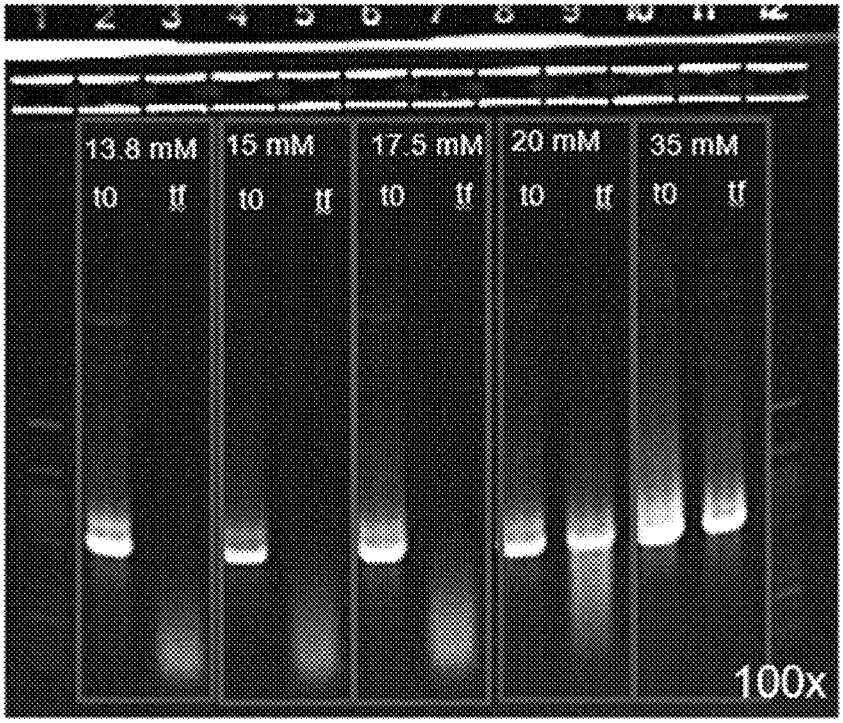
FIG. 26 is an example according to various embodiments, illustrating gel electrophoresis results of dsRNA formulations containing increasing concentration of EDTA.

FIG. 26 is an example according to various embodiments, illustrating gel electrophoresis results of dsRNA formulations containing increasing concentration of EDTA. The TGAI lot used to produce these formulations contained 22.6 mM of $Mg^{2+}$, and a major improvement of stability to nuclease susceptibility is observed as EDTA concentration increases above 20 mM. A molar excess of EDTA, at 35 mM, clearly demonstrates complete qualitative stability, and maintains integrity of dsRNA to nuclease activity.

Figure 27:
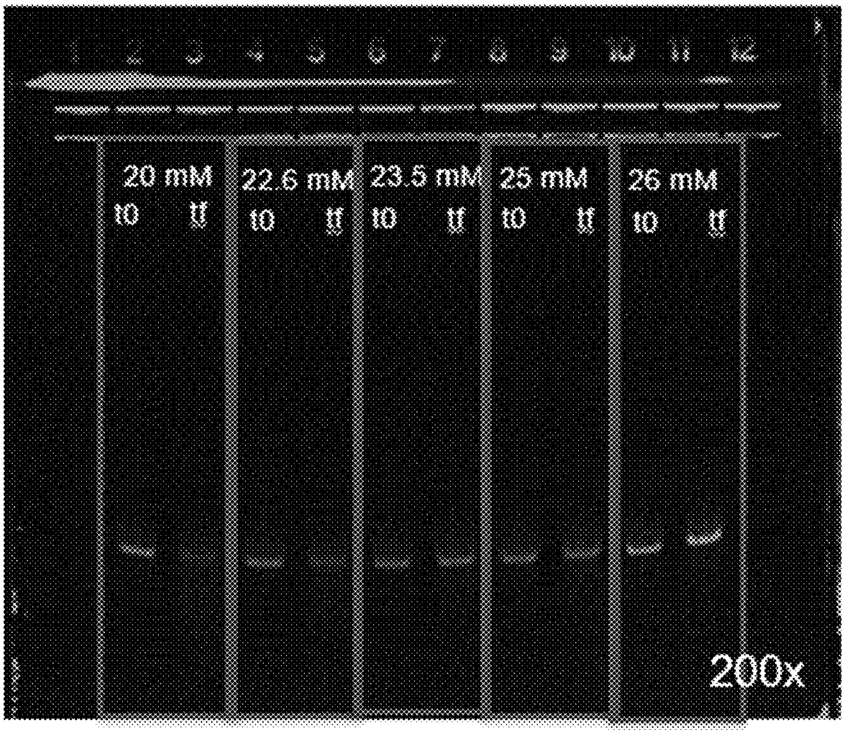
FIG. 27 is an example according to various embodiments, illustrating gel electrophoresis results of dsRNA formulations containing increasing concentration of EDTA.

FIG. 27 is an example according to various embodiments, illustrating gel electrophoresis results of dsRNA formulations containing increasing concentration of EDTA. Gel electrophoresis of dsRNA formulations containing increasing concentration of EDTA. The TGAI lot used to produce these formulations contained 22.6 mM of $Mg^{2+}$, and a stability to nuclease activity is observed as EDTA concentration increases ~2 mM above molar equivalence, or 22.6 mM.

The formulations described above were prepared according to the method described in Example 1 and had the compositions according to Table 34.

TABLE 34

| Component | TForm191021_BG_1; _2, _3, _4, _7 Target (wt. %) |
|---|---|
| dsRNA | 0.8 |
| ATPLUS ® PFA | 5 |
| Ethylenediaminetetraacetic acid (EDTA), Tetrasodium Tetrahydrate Salt | 0.625; 0.679; 0.792; 0.905; 1.583 |
| Propylene Glycol | 10 |
| Dibasic Potassium Phosphate | 1.869 |
| Monobasic Potassium Phosphate | 1.262 |
| Cetrimonium chloride | 0.25 |
| SAG1572 ™ | 0.05 |
| KATHON ® CG/ICP | 0.05 |
| ROCIMA ® BT2S | 0.1 |
| Water | q.s. |

Combining the data from the initial nuclease challenge assay, the ultra nuclease challenge assays, and the $Mg^{2+}$ concentration data collected for several production lots of TGAI, it was determined that, according to various embodiments, about 35 mM of EDTA was an appropriate concentration to include in formulations containing dsRNA to provide stability from nuclease activity and to help prevent degradation of dsRNA under practical storage conditions.

Examples 30-36: UV Radiation Stability Testing

UV-B Radiation levels were monitored from outside over the course of 2 weeks in Boston, MA. The energy levels collected were used to determine UV-B exposure levels over the course of 1 day, 7 days, and 14 days. Naked dsRNA was subjected to UV radiation over the course of 2 weeks in Boston, MA. The integrity and degradation profile of dsRNA over this time course was evaluated by HPLC quantification. Naked dsRNA exposed for 1 week in environmental conditions were determined to be completely degraded, and the total UV-B exposure to dsRNA over this time period was determined to be 79 J/cm$^2$.

Samples containing dsRNA were placed in a UV radiation chamber, and conditioned with 100 J/cm$^2$ of UV-B radiation. This level of radiation was determined to be at least equivalent to, or in excess of the average level of radiation exposure measured over the course of 1 week in a normal environment in Boston, MA. These samples were prepared both on parafilm lined plates to determine the inherent photostability of the sample, as well as in planta to determine any effects of photostability on a leaf surface. Each sample was conditioned as 9 replicate samples of 5 ug dsRNA. After conditioning with UV radiation, samples were reconstituted in 200 uL of water and pooled for analysis.

Pooled samples of UV conditioned materials were analyzed by gel electrophoresis to qualitatively determine both dsRNA recovery and integrity of the samples. Invitrogen E-Gel Flash electrophoresis systems were used to generate results.

Pooled samples of UV conditioned materials were analyzed by HPLC to quantitatively determine dsRNA recovery and quantification of the dsRNA post-exposure.

Bioassays of samples were performed in laboratory with a leaf spreading application. 20 Colorado Potato beetle larvae were used per treatment. Samples were provided after exposure to 0 J/cm$^2$ UV radiation as a positive control, 100 J/cm$^2$ UV radiation as the determined level equivalent to over 1 week exposure under normal environmental conditions, and 200 J/cm$^2$ UV radiation as a negative control due to complete dsRNA degradation under these conditions. Differences in mortality between formulations at different levels of exposure and compositions containing the additional UV protectant dispersant type surfactant were determined after 9 days post treatment.

A summary of chemistries tested, and level of UV protection offered for dsRNA post exposure is shown in the Table 35.

TABLE 35

| Coformulants Tested | Chemistry Classification | UV Protection? |
|---|---|---|
| REAX ® 105M, KRAFTSPERSE ® 8828, REAX ® 1425E, REAX ® 910, REAX ® 960 | Lignosulfonates (Polymer Conjugated Aromatic) | Yes |
| MORWET ® D-425, MORWET ® IP MORWET ® EFW | Napthalene Sulfonate Condensates | Yes, Slight |
| Triton X-100 | Alkyl Phenyl Ethoxylate (Aromatic) | No |
| Calsoft AOS-1245 | Sodium Methyl Oleyl Taurate (olefinic) | No |

Example 30

UV Radiation levels were determined over the course of 2 weeks on a rooftop in Boston, MA. Quantification of dsRNA in samples exposed to these environmental conditions were monitored by HPLC to determine exposure limits and degradation effects. dsRNA was found to be completely degraded, via HPLC determination, after 1 week, which was determined to be equivalent to 76 J/cm$^2$ UV-B radiation. After 2 weeks exposure, which was equivalent to 131 J/cm$^2$ UV-B exposure, dsRNA quantification was reduced to 0 ng/µL.

Figure 28:
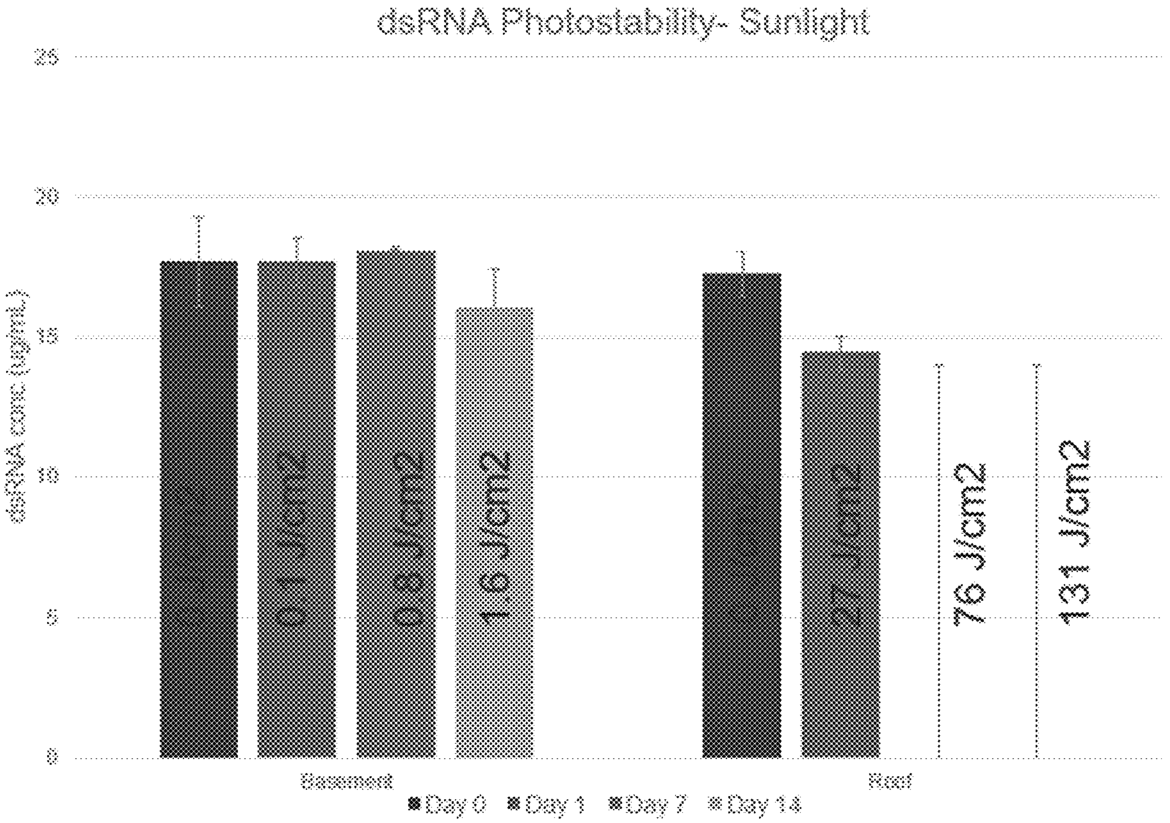
FIG. 28 is an example according to various embodiments, illustrating UV-B Exposure Levels, and dsRNA Stability after 2 weeks

FIG. 28 is an example according to various embodiments, illustrating UV-B Exposure Levels, and dsRNA Stability after 2 weeks.

The formulations described above were prepared according to the method described in Example 1 and had the compositions according to Table 36.

TABLE 36

| Component | TForm191118_WS Target (wt. %) |
|---|---|
| dsRNA | 0.8 |
| ATPLUS ® PFA | 5 |
| Ethylenediaminetetraacetic acid (EDTA), Tetrasodium Tetrahydrate Salt | 1.583 |
| Propylene Glycol | 10 |
| Dibasic Potassium Phosphate | 1.869 |
| Monobasic Potassium Phosphate | 1.262 |
| Cetrimonium chloride | 0.25 |
| SAG1572 ™ | 0.05 |
| KATHON ® CG/ICP | 0.05 |
| ROCIMA ® BT2S | 0.1 |
| Water | q.s. |

Example 31

Examination of the individual chromatograms collected for the samples tested after UV exposure demonstrated that while quantification of dsRNA via HPLC had been reduced to 0 ng/uL, dsRNA, ssRNA, and free nucleotide peaks exhibited significant skewing and shifting. This shifting and skewing of the RNA type peaks demonstrates that some level of dsRNA remains after 7-14 days, but the chemical shift indicates a random loss in size and base pairs in the sample. Blending of the dsRNA and ssRNA peak indicates that significant degradation and conformational change to the dsRNA occurs after 7-14 days UV exposure, but what is unclear is whether this degradation results in loss of efficacy.

Figure 29:
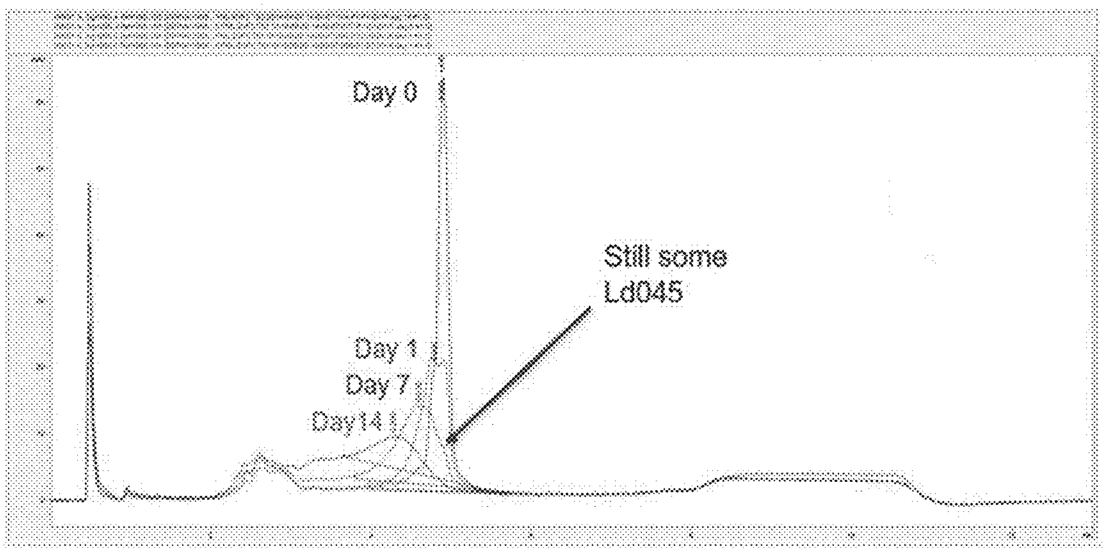
FIG. 29 is an example according to various embodiments, illustrating an HPLC Chromatogram overlay of dsRNA after various UV-B exposures.

FIG. 29 is an example according to various embodiments, illustrating an HPLC Chromatogram overlay of dsRNA after various UV-B exposures. Peak intensity of dsRNA is significantly reduced after 1-day exposure. dsRNA and ssRNA peaks begin to broaden and blend after 7-14 days exposure to UV radiation. The formulations described were prepared according to the method described in Example 1 and had the composition specified in Example 30.

Example 32

Figure 30:
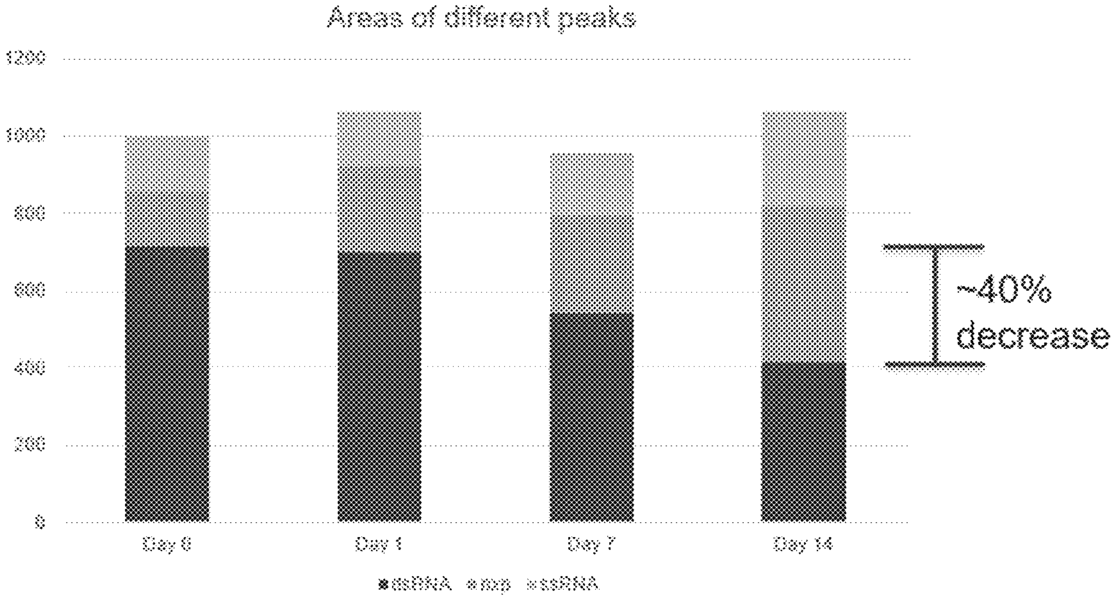
FIG. 30 is an example according to various embodiments, illustrating mass balances of dsRNA, ssRNA, and free nucleotides in dsRNA samples after 2 weeks exposure to UV radiation.

FIG. 30 is an example according to various embodiments, illustrating mass balances of dsRNA, ssRNA, and free nucleotides in dsRNA samples after 2 weeks exposure to UV radiation. Significant decrease in dsRNA, slight increase in ssRNA, and significant increase in free nucleotides is indicative of dsRNA degradation. The formulations described were prepared according to the method described in Example 1 and had the composition specified in Example 30.

Example 33

Alternate formulations were developed that contained a lignosulfonate dispersant type surfactant. Lignosulfonates consist of a polymeric network containing sulfonated conjugated aromatic functionalities. It was hypothesized that this polymeric network of conjugated aromatic functionalities would have a significant beneficial impact on UV protection due to absorbance of UV radiation. Five formulations were produced with a variety of lignosulfonates, all containing different molecular weights, degree of sulfonation, and site of sulfonation, and were tested for protection from UV radiation against the exemplified formulation that does not contain this type of surfactant. These formulations were dried on parafilm plates and then exposed to 100 J/cm$^2$ of UV-B radiation in a UV chamber. The samples were rehydrated with water and then analyzed by gel electrophoresis to qualitatively determine dsRNA degradation, and via HPLC to quantitatively determine dsRNA degradation. The gel and HPLC results can be seen in the FIGS. 31 and 32.

Figure 31:
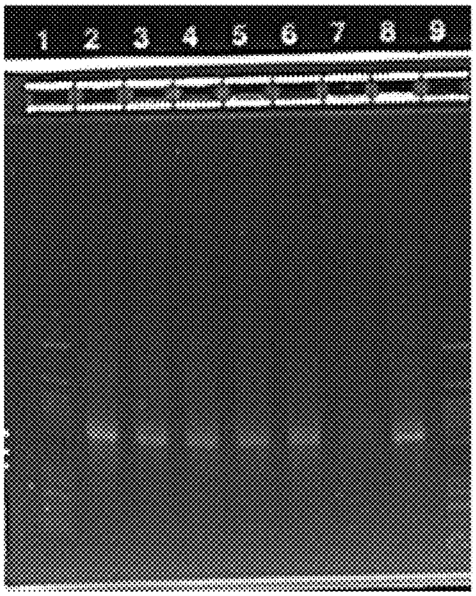
FIG. 31 is an example according to various embodiments, illustrating formulations containing 1.5% lignosulfonate (lanes 2-6) show retention of the dsRNA band in the gel, and some prevention of dsRNA degradation from UV radiation.

FIG. 31 is an example according to various embodiments, illustrating formulations containing 1.5% lignosulfonate (lanes 2-6) show retention of the dsRNA band in the gel, and some prevention of dsRNA degradation from UV radiation. The formulation that does not contain lignosulfonate exhibits complete loss of the dsRNA band on the gel and dsRNA degradation.

Figure 32:
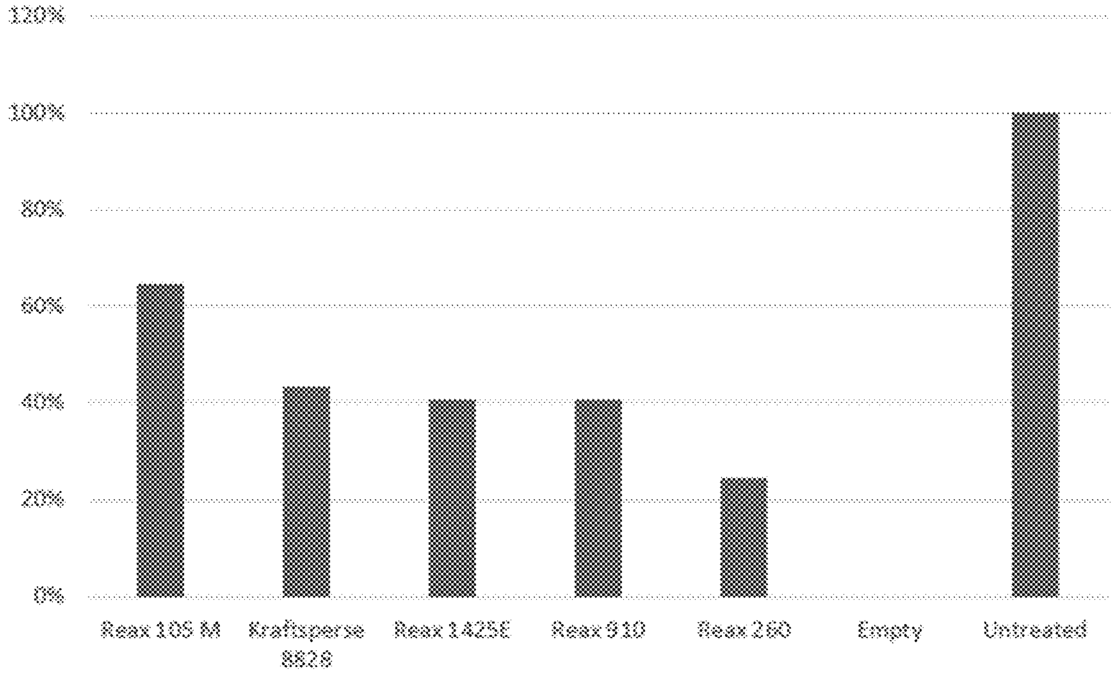
FIG. 32 is an example according to various embodiments, illustrating results from HPLC quantitation of formulations post exposure to 100 J/cm$^2$ UV-B radiation.

FIG. 32 is an example according to various embodiments, illustrating results from HPLC quantitation of formulations post exposure to 100 J/cm$^2$ UV-B radiation. Formulations containing lignosulfonate type surfactants demonstrate improvement of dsRNA stability upwards of 60 percent.

The formulations described above were prepared according to the method described in Example 1 and had the compositions according to Table 37.

TABLE 37

| Component | Target (wt. %) |
|---|---|
| dsRNA | 0.8 |
| ATPLUS ® PFA | 5 |
| Ethylenediaminetetraacetic acid (EDTA), Tetrasodium Tetrahydrate Salt | 1.583 |
| Propylene Glycol | 10 |
| Dibasic Potassium Phosphate | 1.869 |
| Monobasic Potassium Phosphate | 1.262 |
| Cetrimonium chloride | 0.25 |
| SAG1572 ™ | 0.05 |

TABLE 37-continued

| Component | Target (wt. %) |
|---|---|
| Dispersing Surfactant | 1.5 |
| KATHON ® CG/ICP | 0.05 |
| ROCIMA ® BT2S | 0.1 |
| Water | q.s. |

Example 34

Figure 33:
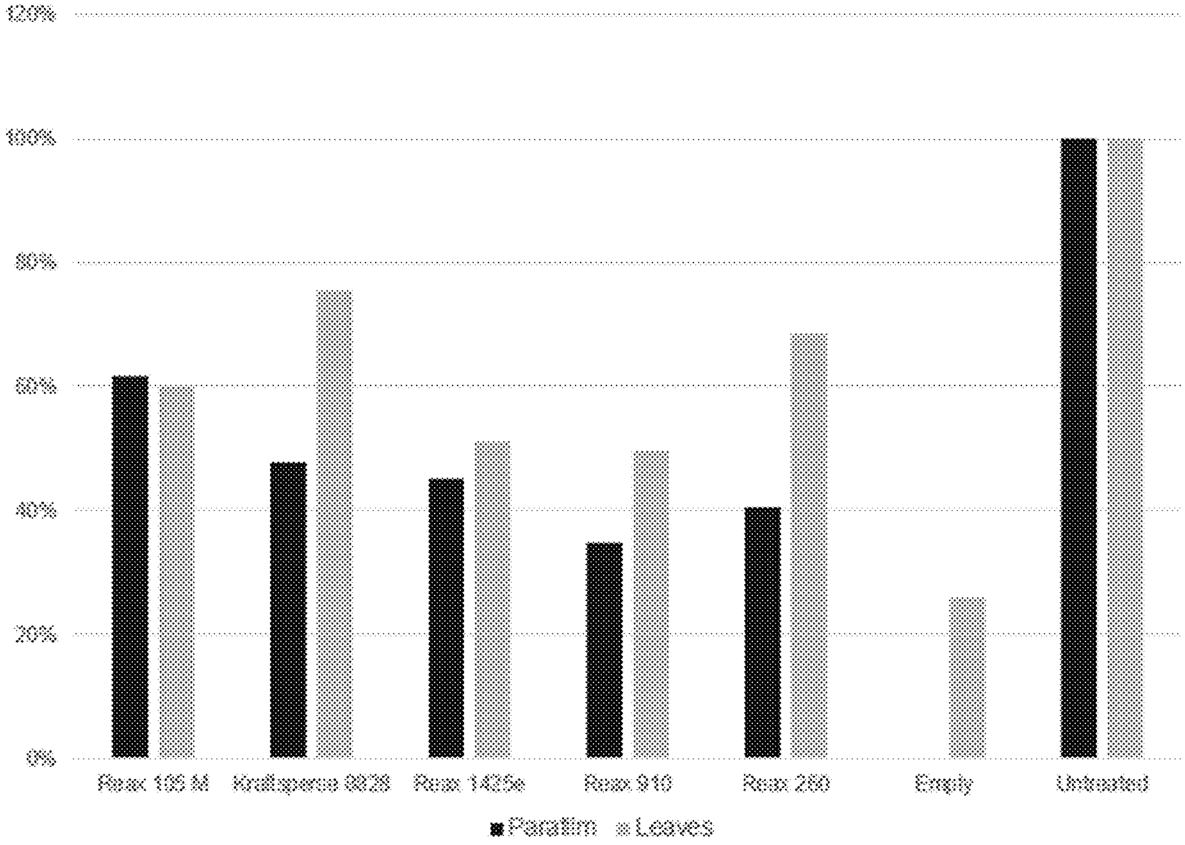
FIG. 33 is an example according to various embodiments, illustrating a comparison of dsRNA stability to UV radiation on leaf surfaces versus parafilm.

Formulated samples containing lignosulfonates were also dried on leaves to understand if any interactions with the leaf surface further improved dsRNA stability when exposed to UV radiation. A comparison between formulations exposed on parafilm plates, and on leaf surface is shown in FIG. 33. More specifically, FIG. 33 is an example according to various embodiments, illustrating a comparison of dsRNA stability to UV radiation on leaf surfaces versus parafilm. The leaf surface appears to offer an additional protection of dsRNA from UV radiation, improving stability of formulations containing dsRNA.

The formulations described above were prepared according to the method described in Example 1 and had the composition according to Example 34.

Example 35

Figure 34:
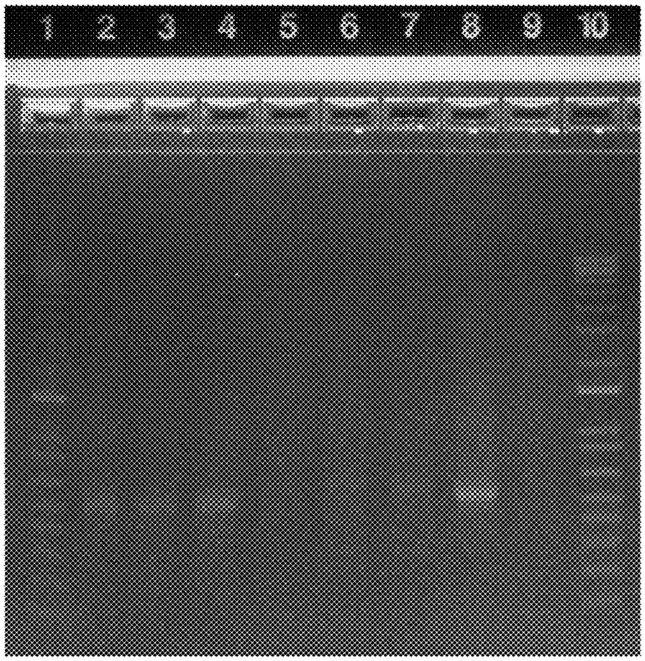
FIG. 34 is an example according to various embodiments, illustrating results from gel electrophoresis post UV-B exposure indicate that olefinic and phenyl based chemistries do not offer any significant protection of dsRNA.

Several other similar classes of chemistry to lignosulfonates were explored as possible UV absorbent surfactants including aromatic based chemistries, conjugated surfactants, and olefinic surfactants. Examples of these types of chemistries were found in naphthalene sulfonates, alkyl phenyl ethoxylates, and methyl oleyl taurates, and gel electrophoresis results of these types of additives is shown in FIG. 34. More specifically, FIG. 34 is an example according to various embodiments, illustrating results from gel electrophoresis post UV-B exposure indicate that olefinic and phenyl based chemistries do not offer any significant protection of dsRNA. Other conjugated chemistries, exemplified by the MORWET® series, shows slight improvement in dsRNA stability after UV-B exposure, but is not as significant a benefit as the lignosulfonate chemistry class.

The formulations described above were prepared according to the method described in Example 1 and had the composition of the previous example, where the 1.5% dispersing surfactant is replaced by these additional components.

Example 36

Qualitative and quantitative analysis of dsRNA formulations exposed to UV-B radiation demonstrate some level of dsRNA degradation, with the amount of degradation dependent on the class of surfactant used in the formulation. Formulations, post UV-B exposure, were used in a bioassay to determine whether the levels of degradation observed across the samples resulted in a loss of efficacy. Formulations were supplied with and without lignosulfonates to determine an improvements in efficacy as a result of the UV protectant, without exposure as a positive control, over exposed to 200 J/cm$^2$ for complete degradation as a negative control, and without the drying and rehydration step as a positive control. Results for the bioassay on Colorado potato beetle are shown FIGS. 35 and 36.

Figure 35:
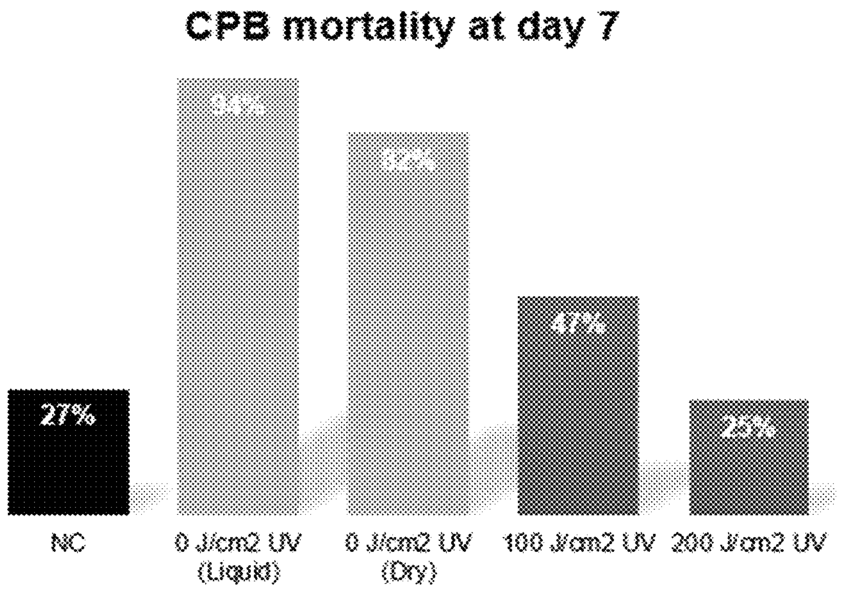
FIG. 35 is an example according to various embodiments, illustrating mortality results from a Colorado potato beetle (CPB) bioassay.

FIG. 35 is an example according to various embodiments, illustrating mortality results from a Colorado potato beetle (CPB) bioassay. Formulations that were not exposed to UV-B radiation demonstrated control in excess of 80% mortality, whereas exposure to 100 J/cm2 reduced mortality to 47%, and exposure to 200 J/cm2 reduced mortality to 25% which was equivalent to the non-treated control. Evaluation of formulations exposed to UV-B radiation demonstrates that the degradation of dsRNA observed in the gels and HPLC translates to significant loss of efficacy in bioassay.

The formulations described above were prepared according to the method described in Example 1 and had the composition as specified in Example 30.

Figure 36:
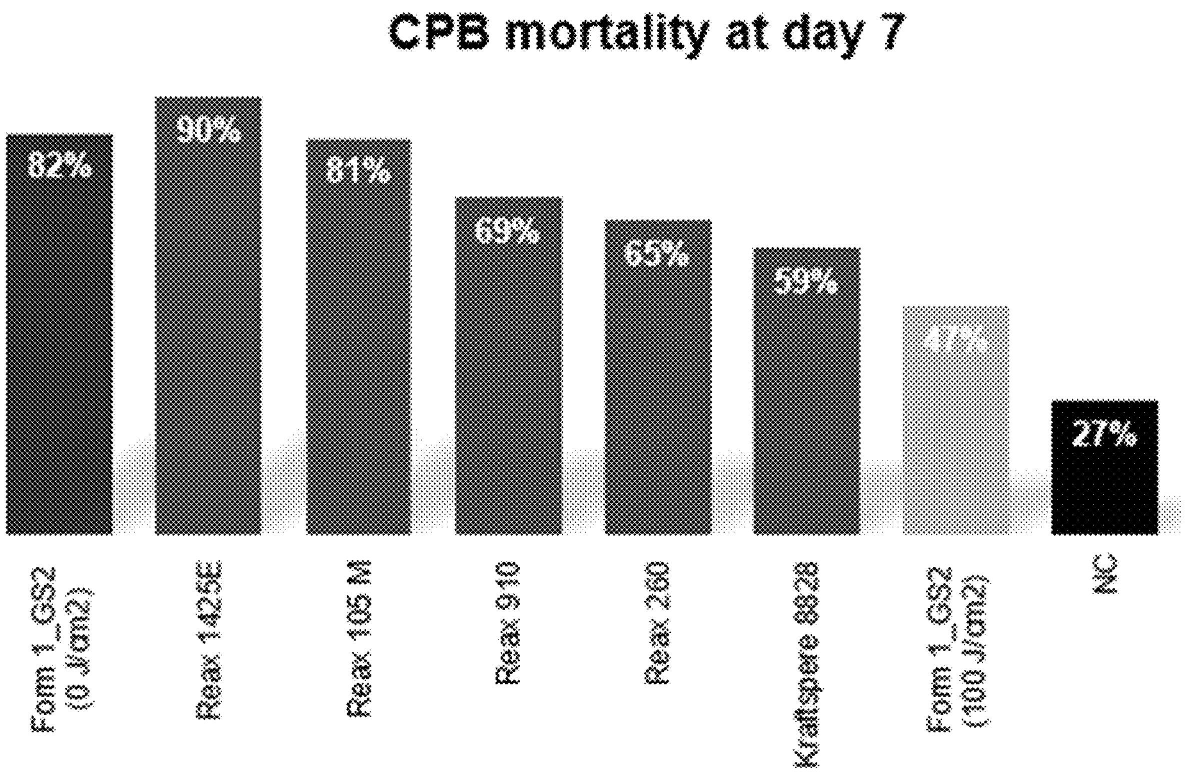
FIG. 36 is an example according to various embodiments, illustrating mortality results from a Colorado potato beetle (CPB) bioassay of formulations with and without lignosulfonate.

FIG. 36 is an example according to various embodiments, illustrating mortality results from a Colorado potato beetle (CPB) bioassay of formulations with and without lignosulfonate. Formulations with and without lignosulfonate were exposed to UV-B radiation and fed to CPB larvae. Several formulations containing lignosulfonate and exposed to 100 J/cm2 UV-B radiation provided similar, or better performance compared to a standard dsRNA formulation without UV-B exposure. All formulations containing lignosulfonates and exposed with 100 J/cm2 demonstrated an improvement in efficacy compared to the same formulation without lignosulfonate. Bioassay data confirms that protection against dsRNA degradation observed for the same samples in the qualitative and quantitative gel and HPLC assays, results in improvement in efficacy compared to samples that did not exhibit protection of dsRNA degradation from UV-B radiation.

The formulations described above were prepared according to the method described in Example 1 and had the compositions according to Table 38.

TABLE 38

| Component | Target (wt. %) |
|---|---|
| dsRNA | 0.8 |
| ATPLUS ® PFA | 5 |
| Ethylenediaminetetraacetic acid (EDTA), Tetrasodium Tetrahydrate Salt | 1.583 |
| Propylene Glycol | 10 |
| Dibasic Potassium Phosphate | 1.869 |
| Monobasic Potassium Phosphate | 1.262 |
| Cetrimonium chloride | 0.25 |
| SAG1572 ™ | 0.05 |
| Dispersing Surfactant (REAX ® 1425E, REAX ® 105M, REAX ® 910, REAX ® 260, KRAFTSPERSE ® 8828, or none) | 1.5 |
| KATHON ® CG/ICP | 0.05 |
| ROCIMA ® BT2S | 0.1 |
| Water | q.s. |

Example 37

Compositions according to Table 39 was prepared. Samples incorporating various different dsRNA sequences were tested for stability at various times and temperatures, as set forth in Tables 40A, 40B, and 40C. One sample comprises a 497 bp dsRNA targeting a gene of the fungus *Erysiphe necator* (Table 40A); one sample comprises a 478 bp dsRNA targeting a gene of the fungus *Botrytis cinerea*; and one sample comprises a 450 bp dsRNA targeting a gene of the fungus *Botrytis cinerea.*

To determine physical stability, samples were observed for any visual separation with the naked eye, inverting the samples slowly to examine for sediment. All samples were observed to be homogenous demonstrating the physical stability of all samples under all conditions tested.

To evaluate chemical stability, initial pH was set to about 6 with citrate buffer and the pH of each sample was measured at various times using an electronically calibrated pH meter using as described in CIPAC MT 75.3. All samples demonstrated strong chemical stability at all times and temperatures, with pH varying by at most 0.16, 0.31, 0.29 for the three samples as respectively set forth in FIGS. 40A, 40B, and 40C, well below the threshold for a chemically stable composition.

To evaluate physical stability after dilution into water, concentrated product was diluted to the to the targeted rate in the water hardness listed in FIGS. 40A, 40B, and 40C. The waters were prepared according to the ASTM method, similar to the method of ASTM E1945-02. Samples were mixed briefly and then observed for any cloudiness or precipitation, similar to the method of method CIPAC MT 41. No cloudiness or precipitation is observed for any sample at any time or temperature, demonstrating the stability of diluted product.

To evaluate chemical stability of the composition, total dsRNA content was measured by HPLC with a target concentration of 0.8% w/w or 8.24 g/L. The analytical method variability can be estimated to plus or minus 15%. HPLC results were confirmed by gel electrophoresis. No dsRNA degradation is observed below 7.0 g/L at any time-point, demonstrating the stability of all samples tested.

TABLE 39

| Component | Target (wt. %) |
|---|---|
| dsRNA | 53.33 |
| BIO-SOFT ® N23-6.5 (C12-C13 linear alcohol ethoxylate) | 7.00 |
| Propylene Glycol | 10.00 |
| Sodium Citrate Buffer ph 6 | 1.32 |
| Citric Acid | 0.1 |
| REAX ® 105M (sodium lignosulfonate dispersant) | 2.00 |
| SAG1572 ™ Antifoam | 0.05 |
| KATHON ® CG/ICP | 0.05 |
| ROCIMA ® BT2S | 0.10 |
| NOVERITE ® K-775 (acrylate copolymer) | 0.50 |
| Water | q.s. |

TABLE 40A

| | | | | | | |
|---|---|---|---|---|---|---|
| Sample | TF221024_JE_11 | | | | | |
| Density | 1.0306 | g/ml | | | | |
| | | 2 weeks | 2 weeks | 2 weeks | 8 weeks | 8 weeks |
| | T0 | −20 C. | 54 C. | −10 to 40 | 40 C. | RT |
| Physical Appearance | Homogenous | Homogenous | Homogenous | Homogenous | Homogenous | Homogenous |
| pH | 5.89 | 5.81 | 5.96 | 5.99 | 6.07 | 6.18 |
| Dilution Stability 1.33% v/v | | | | | | |
| 35 PPM | | | | | | |
| T0 | Clear | Clear | Clear | Clear | Clear | Clear |
| 24 hrs | Clear | Clear | Clear | Clear | Clear | Clear |
| 342 PPM | | | | | | |
| T0 | Clear | Clear | Clear | Clear | Clear | Clear |
| 24 hrs | Clear | Clear | Clear | Clear | Clear | Clear |
| 1000 PPM | | | | | | |
| T0 | Clear | Clear | Clear | Clear | Clear | Clear |
| 24 hrs | Clear | Clear | Clear | Clear | Clear | Clear |
| HPLC Analysis | 7.32 | 8.74 | 8.05 | 8.05 | 8.8 | 8.8 |

TABLE 40B

| | | | | | | |
|---|---|---|---|---|---|---|
| Sample | TF210406_JE_02 | | | | | |
| Density | 1.0312 | g/ml | | | | |
| | | 1 week | 2 weeks | 2 weeks | 8 weeks | 8 weeks |
| | T0 | −20 C. | 54 C. | −10 to 40 | 40 C. | RT |
| Physical Appearance | N/A | Homogenous | Homogenous | Homogenous | Homogenous | Homogenous |
| pH | 6.4 | 6.19 | 6.2 | 6.21 | 6.14 | 6.09 |
| Dilution Stability 5% v/v | | | | | | |
| 35 PPM | | | | | | |
| T0 | Clear | Clear | Clear | Clear | Clear | Clear |
| 24 hrs | Clear | Clear | Clear | Clear | Clear | Clear |
| 342 PPM | | | | | | |
| T0 | Clear | Clear | Clear | Clear | Clear | Clear |
| 24 hrs | Clear | Clear | Clear | Clear | Clear | Clear |
| 1000 PPM | | | | | | |

TABLE 40B-continued

| | | | | | | |
|---|---|---|---|---|---|---|
| T0 | Clear | Clear | Clear | Clear | Clear | Clear |
| 24 hrs | Clear | Clear | Clear | Clear | Clear | Clear |
| HPLC Quantification (g/L) | 7.946 | 8.064 | 7.72 | 7.666 | 7.156 | 7.758 |

TABLE 40C

| Sample | TF210825_JE_11 | | | | | |
|---|---|---|---|---|---|---|
| Density | 1.0314 | g/ml | | | | |
| | T0 | 1 week −20 C. | 2 weeks 54 C. | 2 weeks −10 to 40 | 8 weeks 40 C. | 8 weeks RT |
| Physical Appearance | Uniform | Uniform | Uniform | Uniform | Uniform | Uniform |
| pH | 6.02 | 6.15 | 6.1 | 6.18 | 5.86 | 5.9 |
| Dilution Stability 1.33% v/v | | | | | | |
| 35 PPM | | | | | | |
| T0 | Clear | Clear | Clear | Clear | Clear | Clear |
| 24 hrs | Clear | Clear | Clear | Clear | Clear | Clear |
| 342 PPM | | | | | | |
| T0 | Clear | Clear | Clear | Clear | Clear | Clear |
| 24 hrs | Clear | Clear | Clear | Clear | Clear | Clear |
| 1000 PPM | | | | | | |
| T0 | Clear | Clear | Clear | Clear | Clear | Clear |
| 24 hrs | Clear | Clear | Clear | Clear | Clear | Clear |
| HPLC Analysis | 7.8 | 9.04 | 9.95 | 8.76 | 8.45 | 8.71 |

Example 38

This example covers a multiparameter investigation of factors leading to physical stability of the dsRNA concentration, the primary surfactant, the secondary surfactant, and the metal ion sequestrant. JMP (Version 15.2.0, SAS Institute, Cary NC, 18) was used to construct a statistical design of experiments within the following parameters.

TABLE 41

| Component | Range Target (wt. %) |
|---|---|
| dsRNA | 0.8-1.2 |
| ATPLUS ® PFA | 4-10 |
| Ethylenediaminetetraacetic acid (EDTA), Tetrasodium Tetrahydrate Salt | 0.05-3.0 |
| Cetrimonium chloride | 0.05-3 |

Figure 37:
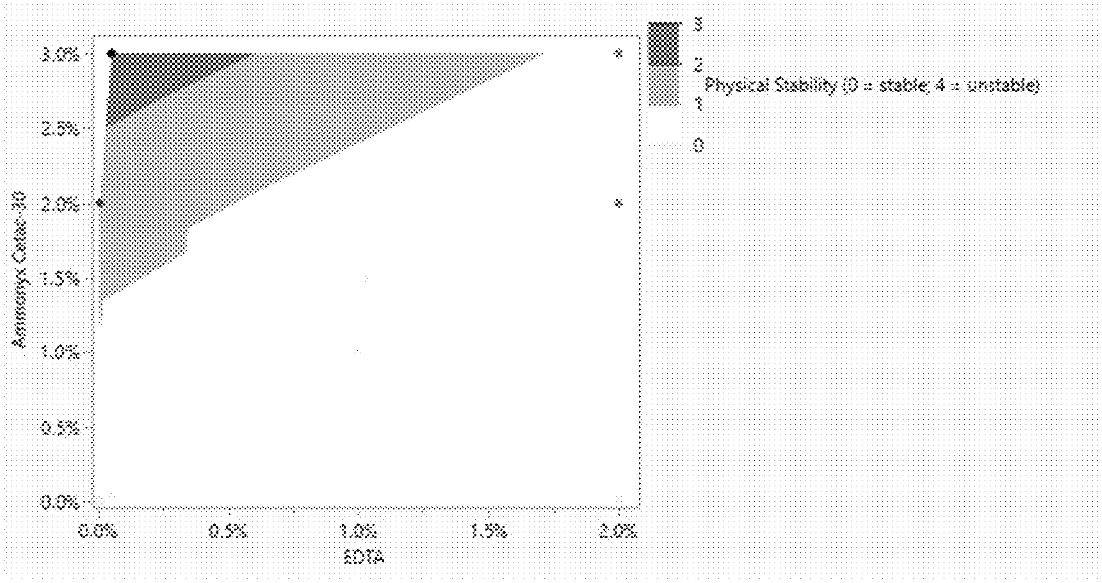
FIG. 37 shows an statistical design of experiments evaluation of stability for relative concentrations of cetrimonium chlorate and EDTA.

Within this range of tested parameters the dsRNA concentration did not have a significant effect on the physical stability of the composition after storage. The cetrimonium chloride did have a significant effect on the stability where the combination of low EDTA and high cetrimonium chloride did lead to instability as shown in the dark grey area of FIG. 37 showing the relationship between EDTA and cetrimonum chloride. FIG. 39 describes the significant relationships between EDTA and cetrimonium chloride on formulation stability. At the highest tested levels of ATPLUS® PFA (10 wt %), minimal precipitate was observed under some conditions, however it was not a significant factor in the DOE, within acceptable limits The DOE confirms that within the tested compositions ranges, physically stable mixtures with dsRNA can be made at all compositions except those at low EDTA and high cetrimonium chloride concentrations.

Example 39

Compositions according to Table 19 were prepared and tested at various times and temperature conditions to evaluate various metrics for stability. A sample was initially evaluated for pH, density of dsRNA, dilution stability, and foaming. Remaining samples were sealed with aluminum in a container and stored at under various conditions and times, including after 1 year and 2 years at room temperature and at 4 weeks at 54° C. (simulating at least a 2-year storage at room temperature). Samples were then evaluated to confirm stability. As set forth in Table 42, these samples remained within or minimally outside the 10% detection range of the HPLC method, demonstrating minimal to no detectable degradation of dsRNA due to nucleases, fungal contamination, or bacterial contamination. The pH levels remained well within even a one-unit threshold for stability, with the pH varying at most by 0.19 units from the initial pH of 7. Physical stability was evaluated by examining for color of the concentrate sample and evaluating precipitation both in the stored concentrate sample and 18 hours after diluting the concentrate samples. Samples were clear or mostly clear in appearance. No precipitation was observed in the samples before or after dilution. Foaming was tested according to CPAC MT47 and all samples were less than the standard 15% foam/solution v/v after one minute.

TABLE 42

| Time | Temp (° C.) | dsRNA (g/L) | pH | Appearance | Dilution Stability | Persistent Foaming (% v/v after 1 min.) |
|---|---|---|---|---|---|---|
| Initial | RT | 7.6 | 7 | Clear | No precipitates | <15 |
| 2 Months | 54 | 6.82 | 7.18 | Clear | No precipitates | <15 |
| 1 Year | RT | 7.25 | 6.81 | Clear | No precipitates | <15 |
| 2 Years | RT | 8.32 | 7.16 | Mostly Clear | No precipitates | <15 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present disclosure have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method stabilizing RNA, the method comprising combining the RNA with a primary surfactant, a secondary surfactant and a metal-ion sequestrant to produce a composition, the RNA being dsRNA or single-stranded RNA and present in the composition in an amount from about 0.4 to about 10 percent by weight based on the total weight of the composition; the primary surfactant being a nonionic surfactant and present in the composition in an amount of from about 4 to about 7 percent by weight based on the total weight of the composition; the secondary surfactant being selected from the group consisting of a cationic surfactant, a zwitterionic surfactant, an amphoteric surfactant, and combinations thereof, and present in an amount of from about 0.5 to about 3 percent by weight based on the total weight of the composition; and the metal-ion sequestrant being present in an amount of from about 0.6 to about 3 percent by weight based on the total weight of the composition.

2. The method according to claim 1, wherein the composition is a soluble liquid concentrate.

3. The method according to claim 1, wherein the composition further comprises one or more of the following:

a UV protectant;

at least one buffer;

at least one biological preservative;

an antifoam agent; and/or an antifreeze agent.

4. The method according to claim 3, wherein the composition comprises the UV protectant, the UV protectant being present in an amount of from about 1 to about 15 percent by weight based on the total weight of the composition.

5. The method according to claim 3, wherein the composition comprises the UV protectant, the UV protectant comprising a UV protectant selected from the group consisting of a conjugated aromatic surfactant or a polymeric surfactants containing conjugated aromatic functionalities.

6. The method according to claim 3, wherein the composition comprises the UV protectant, the UV protectant comprising a sodium lignosulfonate dispersant.

7. The method according to claim 3, wherein the composition comprises the at least one buffer, the at least one buffer being individually present in an amount of from about 1 to about 7 percent by weight based on the total weight of the composition.

8. The method according to claim 3, wherein the composition comprises the at least one buffer, the at least one buffer-comprising monobasic potassium phosphate and dibasic potassium phosphate, or the at least one buffer comprising sodium citrate and citric acid.

9. The method according to claim 3, wherein the composition comprises the at least one biological preservative, wherein the at least one biological preservative comprises an active ingredient selected from the group consisting of 5-chloro-2-methyl-4-isothiazolin-3-one (CMIT), 2-methyl-4-isothiazolin-3-one (MIT), 1,2-Benzisothiazolin-3-one (BIT), and combinations thereof.

10. The method according to claim 3, wherein the composition comprises the at least one biological preservative, the at least one biological preservative being individually present in an amount of from about 0.05 to about 1 percent by weight based on the total weight of the composition.

11. The method according to claim 1, wherein the primary surfactant is selected from the group consisting of a polysorbate, an alkoxylate, a nonoxynol, a poloxamer, and combinations thereof.

12. The method according to claim 1, wherein the primary surfactant is selected from the group consisting of polysorbate 20, an alkoxylated alcohol, and an alkoxylate mixture of $C_{12}$-$C_{13}$ alcohol.

13. The method according to claim 1, wherein the metal-ion sequestrant is selected from the group consisting of EDTA and an acrylate copolymer.

14. The method according to claim 1, wherein the secondary surfactant is selected from the group consisting of an alkyl ammonium halide, lauryl betaine, an amine oxide, and combinations thereof.

15. The method according to claim 1, wherein the secondary surfactant comprises cetrimonium chloride.

16. The method according to claim 1, wherein the composition is sufficient to provide shelf stability to the RNA for one year at room temperature.

17. The method of claim 1, wherein, the pH of the composition remains within 2 units of the initial pH after the composition is stored for a time at a temperature selected from the group consisting of 2 weeks at −20° C., 2 weeks at −10-40° C. cycling, 2 weeks at 54° C., 8 weeks at 40° C., 4 weeks at 54° C., 8 weeks at 54° C., 1 year at room temperature, and 2 years at room temperature.

18. The method of claim 17, wherein the time and the temperature is selected from the group consisting of 2 weeks at 54° C. and 2 years at room temperature.

19. The method of claim 1, wherein the RNA present in the composition remains within 15% of the initial concentration of RNA present in the composition as measured by HPLC, after the composition is stored for a time and at a temperature selected from the group consisting of 2 weeks at −20° C., 2 weeks at −10-40° C. cycling, 2 weeks at 54° C., 8 weeks at 40° C., 4 weeks at 54° C., 8 weeks at 54° C., 1 year at room temperature, and 2 years at room temperature.

20. The method of claim 19, wherein the time and the temperature is selected from the group consisting of 2 weeks at 54° C. and 2 years at room temperature.

21. The method of claim 1, wherein the RNA is dsRNA.

22. The method of claim 1, wherein the secondary surfactant is a cationic surfactant.

* * * * *